(12) United States Patent
Ben-Ezra et al.

(10) Patent No.: US 9,179,963 B2
(45) Date of Patent: Nov. 10, 2015

(54) BLADDER TISSUE MODIFICATION FOR OVERACTIVE BLADDER DISORDERS

(71) Applicant: NewUro, B.V., Amsterdam (NL)

(72) Inventors: Omry Ben-Ezra, Tel Aviv (IL); Itzhak Avneri, Tel Aviv (IL); Shahar Avneri, Herzliya (IL)

(73) Assignee: NewUro, B.V., Amsterdam (NL)

( * ) Notice: Subject to any disclaimer, the term of this patent is extended or adjusted under 35 U.S.C. 154(b) by 0 days.

(21) Appl. No.: 14/602,493

(22) Filed: Jan. 22, 2015

(65) Prior Publication Data

US 2015/0157391 A1 Jun. 11, 2015

Related U.S. Application Data

(63) Continuation of application No. 14/519,933, filed on Oct. 21, 2014, which is a continuation-in-part of application No. PCT/IB2013/001203, filed on Apr. 19, 2013.

(60) Provisional application No. 61/636,686, filed on Apr. 22, 2012, provisional application No. 61/649,334, filed on May 20, 2012, provisional application No. 61/908,748, filed on Nov. 26, 2013, provisional application No. 61/972,441, filed on Mar. 31, 2014.

(51) Int. Cl.
*A61B 18/14* (2006.01)
*A61B 17/32* (2006.01)
(Continued)

(52) U.S. Cl.
CPC .............. *A61B 18/14* (2013.01); *A61B 17/32* (2013.01); *A61B 18/02* (2013.01); *A61B 18/1492* (2013.01); *A61B 18/18* (2013.01); *A61B 18/1815* (2013.01); *A61N 7/00* (2013.01); *A61B 2017/320004* (2013.01); *A61B 2018/0016* (2013.01); *A61B 2018/0022* (2013.01); *A61B 2018/00214* (2013.01); *A61B 2018/00488* (2013.01); *A61B 2018/00494* (2013.01); *A61B 2018/00511* (2013.01); *A61B 2018/00517* (2013.01); *A61B 2018/00541* (2013.01);
(Continued)

(58) Field of Classification Search
None
See application file for complete search history.

(56) References Cited

U.S. PATENT DOCUMENTS

| 4,808,164 A | 2/1989 | Hess |
| 5,056,531 A | 10/1991 | Shimoyama |

(Continued)

FOREIGN PATENT DOCUMENTS

| WO | WO 2005/067791 A1 | 7/2005 |
| WO | WO 2013/160772 A2 | 10/2013 |

OTHER PUBLICATIONS

U.S. Appl. No. 14/519,933, filed Oct. 21, 2014, Roberts.

(Continued)

*Primary Examiner* — Michael Peffley
(74) *Attorney, Agent, or Firm* — Wilson Sonsini Goodrich & Rosati

(57) ABSTRACT

Regions of tissue having reduced electrical propagation are created in a bladder to affect its electrical or mechanical properties. To create these tissue regions, a tubular device is advanced through the urethra leading to the interior of the bladder, a distal expandable structure of the device is expanded to contact the inner wall of the bladder, and electrodes or other active energy delivery elements of the device are activated to deliver ablation energy. The electrodes or other active energy delivery elements are disposed over the expandable structure which is shaped to conform to the interior of the bladder. The inner wall of the organ is ablated in a predetermined pattern. The same or other electrodes disposed over the expandable structure can used to electrically map the bladder. This map of electrical activity can be used to create the predetermined pattern.

49 Claims, 42 Drawing Sheets

(51) Int. Cl.
*A61B 18/02* (2006.01)
*A61B 18/18* (2006.01)
*A61N 7/00* (2006.01)
*A61B 18/00* (2006.01)

(52) U.S. Cl.
CPC .............. *A61B2018/00559* (2013.01); *A61B 2018/00577* (2013.01); *A61B 2018/00839* (2013.01); *A61B 2018/00982* (2013.01); *A61B 2018/0212* (2013.01); *A61B 2018/144* (2013.01); *A61B 2018/1465* (2013.01); *A61B 2018/1861* (2013.01); *A61N 2007/0043* (2013.01)

(56) References Cited

U.S. PATENT DOCUMENTS

| | | |
|---|---|---|
| 5,057,106 A | 10/1991 | Kasevich et al. |
| 5,105,360 A | 4/1992 | Akiyama |
| 5,150,717 A | 9/1992 | Rosen et al. |
| 5,178,618 A * | 1/1993 | Kandarpa ............. 606/28 |
| 5,188,602 A | 2/1993 | Nichols |
| 5,209,749 A * | 5/1993 | Buelna ............. 606/45 |
| 5,380,319 A | 1/1995 | Saito et al. |
| 5,405,346 A | 4/1995 | Grundy et al. |
| 5,470,352 A | 11/1995 | Rappaport |
| 5,480,417 A | 1/1996 | Hascoet et al. |
| 5,509,929 A | 4/1996 | Hascoet et al. |
| 5,578,008 A | 11/1996 | Hara |
| 5,599,294 A | 2/1997 | Edwards et al. |
| 5,628,746 A * | 5/1997 | Clayman ............. 606/45 |
| 5,649,973 A | 7/1997 | Tierney et al. |
| 5,800,486 A | 9/1998 | Thome et al. |
| 5,827,273 A | 10/1998 | Edwards |
| 5,902,251 A | 5/1999 | Vanhooydonk |
| 5,967,984 A * | 10/1999 | Chu et al. ............. 600/439 |
| 5,989,284 A | 11/1999 | Laufer |
| 5,992,419 A | 11/1999 | Sterzer et al. |
| 6,001,093 A | 12/1999 | Swanson et al. |
| 6,024,743 A | 2/2000 | Edwards |
| 6,036,689 A * | 3/2000 | Tu et al. ............. 606/41 |
| 6,053,937 A | 4/2000 | Edwards et al. |
| 6,083,255 A | 7/2000 | Laufer et al. |
| 6,097,985 A | 8/2000 | Kasevich et al. |
| 6,161,049 A | 12/2000 | Rudie et al. |
| 6,223,085 B1 | 4/2001 | Dann et al. |
| 6,254,598 B1 * | 7/2001 | Edwards et al. ............. 606/41 |
| 6,283,989 B1 | 9/2001 | Laufer et al. |
| 6,353,751 B1 | 3/2002 | Swanson et al. |
| 6,458,098 B1 | 10/2002 | Kanesaka |
| 6,496,737 B2 | 12/2002 | Rudie et al. |
| 6,629,535 B2 | 10/2003 | Ingle et al. |
| 6,692,490 B1 | 2/2004 | Edwards |
| 6,740,108 B1 | 5/2004 | Just et al. |
| 6,875,209 B2 | 4/2005 | Zvuloni et al. |
| 6,997,924 B2 | 2/2006 | Schwartz et al. |
| 7,001,378 B2 | 2/2006 | Yon et al. |
| 7,022,120 B2 | 4/2006 | Lafontaine |
| 7,060,062 B2 | 6/2006 | Joye et al. |
| 7,074,233 B1 | 7/2006 | Gowda et al. |
| 7,081,112 B2 | 7/2006 | Joye et al. |
| 7,083,614 B2 | 8/2006 | Fjield et al. |
| 7,101,368 B2 | 9/2006 | Lafontaine |
| 7,101,387 B2 | 9/2006 | Garabedian et al. |
| 7,192,438 B2 | 3/2007 | Margolis |
| 7,195,625 B2 | 3/2007 | Lentz |
| 7,220,257 B1 | 5/2007 | Lafontaine |
| 7,278,991 B2 | 10/2007 | Morris et al. |
| 7,278,994 B2 | 10/2007 | Goble |
| 7,288,087 B2 | 10/2007 | Winston et al. |
| 7,288,089 B2 | 10/2007 | Yon et al. |
| 7,300,433 B2 | 11/2007 | Lane et al. |
| 7,326,235 B2 | 2/2008 | Edwards |
| 7,357,796 B2 | 4/2008 | Farr et al. |
| 7,371,231 B2 | 5/2008 | Rioux et al. |
| 7,381,208 B2 | 6/2008 | van der Walt et al. |
| 7,410,486 B2 | 8/2008 | Fuimaono et al. |
| 7,500,973 B2 | 3/2009 | Vancelette et al. |
| 7,507,234 B2 | 3/2009 | Utley et al. |
| 7,527,622 B2 | 5/2009 | Lane et al. |
| 7,556,628 B2 | 7/2009 | Utley et al. |
| 7,625,368 B2 | 12/2009 | Schechter et al. |
| 7,632,268 B2 | 12/2009 | Edwards et al. |
| 7,648,497 B2 | 1/2010 | Lane et al. |
| 7,655,005 B2 | 2/2010 | Bhola |
| 7,655,006 B2 | 2/2010 | Sauvageau et al. |
| 7,744,594 B2 | 6/2010 | Yamazaki et al. |
| 7,761,169 B2 | 7/2010 | Zelickson et al. |
| 7,813,313 B2 | 10/2010 | Pan et al. |
| 7,837,720 B2 | 11/2010 | Mon |
| 7,846,153 B2 | 12/2010 | Hebert et al. |
| 7,850,681 B2 | 12/2010 | Lafontaine |
| 7,892,229 B2 | 2/2011 | Shadduk et al. |
| 8,007,496 B2 | 8/2011 | Rioux et al. |
| 8,137,342 B2 | 3/2012 | Crossman |
| RE38,229 E | 10/2013 | Ben-Ezra et al. |
| 8,685,050 B2 * | 4/2014 | Schur et al. ............. 606/159 |
| 2001/0014805 A1 | 8/2001 | Burbank et al. |
| 2002/0183735 A1 | 12/2002 | Edwards et al. |
| 2003/0055470 A1 | 3/2003 | Mon et al. |
| 2003/0060762 A1 | 3/2003 | Zvuloni et al. |
| 2003/0060813 A1 | 3/2003 | Loeb et al. |
| 2003/0069619 A1 | 4/2003 | Fenn et al. |
| 2004/0133254 A1 | 7/2004 | Sterzer et al. |
| 2004/0147915 A1 | 7/2004 | Hasebe |
| 2004/0172112 A1 | 9/2004 | Cioanta et al. |
| 2004/0186468 A1 | 9/2004 | Edwards |
| 2004/0243199 A1 | 12/2004 | Mon et al. |
| 2005/0096647 A1 | 5/2005 | Steinke et al. |
| 2005/0107783 A1 | 5/2005 | Tom et al. |
| 2005/0124843 A1 | 6/2005 | Singh |
| 2005/0131500 A1 | 6/2005 | Zalesky et al. |
| 2005/0165389 A1 | 7/2005 | Swain et al. |
| 2005/0228370 A1 | 10/2005 | Sterzer et al. |
| 2005/0251125 A1 | 11/2005 | Pless et al. |
| 2006/0009758 A1 | 1/2006 | Edwards |
| 2006/0118127 A1 | 6/2006 | Chinn |
| 2006/0167442 A1 | 7/2006 | Hebert et al. |
| 2006/0253113 A1 | 11/2006 | Arnold et al. |
| 2006/0253178 A1 | 11/2006 | Masotti |
| 2006/0259029 A1 | 11/2006 | Utley et al. |
| 2007/0005050 A1 | 1/2007 | Duong et al. |
| 2007/0038203 A1 | 2/2007 | McIntyre |
| 2007/0049918 A1 | 3/2007 | Van Der Weide et al. |
| 2007/0066973 A1 | 3/2007 | Stern et al. |
| 2007/0078451 A1 | 4/2007 | Arnold et al. |
| 2007/0088247 A1 | 4/2007 | Bliweis et al. |
| 2007/0129725 A1 | 6/2007 | Houser |
| 2007/0282184 A1 | 12/2007 | Roberts |
| 2007/0293854 A1 | 12/2007 | Pless et al. |
| 2008/0004613 A1 | 1/2008 | Barbut et al. |
| 2008/0077174 A1 | 3/2008 | Mische |
| 2008/0097427 A1 | 4/2008 | Stern et al. |
| 2008/0125765 A1 | 5/2008 | Berenshyteyn et al. |
| 2008/0140067 A1 | 6/2008 | Vetter et al. |
| 2008/0140070 A1 | 6/2008 | Filloux et al. |
| 2008/0172050 A1 | 7/2008 | Satake |
| 2008/0223380 A1 | 9/2008 | Chinn |
| 2008/0249518 A1 | 10/2008 | Warnking et al. |
| 2008/0262489 A1 | 10/2008 | Steinke |
| 2008/0312642 A1 | 12/2008 | Kania et al. |
| 2009/0018533 A1 | 1/2009 | Perkins et al. |
| 2009/0076494 A1 | 3/2009 | Azure |
| 2009/0131928 A1 | 5/2009 | Edwards et al. |
| 2009/0163906 A1 | 6/2009 | Faure |
| 2009/0248012 A1 | 10/2009 | Maor et al. |
| 2009/0281532 A1 | 11/2009 | Reddy |
| 2009/0306644 A1 | 12/2009 | Mayse et al. |
| 2009/0318914 A1 | 12/2009 | Utley et al. |
| 2010/0004650 A1 | 1/2010 | Ormsby et al. |
| 2010/0030204 A1 | 2/2010 | Stein et al. |
| 2010/0049031 A1 | 2/2010 | Fruland et al. |
| 2010/0049182 A1 | 2/2010 | Ryan et al. |
| 2010/0049186 A1 | 2/2010 | Ingle et al. |

(56) References Cited

U.S. PATENT DOCUMENTS

| | | |
|---|---|---|
| 2010/0049192 A1 | 2/2010 | Holtz et al. |
| 2010/0076402 A1 | 3/2010 | Mazzone et al. |
| 2010/0076425 A1 | 3/2010 | Carroux |
| 2010/0114087 A1 | 5/2010 | Edwards et al. |
| 2010/0160906 A1 | 6/2010 | Jarrard |
| 2010/0168734 A1 | 7/2010 | Dicarlo |
| 2010/0179530 A1 | 7/2010 | Long et al. |
| 2010/0198066 A1 | 8/2010 | Voegele |
| 2010/0234840 A1 | 9/2010 | Jackson et al. |
| 2010/0262140 A1 | 10/2010 | Watson et al. |
| 2010/0280510 A1 | 11/2010 | Smith et al. |
| 2010/0286688 A1 | 11/2010 | Hughett et al. |
| 2010/0286753 A1 | 11/2010 | Zelickson et al. |
| 2010/0305562 A1 | 12/2010 | Winkler et al. |
| 2011/0028886 A1 | 2/2011 | Mon |
| 2011/0034976 A1 | 2/2011 | Mon et al. |
| 2011/0082450 A1 | 4/2011 | Melsky et al. |
| 2011/0098694 A1 | 4/2011 | Long |
| 2011/0112432 A1 | 5/2011 | Toth |
| 2011/0118719 A1 | 5/2011 | Vissy et al. |
| 2011/0152839 A1 | 6/2011 | Cima et al. |
| 2011/0152855 A1 | 6/2011 | Mayse et al. |
| 2011/0166570 A1 | 7/2011 | Hawkins et al. |
| 2011/0257647 A1 | 10/2011 | Mayse et al. |
| 2011/0264085 A1 | 10/2011 | Satake |
| 2011/0264086 A1 | 10/2011 | Ingle |
| 2011/0301662 A1 | 12/2011 | Bar-Yoseph et al. |
| 2011/0306904 A1 | 12/2011 | Jacobson et al. |
| 2011/0319880 A1 | 12/2011 | Prakash et al. |
| 2012/0004654 A1 | 1/2012 | Jackson et al. |
| 2012/0004656 A1 | 1/2012 | Jackson et al. |
| 2012/0016358 A1 | 1/2012 | Mayse et al. |
| 2012/0022520 A1 | 1/2012 | Bek |
| 2012/0029500 A1 | 2/2012 | Jenson |
| 2012/0059368 A1 | 3/2012 | Takaoka et al. |
| 2012/0065636 A1 | 3/2012 | Thompson et al. |
| 2012/0071870 A1 | 3/2012 | Salahieh et al. |
| 2012/0071873 A1 | 3/2012 | Thompson et al. |
| 2012/0101490 A1 | 4/2012 | Smith |
| 2012/0116384 A1 | 5/2012 | Truckai |
| 2012/0130363 A1 | 5/2012 | Kim et al. |
| 2012/0143179 A1 | 6/2012 | Avitall |
| 2013/0018281 A1 | 1/2013 | Nagale et al. |
| 2013/0066308 A1 | 3/2013 | Landman |
| 2014/0324036 A1 | 10/2014 | Sachs et al. |
| 2015/0157389 A1 | 6/2015 | Ben-Ezra et al. |

OTHER PUBLICATIONS

International search report and written opinion dated Jan. 24, 2014 for PCT Application No. IB2013/001203.

Parsons, et al. A Further Assessment of Bladder Transection in the Management of Adult Enuresis and Allied Conditions. Br J Urol. Nov. 1977;49(6):509-14.

International search report and written opinion dated Aug. 12, 2015 for PCT Application No. IB2014/003083.

* cited by examiner

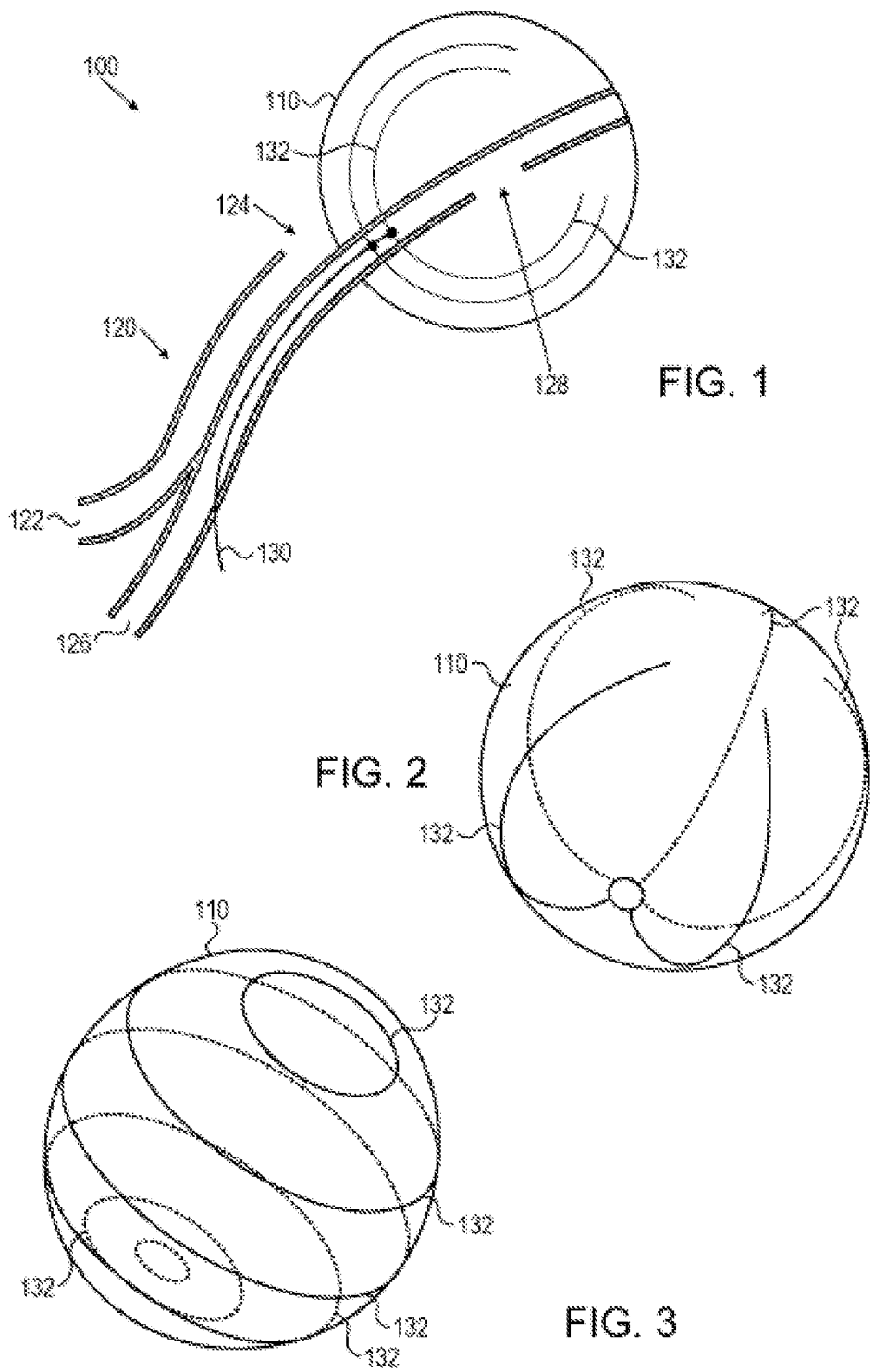

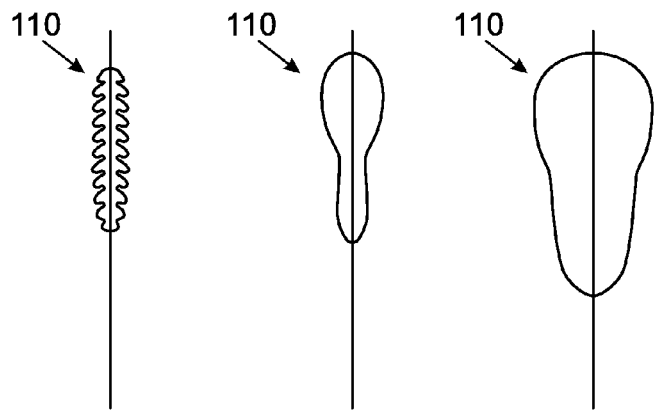
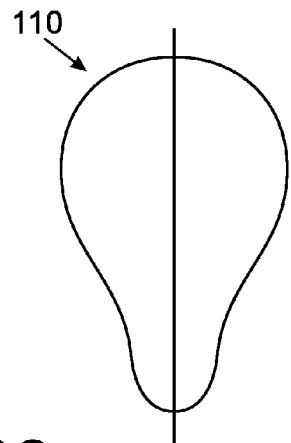
Figure 33A  Figure 33B  Figure 33C  Figure 33D
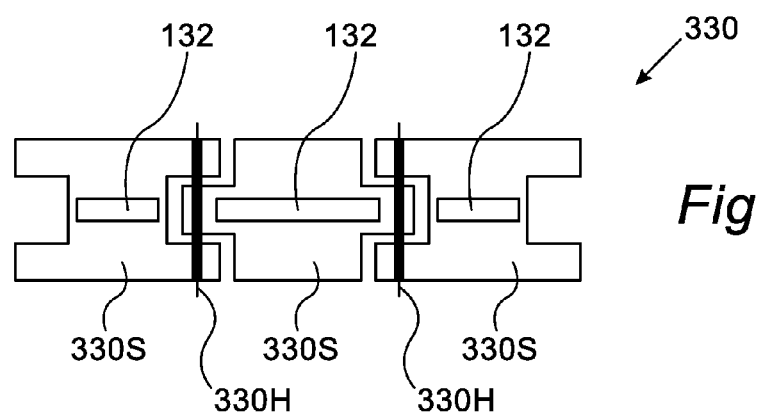
Figure 34A
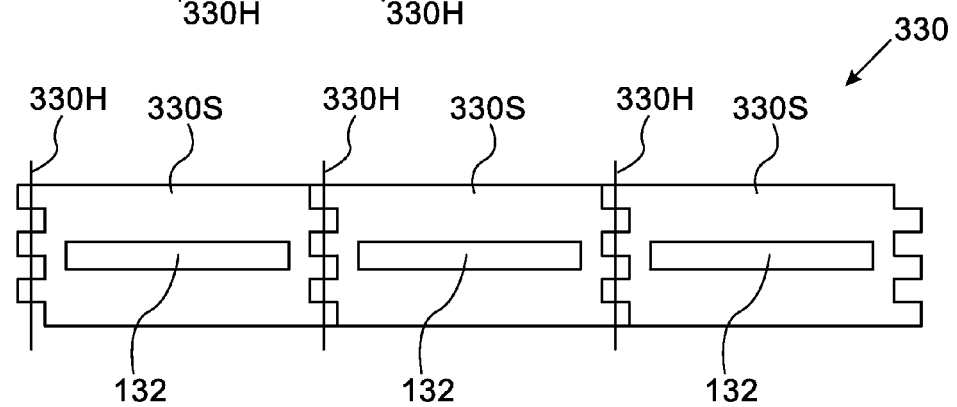
Figure 34B

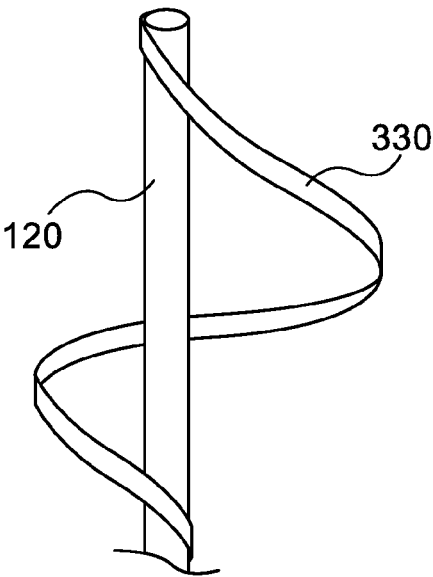
Figure 35A1        Figure 35A2
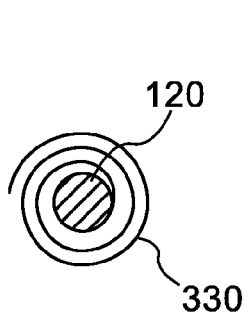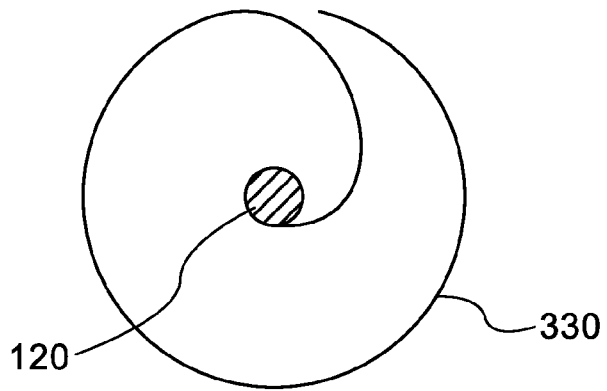
Figure 35B1        Figure 35B2

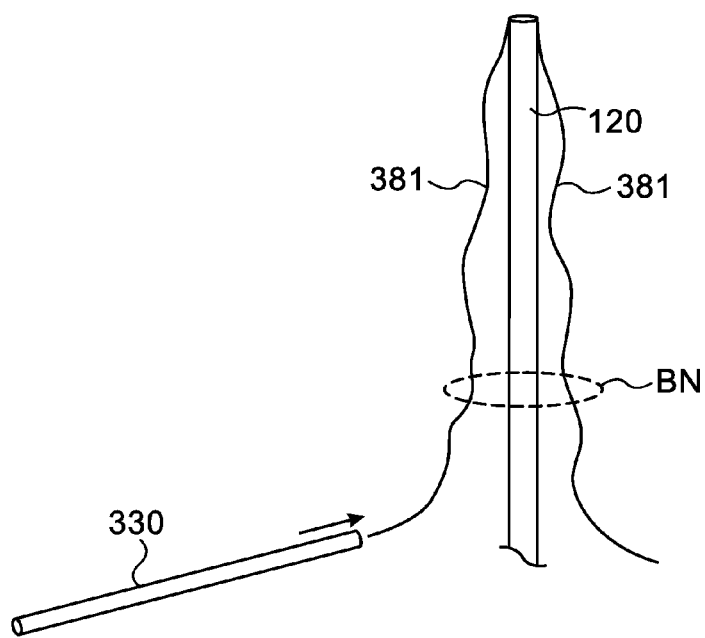
Figure 38A1
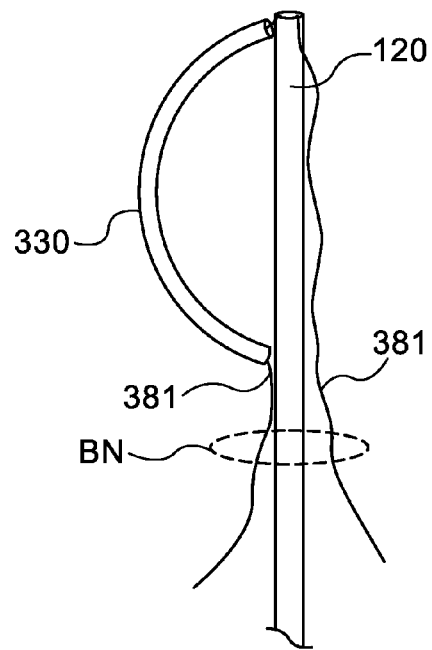
Figure 38A2

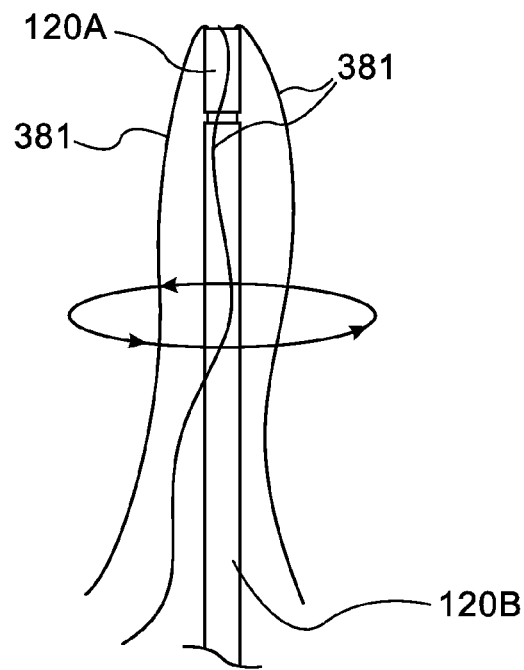
Figure 38B1
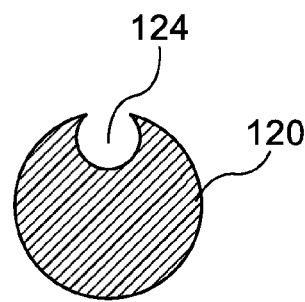
Figure 38B2

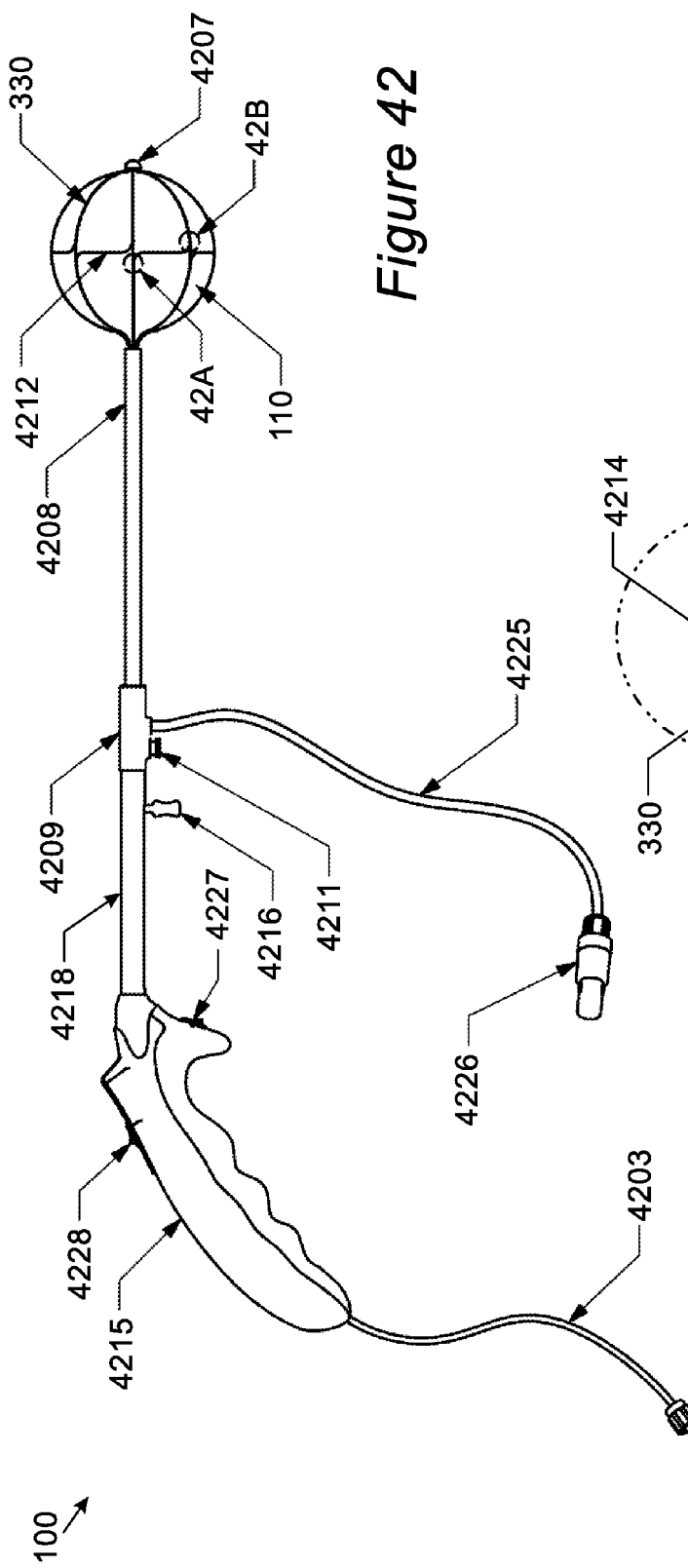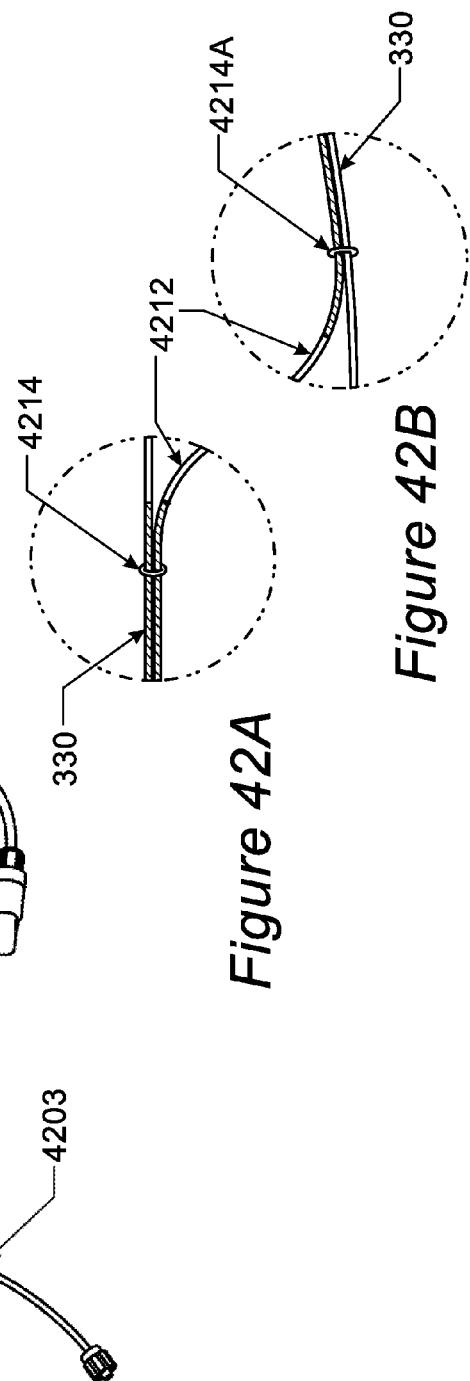

BLADDER TISSUE MODIFICATION FOR OVERACTIVE BLADDER DISORDERS

CROSS-REFERENCE

This application is a continuation of U.S. patent application Ser. No. 14/519,933, filed Oct. 21, 2014, which is a continuation-in-part application of PCT Application Serial No. PCT/IB2013/001203, filed Apr. 19, 2013, to which priority was claimed under 35 U.S.C. §120, and which claims the benefit of U.S. Provisional Application Nos. 61/636,686, filed Apr. 22, 2012, and 61/649,334, filed May 20, 2012, and which also claims the benefit of U.S. Provisional Applications Nos. 61/908,748, filed Nov. 26, 2013, and 61/972,441, filed Mar. 31, 2014, the disclosures of which are fully incorporated herein by reference.

BACKGROUND OF THE INVENTION

1. Background

The present invention relates to medical devices and methods. More specifically, the present invention relates to systems, devices, methods, and techniques for treating conditions of hollow organs in general. The relief of symptoms caused by overactive urinary bladder is discussed in particular.

Tissue ablation is a known technique for the treatment of various bodily disorders. Currently, ablation is used to eliminate pathological tissue (such as ablation of tumors or skin lesions), to remodel physical structures of tissue (such as in ablation of hypertrophied prostate to alleviate obstruction of urine, or ablation of pharyngeal tissue to alleviate snoring), to eliminate hyperactive normal tissue (renal nerve denervation to reduce blood pressure, uterine ablation to reduce menstrual bleeding), and to modify the electrical conductivity of tissue (such as in treating cardiac arrhythmia). Tissue ablation is often used to treat cardiac rhythm disorders in particular, especially atrial fibrillation. The methods and devices for performing such procedures in a beating heart are documented and described in the art. Many ablation procedures, however, are lengthy, demand visualization, imaging and/or localization, and are typically performed in specialized labs at significant costs. While using ablation of cardiac tissue to modify tissue conductivity within an organ in order to relieve arrhythmia has been known for years, this treatment modality is applied to cardiac tissue out of the belief that only excitable and conductive tissue, such as cardiac tissue can be treated in this way.

Overactive bladder is typically caused by urinary muscle spasms that cause an urgency, often an unstoppable urgency, to urinate. Overactive bladder is common in older adults and is estimated to affect more than one in ten adults in the United States. Current treatments for overactive bladder include bladder training, pelvic floor exercises, and anticholinergics or similar drugs for more difficult cases. Anticholinergics can block the nerve signals related to bladder muscle contraction and can even increase bladder capacity. The use of anticholinergics, however, can result in many side effects such as dry mouth, constipation, blurred vision, and increased heart rate. Therefore, anticholinergics are not often recommended for patients with glaucoma, urinary retention, or gastrointestinal problems. Other drug classes may be applied to relax bladder muscles but are often associated with undesirable side effects as well. In extreme cases, surgical procedures are used. These surgical procedures include bladder augmentation, the surgical enlargement of the bladder by addition of intestinal tissue to the bladder tissue, and the implantation of a sacral nerve root stimulator. Such surgical procedures, however, are highly invasive and can involve the permanent implantation of a device which can lead to many related complications.

Thus, improved devices and methods for treatment of urinary disorders are desired. These improved device and methods may be specifically designed to treat symptoms and disorders, including overactive urinary bladder, not traditionally treated with ablation or similar procedures, desirably without the side effects and complications that commonly occur with the use of current drugs and devices.

2. References of Interest

The following U.S. Patents, U.S. Patent Publications, and PCT Publications may be of interest: U.S. Pat. Nos. 8,137,342, 8,007,496, 7,892,229, 7,850,681, 7,846,153, 7,837,720, 7,813,313, 7,744,594, 7,761,169, 7,655,006, 7,655,005, 7,632,268, 7,648,497, 7,625,368, 7,556,628, 7,527,622, 7,507,234, 7,500,973, 7,410,486, 7,381,208, 7,371,231, 7,326,235, 7,357,796, 7,300,433, 7,288,089, 7,288,087, 7,278,994, 7,278,991, 7,220,257, 7,195,625, 7,192,438, 7,101,387, 7,101,368, 7,083,614, 7,081,112, 7,074,233, 7,060,062, 7,022,120, 7,001,378, 6,997,924, 6,875,209, 6,740,108, 6,692,490, 6,629,535, RE038229, 6,496,737, 6,458,098, 6,353,751, 6,283,989, 6,223,085, 6,161,049, 6,097,985, 6,083,255, 6,053,937, 6,024,743, 6,001,093, 5,992,419, 5,989,284, 5,902,251, 5,827,273, 5,800,486, 5,649,973, 5,599,294, 5,578,008, 5,509,929, 5,480,417, 5,470,352, 5,405,346, 5,380,319, 5,188,602, 5,150,717, 5,106,360, 5,057,106, 5,056,531, 4,808,164; U.S. Pub. Nos. 2013/0066308, 2013/0018281, 2012/0143179, 2012/0130363, 2012/0116384, 2012/0101490, 2012/0071873, 2012/0071870, 2012/0065636, 2012/0059368, 2012/0029500, 2012/0022520, 2012/0016358, 2012/0004656, 2012/0004654, 2011/0319880, 2011/0306904, 2011/0301662, 2011/0264086, 2011/0264085, 2011/0257647, 2011/0166570, 2011/0152855, 2011/0152839, 2011/0118719, 2011/0112432, 2011/0098694, 2011/0034976, 2011/0028886, 2011/0082450, 2010/0114087, 2010/0305562, 2010/0030204, 2010/0286753, 2010/0286688, 2010/0280510, 2010/0234840, 2010/0198066, 2010/0179530, 2010/0168734, 2010/0160906, 2010/0114087, 2010/0076425, 2010/0076402, 2010/0049192, 2010/0049186, 2010/0049182, 2010/0049031, 2010/0004650, 2009/0318914, 2009/0306644, 2009/0281532, 2009/0248012, 2009/0163906, 2009/0131928, 2009/0076494, 2009/0018533, 2008/0312642, 2008/0262489, 2008/0249518, 2008/0223380, 2008/0172050, 2008/0140070, 2008/0140067, 2008/0125765, 2008/0097427, 2008/0077174, 2008/0004613, 2007/0293854, 2007/0282184, 2007/0129725, 2007/0088247, 2007/0078451, 2007/0066973, 2007/0049918, 2007/0038203, 2007/0005050, 2006/0259029, 2006/0253178, 2006/0253113, 2006/0167442, 2006/0118127, 2006/0009758, 2005/0251125, 2005/0228370, 2005/0165389, 2005/0131500, 2005/0124843, 2005/0107783, 2005/0096647, 2004/0243199, 2004/0186468, 2004/0172112, 2004/0147915, 2004/0133254, 2003/0069619, 2003/0060813, 2003/0060762, 2003/0055470, 2002/0183735, 2001/0014805; and WO2005/067791.

SUMMARY OF THE INVENTION

It is the inventors' belief that by applying controlled ablation in the urinary bladder, conductivity within the organ can be modified so as to treat urinary disorders. Accordingly, systems, devices, and methods for treating a hollow bodily organ, particularly a urinary bladder for overactive bladder, are disclosed. In many embodiments, a predetermined pattern of tissue regions having reduced electrical propagation is created. These regions of reduced electrical propagation will typically affect the electrical and/or mechanical properties of the bladder to treat overactive bladder, for example, by reducing the occurrence of the undesirable muscle spasms that cause the disorder.

An aspect of the invention provides a method of treating a urinary disorder in a bladder. A predetermined pattern of tissue regions having reduced electrical propagation is created in an inner wall of the bladder. Creating these tissue regions with reduced electrical propagation modifies at least one of a mechanical or an electrical property of the bladder.

The predetermined pattern of tissue regions having reduced electrical propagation can have a variety of therapeutic functions. The tissue regions having reduced electrical propagation can achieve at least one of preventing, attenuating, or slowing dissemination of electrical activity within bladder tissue. Additionally or alternatively, the tissue regions having reduced electrical propagation can achieve at least one of preventing, attenuating, or modifying the transfer of mechanical forces through the bladder. The tissue regions having reduced electrical propagation can also decrease bladder smooth muscle contraction caused by aberrant electrical activity. Any one or more of these therapeutic functions can reduce or prevent symptoms of overactive bladder or other bladder conditions.

The predetermined patterns of tissue regions having reduced electrical propagation can have a variety of configurations. The tissue regions may be arranged to have a long axis parallel to a long axis of the bladder when full. The tissue regions may be arranged to have a long axis transverse to a long axis of the bladder when full. The tissue regions may comprise a plurality of distinct tissue spots having reduced electrical propagation distributed throughout the inner wall of the bladder. The tissue regions may be selected to electrically isolate one or more anatomical regions in the bladder such as the ureteral orifice, the uretero vesical junction, the trigone area, the bladder dome, or the bladder outlet. The tissue regions having reduced electrical propagation will typically have a depth sufficient to attenuate, slow, or even block electrical propagation through the tissue. For example, the tissue regions having reduced electrical propagation can extend through the urothelium, through the urothelium and the suburothelium, through the urothelium and suburothelium and at least a part of the detrusor, or through an entire wall of the bladder, i.e., be transmural.

In many cases, the predetermined pattern of tissue regions having reduced electrical propagation may comprise a plurality of tissue lines having reduced electrical propagation. These tissue lines may provide partial or complete barriers to electrical propagation from the ablated tissue regions to adjacent tissue regions. These tissue lines may come in a variety of configurations, including circumferential lines, longitudinal lines, parallel lines, crossing lines, straight lines, serpentine lines, continuous lines, zig-zag lines, and broken lines. The tissue lines may have a width in a range from 1 mm to 10 mm and be separated from one another by a distance in a range from 10 mm to 150 mm. The tissue lines may be arranged such that contact between the issue lines is minimized when the bladder is collapsed. The tissue lines may be arranged to avoid one or more anatomical regions selected from a group comprising the ureteral orifice, the uretero vesical junction, the trigone area, the bladder dome, or the bladder outlet.

In many cases, foci of aberrant electrical activity in the bladder are first located before the predetermined pattern of tissue regions having reduced electrical propagation is created. The predetermined pattern of regions having reduced electrical propagation will then correspond to the located foci of aberrant electrical activity. The foci of aberrant electrical activity in the bladder may be located in many ways, for example, by imaging or visualizing induced contraction of the bladder or by mapping electrical activity in the bladder with a plurality of electrodes of a device introduced into the bladder cavity. The same device may in some cases be used both for mapping the electrical propagation patterns prior to (and in some cases after) treatment and to create the predetermined pattern of tissue regions having reduced electrical propagation. At least a portion of the mapping (and optionally treatment) device introduced into the bladder cavity may be configured to conform to the shape of the inner wall of the bladder.

The predetermined pattern of tissue regions having reduced electrical propagation may be created in many different ways. The tissue regions may be created by at least one of RF ablation, cryoablation, photoablation, microwave energy, use of a chemical agent, ultrasound energy, and mechanical scoring. The predetermined pattern of tissue regions having reduced electrical propagation can be created by placing a tissue modification structure of a device introduced into the bladder cavity at or near a target site in the inner wall of the bladder and moving one or more active elements of the tissue modification structure in a predetermined manner. For example, at least a portion of the active element may be rotated within the bladder to create a continuous tissue region having reduced electrical propagation. The active element may also be moved in other ways such as by translation along the longitudinal axis of the bladder or transverse to the axis. At least a portion of the tissue modification structure near the active element may be configured to conform to the shape of the inner bladder wall. The predetermined pattern of tissue regions having reduced electrical propagation can also be created by placing a plurality of tissue modification structures of a device introduced into the bladder cavity at or near a plurality of target sites in the inner wall of the bladder and applying energy through a plurality of active elements of the tissue modification structures. Energy may be applied by the plurality of active elements simultaneously, selectively, or sequentially. Energy may be applied by the active elements without having to reposition the plurality of tissue modification structures after they have been placed at or near the plurality of tissue sites. Often, the plurality of tissue modification elements is configured to conform to the shape of the bladder cavity. The predetermined pattern of tissue regions having reduced electrical propogation may be created under visualization, including direct visualization of the interior of the bladder through a cystoscope or an ureteroscope. Alternatively visualization can be performed using a video camera, optic fiber, or other means which may be part of the device or be inserted through the at least a portion of the device.

Another aspect of the invention provides a device for treating a urinary disorder in a bladder. The device comprises a shaft, a tissue modification structure, and means for creating a predetermined pattern of tissue regions having reduced electrical propagation in the inner wall of the bladder to modify at least one of a mechanical or an electrical property of the bladder. The shaft is typically advancable through a urethra of a patient to reach the bladder but in other embodiments could be configured to be advanced laparoscopically or by other minimally invasive procedures through a patient's abdominal wall. The tissue modification structure is coupled to a distal end of the shaft. At least a portion of the tissue modification structure is adapted to contact and conform to at least a portion of an inner wall of the bladder. The means for creating the predetermined pattern of tissue regions having reduced electrical propagation can be configured so that the modified tissue regions created will typically have a depth sufficient to attenuate, slow, or even block electrical propagation through the tissue. For example, the modified tissue regions may extend through the urothelium, through the urothelium and the suburothelium, the urothelium and suburothelium and at least a part of the detrusor, or through an entire thickness of the wall of the bladder. Alternatively, the tissue region treated includes the suburothelium and some of the detrusor muscle, sparing the urothelium (also known as a "skip lesion").

The means for creating the predetermined pattern of tissue regions having reduced electrical propagation can be configured so that the predetermined pattern of tissue regions have a variety of therapeutic functions and configurations. Creating these tissue regions can achieve at least one of preventing, attenuating, or slowing dissemination of electrical activity within bladder tissue. Alternatively or in combination, creating these tissue regions can achieve at least one of preventing, attenuating, or modifying the transfer of mechanical forces through the bladder. The tissue regions can decrease bladder smooth muscle contraction caused by aberrant electrical activity.

It may be understood that the treated areas can have other altered biological activities, including altered paracrine activity, altered membrane potential, altered excitability, altered response to neural or chemical activation, altered stretch responses, and/or altered electrical conductivity.

The means for creating the predetermined pattern of tissue regions having reduced electrical propagation can be configured to create a plurality of tissue lines having reduced electrical propagation. The plurality of tissue lines having reduced electrical propagation can comprise at least one of circumferential lines, longitudinal lines, parallel lines, crossing lines, straight lines, serpentine lines, continuous lines, zig-zag lines, and broken lines. The tissue lines may have a width in a range from 1 mm to 10 mm and be separated from one another by a distance in a range from 10 mm to 150 mm. The tissue lines may be arranged such that contact between the tissue lines is minimized when the bladder is collapsed. The tissue lines can be arranged to avoid one or more anatomical regions selected from a group comprising the ureteral orifice, the uretero vesical junction, the trigone area, the bladder dome, or the bladder outlet. The means for creating the predetermined pattern of tissue regions having reduced electrical propagation can be configured to create a plurality of tissue spots having reduced electrical propagation distributed throughout the inner wall of the bladder.

The bladder wall contact element will typically comprise a cage, such as a wire cage or malecot-like component, shaped to conform to the inner wall of the bladder. The cage may comprise one or more mapping electrodes for locating foci of aberrant electrical activity in the bladder. The predetermined pattern of tissue regions having reduced electrical propagation may correspond to the located foci of aberrant electrical activity in the bladder. The cage may also carry one or more active elements for reducing electrical propagation in tissue. The one or more active elements may be adapted to create the pattern of electrically isolated areas by at least one of RF ablation, cryoablation, photoablation, microwave energy, use of a chemical agent, ultrasound energy, and mechanical scoring. The cage may be moveable within the bladder to move the one or more active elements to create the predetermined pattern. The one or more active elements may be adapted to deliver energy to the inner wall of the bladder simultaneously, sequentially, or selectively.

The bladder wall contact element may comprise an elongate curved element shaped to conform to at least a portion of the inner wall of the bladder. The curved element may be electrically coupled to a power generator at a plurality of points along the elongate curved element. The means for creating the predetermined pattern of electrically isolated areas may comprise one or more active elements disposed on the elongate curved element. The one or more active elements may be adapted to create the pattern of electrically isolated areas by at least one of RF ablation, cryoablation, photoablation, microwave energy, use of a chemical agent, ultrasound energy, and mechanical scoring. The elongate curved element may be movable to move the one or more active elements to create the predetermined pattern.

The device may further comprise an expandable element coupled with the bladder wall contact element. The expandable element is expandable to press the tissue modification structure against the inner wall of the bladder.

A further aspect of the invention provides a system for treating a urinary disorder in a bladder. The system comprises the aforementioned device and a means for visualizing the bladder as the predetermined pattern of electrically isolated areas is created in the bladder. The means for visualizing the bladder may comprise a cystoscope or an ureteroscope, or other visualization means which may be part of the device or is inserted through the at least a portion of the device.

While many embodiments disclosed herein are described as related to or configured for the treatment of a bladder for overactive bladder, the devices and methods described herein may also find use for other hollow bodily organs. Accordingly, yet another aspect of the invention provides a method of treating a disorder in a hollow bodily organ. A predetermined pattern of tissue regions having reduced electrical propagation is created in an inner wall of the hollow bodily organ to modify at least one of a mechanical or an electrical property of the organ. The hollow bodily organ may comprise a bladder, a bronchus, a bronichiole of the lung, a stomach, a colon, a large intestine, a small intestine, a kidney, a vagina, a uterus, a fallopian tube, an esophagus, a gall bladder, and the like. The reduced electrical propagation regions can be applied to reduce bladder over-activity when applied to bladder, bronchial hyper-reactivity (asthma) when applied to bronchus or bronchiole, gastric peristaltic motions when applied to stomach, irritable bowls (as in irritable bowel syndrome) when applied to colon or intestines, reflex fluid retention when applied to kidney, vaginismus when applied to vagina, pre-term contractions, or irritable uterus, when applied to uterus or fallopian tube, and esophageal spasm and/or gastroesophageal reflux disease when applied to the esophagus.

A yet further aspect of the invention provides a device for treating a disorder in a hollow bodily organ. The device comprises a shaft advancable through a bodily passage of a patient to reach the hollow bodily organ, a tissue modification structure coupled to a distal end of the shaft, and means for creating a predetermined pattern of tissue regions having reduced electrical propagation in the inner wall of the hollow bodily organ to modify at least one of a mechanical or an electrical property of the hollow bodily organ. At least a portion of the tissue modification structure is adapted to contact and conform to at least a portion of an inner wall of the hollow bodily organ. The hollow bodily organ to be treated is selected from the group comprising a bladder, a bronchus, a bronichiole of the lung, a stomach, a colon, a large intestine, a small intestine, a kidney, a vagina, a uterus, a fallopian tube, an esophagus, a gall bladder, and the like.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 1 is a cut-away view of an ablation device adapted for insertion through the human urethra, according to many embodiments;

FIG. 2 is a perspective view of a longitudinal electrode arrangement for the device of FIG. 1, according to many embodiments;

FIG. 3 is a perspective view of a circumferential electrode arrangement for the device of FIG. 1, according to many embodiments;

FIG. 33A, FIG. 33B, FIG. 33C, and FIG. 33D show side views of an ablation device with a variable compliance expandable element at various stages of expansion, according to many embodiments;

FIG. 34A and FIG. 34B show top views of hinged struts of an ablation device, according to many embodiments;

FIG. 35A1 and FIG. 35A2 show side views of a three dimensional helical or spiral strut coiled around a shaft of an ablation device, according to many embodiments;

FIG. 35B1 and FIG. 35B2 show top views of the three dimensional helical or spiral strut coiled around the shaft of the ablation device, according to many embodiments;

FIG. 38A1, FIG. 38A2, FIG. 38B1, and FIG. 38B2 show side views of an ablation device with struts that can be separately advanced into a urinary bladder, according to many embodiments;

FIG. 42, FIG. 42A, FIG. 42B, FIG. 42C, FIG. 42D, FIG. 42E, and FIG. 42F show side views of a low profile, sliding wire based ablation device comprising both longitudinal and circumferential electrodes from its proximal end to its distal end, according to many embodiments;

DETAILED DESCRIPTION OF THE INVENTION

Figure 4:
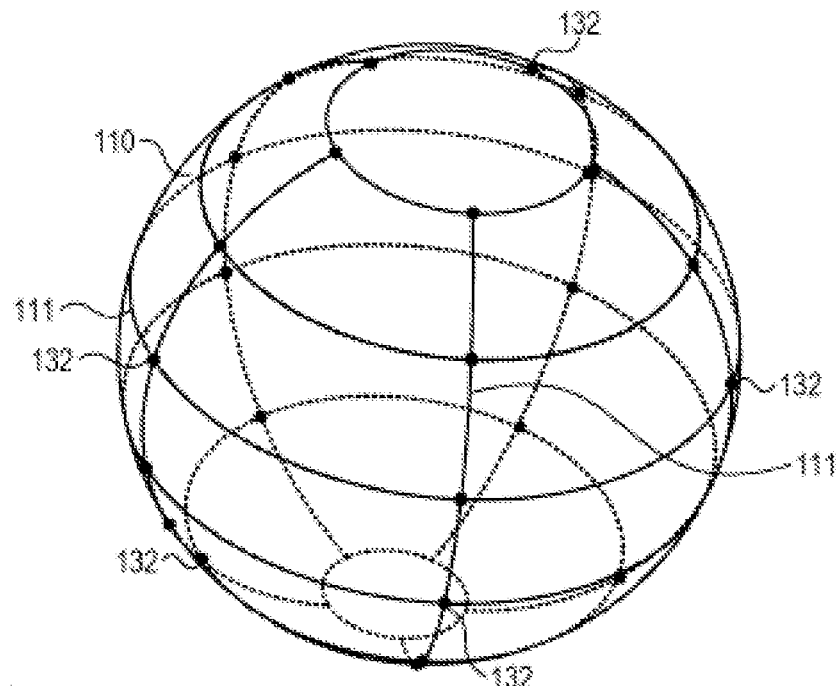
FIG. 4 is a perspective view of an electrode arrangement to produce a pattern of distributed spots for the device of FIG. 1, according to many embodiments.

Systems, devices, and methods for treating a hollow bodily organ, particularly a urinary bladder for overactive bladder, are disclosed.

Method and devices for tissue ablation in hollow organs are described. In some embodiments, the devices described herein are used to destroy unwanted tissue, such as overgrown uterus mucosa, or hypertrophic gastric mucosa. In many embodiments, tissue ablation regions are created within the treated organ, thus preventing, attenuating, or slowing dissemination of the electrical activity within the tissue. These regions will typically be in the form of lines. Such lines or regions of reduced electrical conductivity or propagation may be described as electrical isolation lines or regions, although complete electrical isolation may not always be achieved or desired. In many embodiments, creating tissue ablation lines or regions are within the treated organ can prevent, attenuate, or modify the transfer of mechanical forces through the organ. In some embodiments, ablation lines or regions disperse mechanical forces more evenly, effectively preventing certain cells or tissue regions from being extremely stretched. In some embodiments, the lines and the resulting scarring are induced in a hollow organ, such as a bronchiole or a urethra, to prevent pathological contraction of the organ.

In many embodiments, the electrical isolation regions or regions of reduced electrical propagation are created in a human urinary bladder. The creation of such lines or regions can decrease bladder smooth muscle contraction caused by aberrant electrical activity in the bladder wall, alleviating the symptoms associated with overactive bladder, detrusor-sphincter dyssynergia, urinary incontinence, bladder pain syndrome, and/or prostatism. The creation of such lines may increase the threshold for generalized activity of the organ, thus making sure that only events driven by potent and coordinated neural activity will cause generalized organ activity. This feature can be useful in cases of detrusor-sphincter dyssynergia, by elevating the threshold for generalized bladder contractions, and limiting those contractions to situations of generalized and coordinated neural activity (this will also relax the sphincter).

The electrical isolation regions or regions of reduced electrical propagation can also be created in other hollow bodily organs.

The electrical isolation regions or regions of reduced electrical propagation can be created within a human bronchial tree, to prevent synchronized and generalized bronchial constriction, such as those occurring in an asthmatic attack. In some embodiments, the ablation lines are created in a bronchiole to isolate some alveolar spaces from the rest of the bronchial tree.

The electrical isolation regions or regions of reduced electrical propagation can be created in a human uterus to prevent unwanted uterus contractions that might disturb the normal course of a pregnancy.

The electrical isolation regions or regions of reduced electrical propagation can be created within a human stomach to slow gastric emptying and reduce the weight of the subject.

The electrical isolation regions or regions of reduced electrical propagation can be created within a human colon to alleviate symptoms of erratic GI activity such as irritable bowel syndrome.

FIG. 1 is a schematic of a device 100 adapted for insertion through the human urethra according to embodiments of the invention. The device 100 comprises an inflatable balloon 110 and a flexible shaft 120 coupled to the balloon 110. The balloon 110 may be collapsed to reduce the profile of the device 100. The flexible shaft 120 can have sufficient stiffness so that the device 100 can be advanced through the human urethra when in reduced profile. The flexible shaft 120 comprises a urine lumen 122 and an inflation lumen 126. The urine lumen 122 is open at a distal port 124 near the proximal end of the balloon 110 to collect urine within the bladder and divert it out. The inflation lumen 126 is open at a port 128 within the balloon 110 to deflate or inflate the balloon 110. The device 100 further comprises an electrical lead 130 leading to and powering one or more electrodes 132 disposed on the surface of the balloon 110. The balloon 110 may be configured to conform to the shape of the bladder when the balloon 110 is expanded. The balloon 110 may be pre-shaped to be oval and somewhat curved anteriorly. When the balloon 110 is expanded, the one or more electrodes 132 will typically contact the inner wall of the bladder. The one or more electrodes 132 can be used to ablate the inner wall of the bladder and in some cases to also electrically map the bladder. The one or more electrodes 132 may be arranged on the outer wall of the balloon 110 in a predetermined ablation pattern. The ablated tissue regions in the inner wall of the hollow organ may have reduced electrical propagation.

In many embodiments, the ablation device described herein, including the device 100, may be used to ablate localized areas of tissue that express aberrant electrical activity or have other undesirable characteristics. For example, foci of aberrant electrical activity in the urinary bladder may be identified by recording or mapping from electrodes 132 located in the outer wall of the balloon 110. This may be followed by ablation of the identified foci by the same electrodes 132 or via other means. The electrodes 132 may be energized selectively to create a desired ablation pattern based on the identified foci of aberrant electrical activity. For example, embodiments of the invention may provide a system for ablating a hollow bodily organ such as the bladder, the system comprising the device 100 and a processor coupled to the device 100. The processor may be configured to run code to cause the device 100 to electrically map the bladder when placed therein, to further determine a predetermined ablation pattern based on the mapped electrical activity, and to further operate the device 100 to selectively energize the electrodes 132 to create the ablation pattern on the inner wall of the bladder. Other means may be provided to create the desired ablation pattern determined by the mapping electrodes 132.

The foci of aberrant electrical activity may also be identified by other means. In some embodiments, the foci are identified by an urodynamic study involving bladder contraction that is coupled to an imaging study (ultrasound, dynamic CT, etc.) visualizing the contraction of the bladder. In these embodiments, the zones that lead the contraction (i.e., tissue regions that contract before the rest of the bladder or more than the rest of the bladder) will be the preferred site for ablation. In other embodiments, an ultrasound study of the bladder is conducted to identify anatomical characteristics that may be preferred ablation sites. In some embodiments, wall thickening areas are targeted.

In some embodiments, residual volume is maintained in the bladder after the ablation for a period of at least 3 hours, to avoid adhesions.

Referring back to FIG. 1, the electrodes 132 disposed over the outer wall of the balloon 110 may be configured to ablate the inner wall of a hollow bodily organ such as the bladder to create a variety of patterns. The lines of ablation may be circumferential or longitudinal, parallel or crossing, straight or serpentine, continuous, or broken.

FIG. 2 shows an electrode arrangement wherein the electrodes 132 are arranged longitudinally on the balloon 110 to contact the inner wall of the hollow target organ so as to be able to create longitudinal ablation lines within a hollow target organ such as the bladder. Longitudinal ablation lines can allow for uninterrupted conduction from the bladder dome downwards while interrupting conduction from one bladder meridian to others. As shown in FIG. 2, the longitudinally arranged electrodes 132 do not intersect with one another but may intersect with one another in other embodiments. Such intersecting ablation lines may serve to electrically isolate selected zones of tissue, for example an anatomic structure such as the ureteral orifice, ureterovesical junction, the trigone area, the bladder dome, or the bladder outlet.

FIG. 3 shows an electrode arrangement wherein the electrodes 132 are arranged circumferentially on the balloon 110 so as to contact the inner wall of the hollow target organ to create continuous circumferential ablation lines within a hollow target organ such as the bladder. As shown in FIG. 3, the circumferentially arranged electrodes 132 do not intersect with one another but may intersect with one another in some other embodiments. Such intersecting ablation lines may serve to isolate selected zones of tissue as described above.

Figure 5:
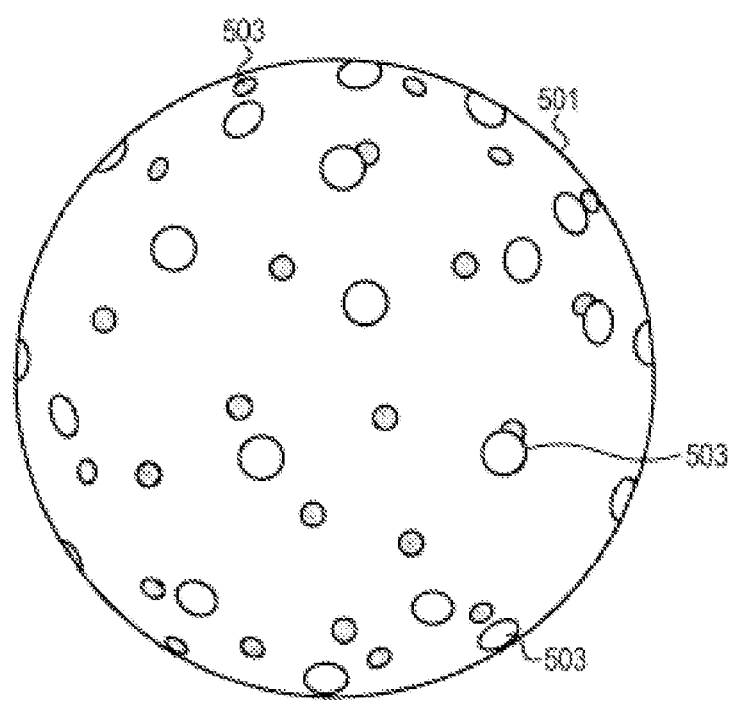
FIG. 5 is a perspective view of the inner wall of a hollow bodily organ having an ablation pattern ablated thereon by the device of FIG. 4, according to many embodiments.

FIG. 4 shows an electrode arrangement wherein the electrodes 132 are supported by a wire cage 111 disposed over the balloon 110 so that their ablating ends are distributed over the area of the wire cage 111. The electrodes 132 arranged in such a manner can create a pattern of ablated tissue spots 503 on the inner wall 501 of a hollow bodily organ such as the bladder as shown in FIG. 5. A structure similar to the wire cage 111 shown in FIG. 4 where all the wires of the cage are ablating electrodes may be used to create a crisscross pattern over the inner surface of the treated organ. In many embodiments, the electrodes 132 may be adhered onto the surface of the balloon 110. In other embodiments, the device 100 may further comprise a wire cage to support the electrodes 132.

Figure 6:
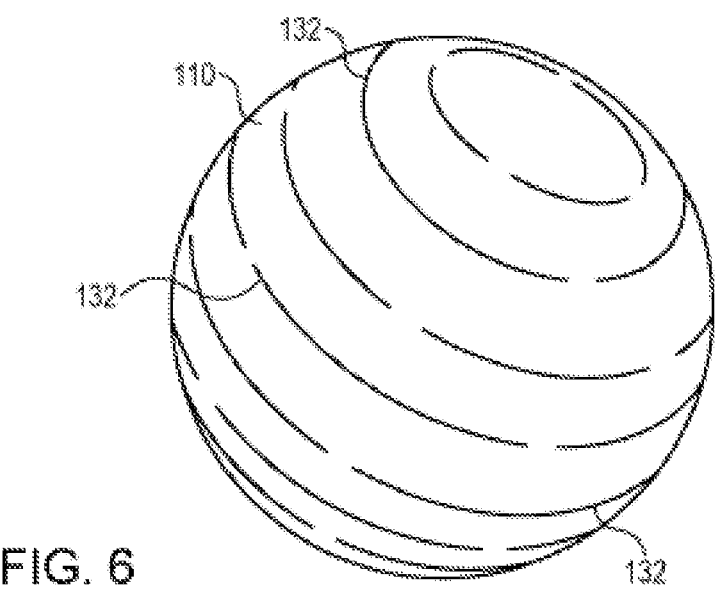
FIG. 6 is a perspective view of a non-continuous circumferential electrode arrangement for the device of FIG. 1, according to many embodiments.

FIG. 6 shows an electrode arrangement wherein the electrodes 132 are arranged circumferentially on the balloon 110 so as to contact the inner wall of the hollow target organ to create discontinuous circumferential ablation lines within a hollow target organ such as the bladder.

Figure 7:
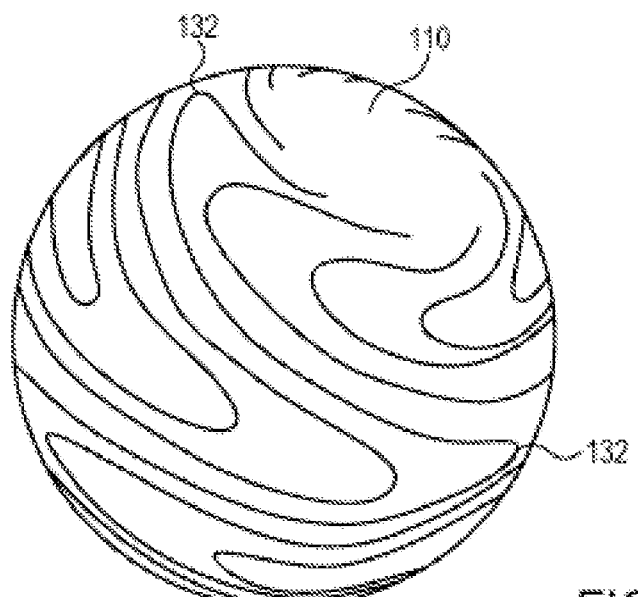
FIG. 7 is a perspective view of a serpentine electrode arrangement for the device of FIG. 1, according to many embodiments.

FIG. 7 shows an electrode arrangement wherein the electrodes 132 are arranged on the balloon 110 in a serpentine manner to contact the inner wall of the hollow target organ to create serpentine ablation lines within the hollow target organ such as the bladder.

Figure 8:
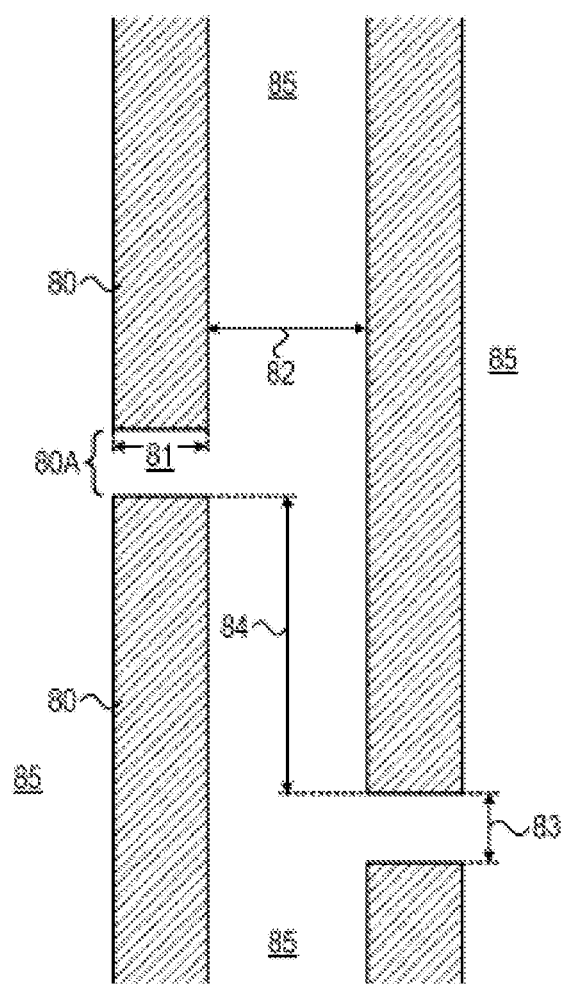
FIG. 8 is a top view of ablation lines, according to many embodiment.

FIG. 8 is a top view of ablation lines 80 that can be created by the device 100 in the inner wall 501 of a hollow bodily organ such as the bladder. The ablation lines 80 separate untreated tissue areas 85.

The ablation lines 80 and their arrangement can have a variety of attributes. The thickness 81 of the ablation lines 80 may vary from a minimum of 1 mm to a maximum of 10 mm. Very thin lines may produce incomplete electrical isolation and thus may serve to slow conduction of electrical activity across them without totally preventing its passage. This can prevent aberrant sources from causing synchronized activation of the whole organ, while allowing physiologic activity to spread through the whole organ. Thicker lines can produce complete isolation which may allow the direction of electrical activity in specific pathways, and control over the way electrical activity propagates throughout the organ. The ablation lines 80 can be created to have a depth sufficient to attenuate, slow, or even block electrical propagation through the tissue. For example, the ablation lines 80 may extend through the urothelium, through the urothelium and the suburothelium, the urothelium and suburothelium and at least a part of the detrusor, or through an entire wall of the bladder.

In many embodiments, the width 81 of the ablation line is set to allow regeneration of the transitional epithelium before significant fibrosis occurs. For example, ablation lines 80 can be approximately 3 mm wide in an empty bladder and the epithelium can be expected to regenerate within 10 days before significant fibrosis will occur.

In some embodiments, the ablation lines 80 are of varying thickness, being thicker towards the dome (cranial pole) of the bladder and thinner when nearing the bladder outlet, especially if ablation is applied when the bladder is expanded.

As shown in FIG. 8, generally parallel ablation lines 80 may be separated from each other by a distance 82 which may vary between 10 mm to 150 mm. This distance 82 will typically also be the width of the electrical conduction or propagation pathway. Axially adjacent ablation lines 80 may be separated from each other by a distance 83 which may vary between 1 mm and 20 mm. This distance 83 may serve as a bridge between parallel conduction pathways. Such bridges between parallel groups of ablation lines may be axially separated from each other by a distance 84. Like the thickness 81 of the ablation lines 80, the separation distances 82, 83 between the ablation lines 80 and the separation distance 84 between bridges may also affect the ability of electrical activity to propagate between isolated areas or strips of the organ's wall.

In some embodiments, the ablation lines 80 are configured so that contact between ablation zones is minimized, even when the organ is collapsed.

In some embodiments, the dome of the urinary bladder is spared from ablation. In some embodiments, an approximately circular area of the dome is spared, having a diameter of approximately 25 mm in the expanded bladder.

In some embodiments, short ablation lines 80 are separated from each other in an expanded bladder, and approximated to become effectively continuous only when the bladder volume is low. In these embodiments, effective bladder contractions can normally occur in the distended bladder, but not in an empty bladder.

Lines of ablated tissue 80 or tissue lines having reduced electrical propagation can be created in many ways, including the use of heat, cold, laser light, microwaves, chemicals, drugs, and more. In some embodiments, the energy applied is electromagnetic energy at radio frequency (RF) through conductive surfaces such as the electrodes 132 of device 100. In some embodiments, the energy applied is monopolar or bipolar and delivered through the conductive surfaces such as the electrodes 132 of device 100. Energy can be produced by an external device and conveyed to the tissue by the catheter device 100, for example through lead 130 as shown in FIG. 1. Typically, energy is applied only once or only once every 30 seconds or more to allow cooling of the device 100. The energy applied may be sufficient to cause a transmural lesion.

Figure 9A:
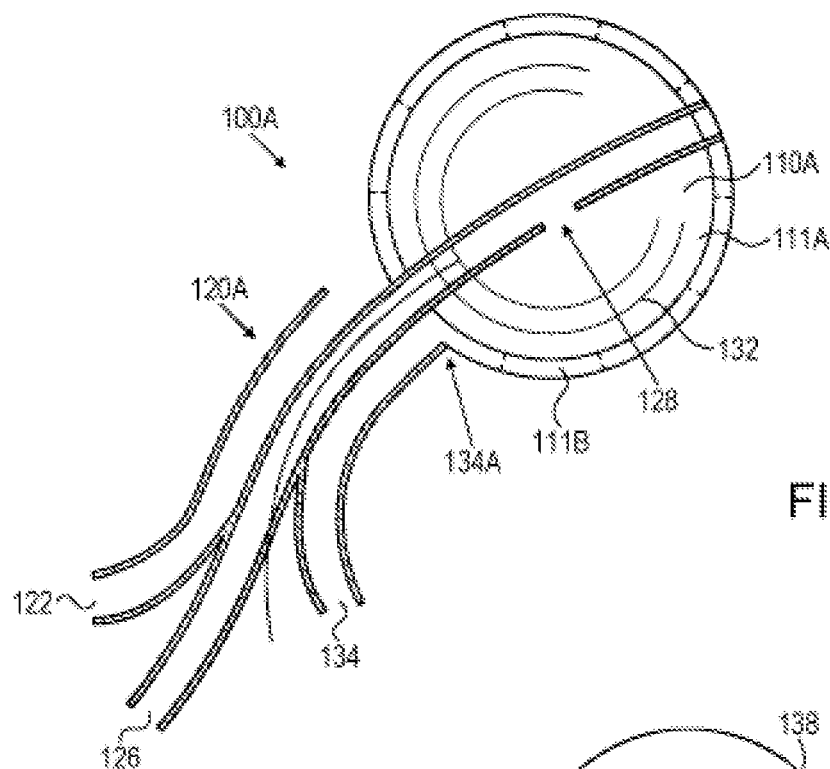
FIG. 9A is a cut-away view of an ablation device having a cooling mechanism and adapted for insertion through the human urethra, according to many embodiments.
Figure 9B:
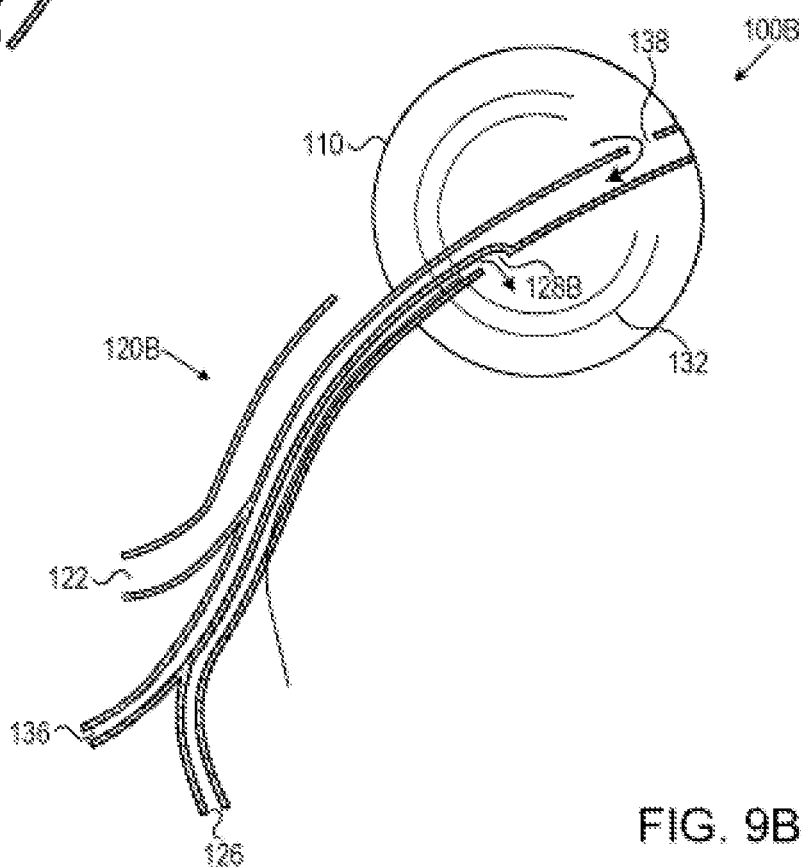
FIG. 9B is a cut-away view of another ablation device having a cooling mechanism and adapted for insertion through the human urethra, according to many embodiments.

The delivery of energy, particularly electromagnetic and RF energy, typically produces heat. Accordingly, the energy delivery device may need to be cooled to avoid inadvertent damage to the tissue of the organ wall. Also, cooling may protect the device from damage or malfunction. FIG. 9A shows an embodiment of an ablation device 100a which can be cooled. The ablation device 100A is generally similar to the device 100 described above. The flexible shaft 120A of the ablation device 100A further comprises a cooling fluid lumen 134 for the introduction and removal of a cooling fluid such as cooled saline. The balloon 110A comprises an inner compartment 111A for inflation and an outer compartment 111B which can be filled with the cooling fluid to cool the balloon 110A when the electrodes 132 have heated. The inflation lumen 126 is open to the inner compartment 111A at the port 128 and the cooling fluid lumen 134 is open to the outer compartment 111B at the distal end 134A of the cooling fluid lumen. FIG. 9B shows an embodiment of an ablation device 100B which can be cooled by circulating the fluid which keeps the balloon 110 inflated. The ablation device 100B is generally similar to the device 100 described above. The flexible shaft 120B of the ablation device 100B comprises an inflation lumen 126 to inflate the balloon 110 and a suction lumen 136 to deflate the balloon. Cooled inflation fluid can be introduced into the balloon 110 through the inflation lumen 126 open at the port 128B within the balloon 110. At the same time, inflation fluid which has been warmed by the use of the electrodes 132 can be removed from the balloon 110 through the suction lumen 126 open at the port 138.

In some embodiments, the energy is transmitted to the ablation device placed within the hollow bodily organ. The device may be a metallic device and the energy may be transmitted through magnetic fields. In other embodiments, the energy is ultrasound that is reflected and focused by air channels in the device.

Figure 10:
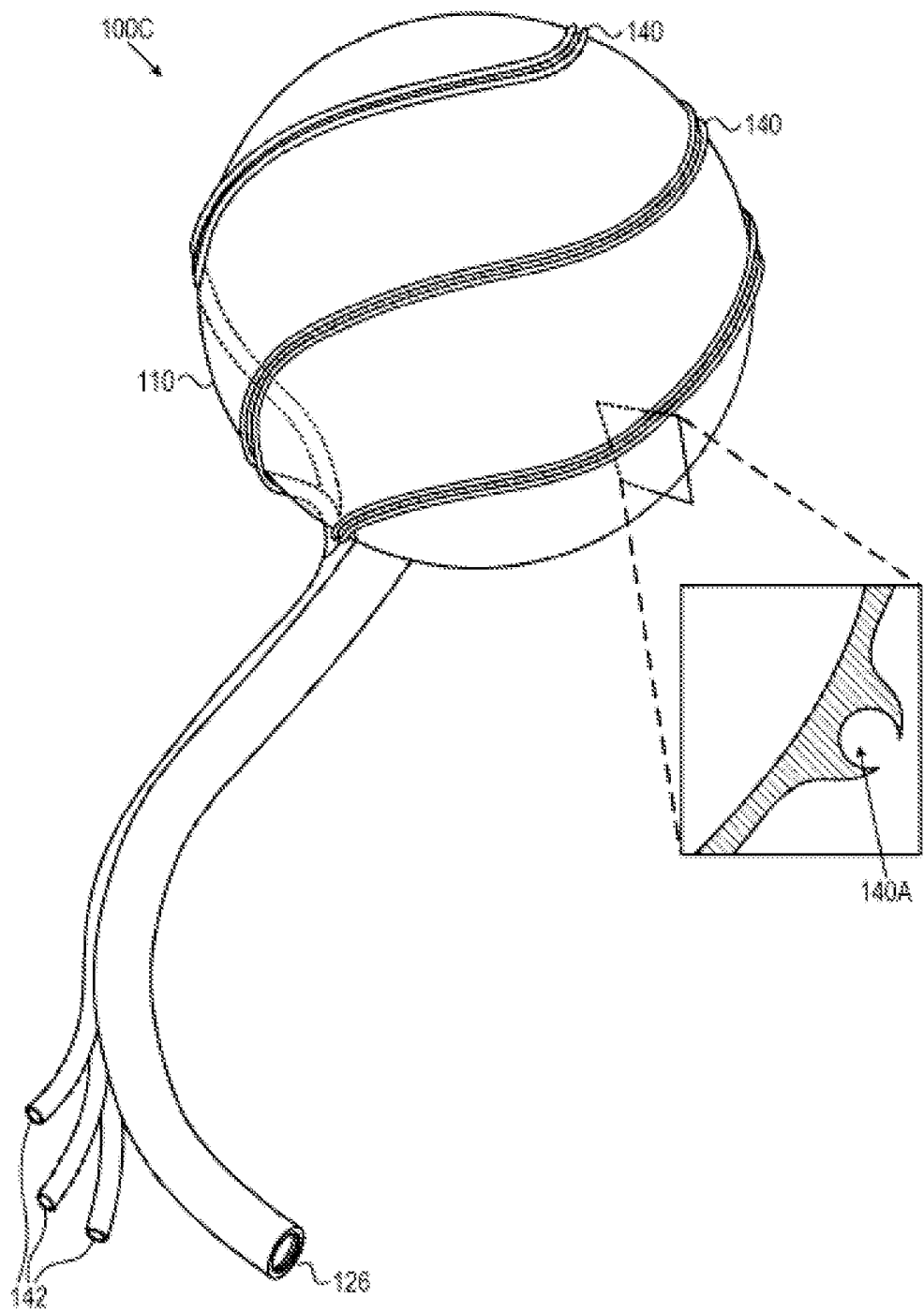
FIG. 10 is a perspective view of an ablation device comprising a plurality of exterior fluid channels and adapted for insertion through the human urethra, according to many embodiments.

FIG. 10 shows an ablation device 100C generally similar to device 100 described above. The ablation device 100C has a plurality of exterior fluid channels 140 placed on the outer surface of its inflatable balloon 100C. Fluid can be introduced into and removed from the exterior fluid channels 140 through tubes 142. When expanded within a hollow bodily organ, exterior fluid channels 140 contact points in the inner wall of the organ. In some embodiments, hot fluid and/or steam flows through the tubes 142 and the exterior fluid channels 140 to heat the contact points to a temperature that is damaging to the tissue. In some embodiments, condensed gas, such as liquid nitrogen, flows through the tubes 142 and the exterior fluid channels 140 to cool the contact points to a temperature that is damaging to the tissue. In some embodiments, the plurality of exterior fluid channels 140 are inflated to define a guidance channel 140a to guide a separate ablation catheter in specific paths on the surface of the balloon 110. The channels 140 may be closed (tube-like) or open (channel-like).

Figure 11:
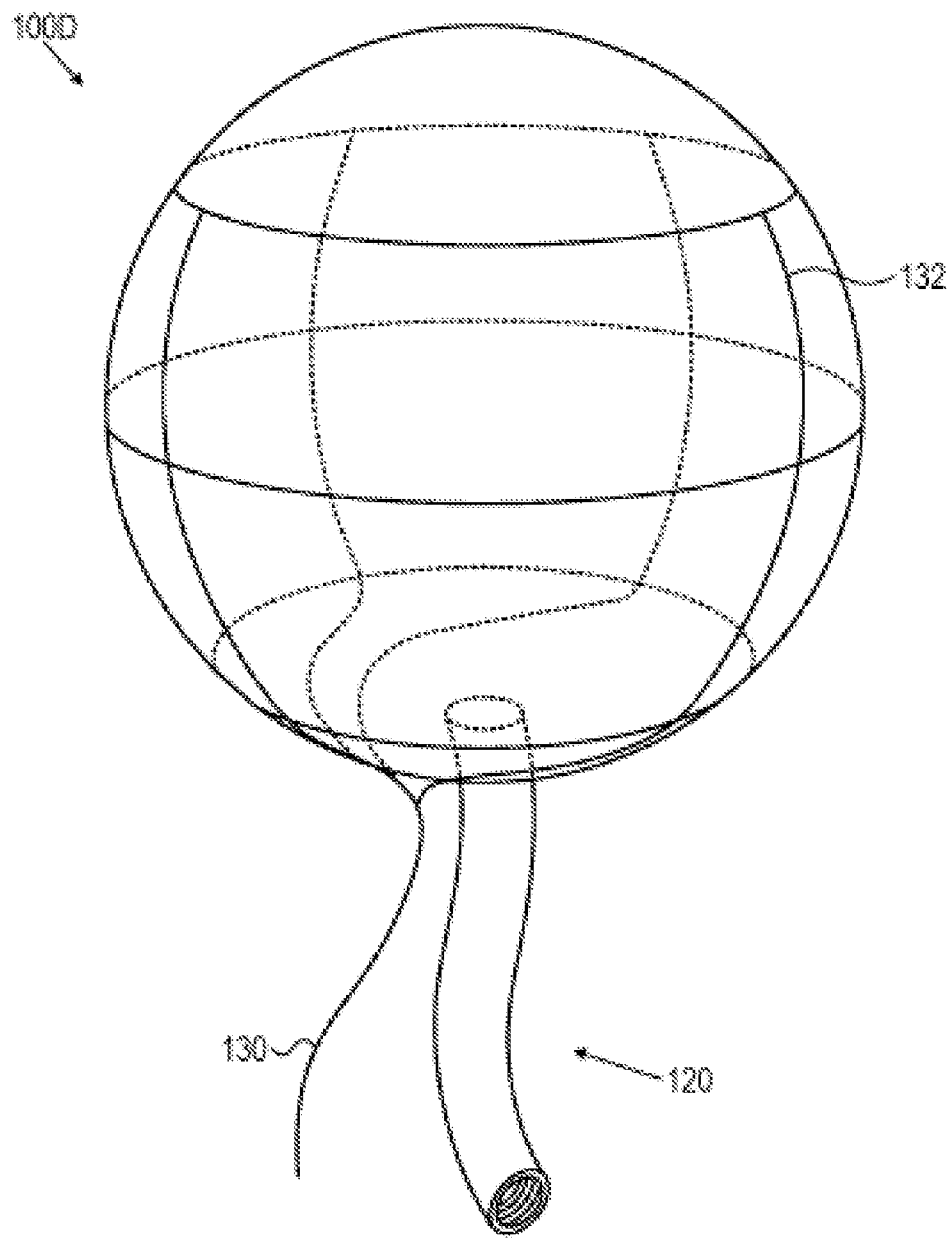
FIG. 11 is a perspective view of a parallel electrode arrangement for the device of FIG. 1, according to many embodiments.

The ablation elements such as electrodes 132 and the fluid channels 140 described above can be configured to contact the inner wall of a hollow target organ in many ways. The conductive surface of the ablation device may be shaped as a blade, with the non-insulated side coming in contact with the tissue being significantly narrower than the side contacting the device. The energy for an isolation or reduced electrical propagation line can be applied only at one or more points, and the lines may be created by rotation and/or movement of the device. The energy for an isolation or reduced electrical propagation line may be applied only at one or more lines, and ablation patterns may be created by rotation and/or movement of parts of the device. For example, as shown by FIG. 11, the contact lines may comprise multiple conductive segments or electrodes 132 that are electrically coupled in parallel to avoid temperature gradients along contact lines.

As discussed above, the device 100 can include an inflatable or otherwise expandable member or balloon 110 that is used to approximate the contact points to the tissue in many embodiments. The inflatable or otherwise expandable member 110 may be shaped to conform to the inner wall of the organ when inflated. The balloon 110 may be pre-shaped to the shape of a urinary bladder. The balloon 110 or other expandable member or approximating device may be pre-shaped to best fit the urinary bladder. In some embodiments, the cross section of the upper pole of the balloon is visibly larger than the cross section of the lower pole—the pole closer to the bladder outlet. In other embodiments, the anterior to posterior axis of the balloon 110 is visibly shorter than the up to down axis, and/or the left to right axis. The balloon 10 may have a high compliance and thus low filling pressures and high conformity. In some embodiments, the element to be placed within the hollow organ does not expand but changes shape. For example, the device or parts thereof change their shape from substantially straight or slightly curved to markedly curved.

Aspects of the present invention also provide methods for creating tissue lines having reduced electrical propagation.

Figure 12:
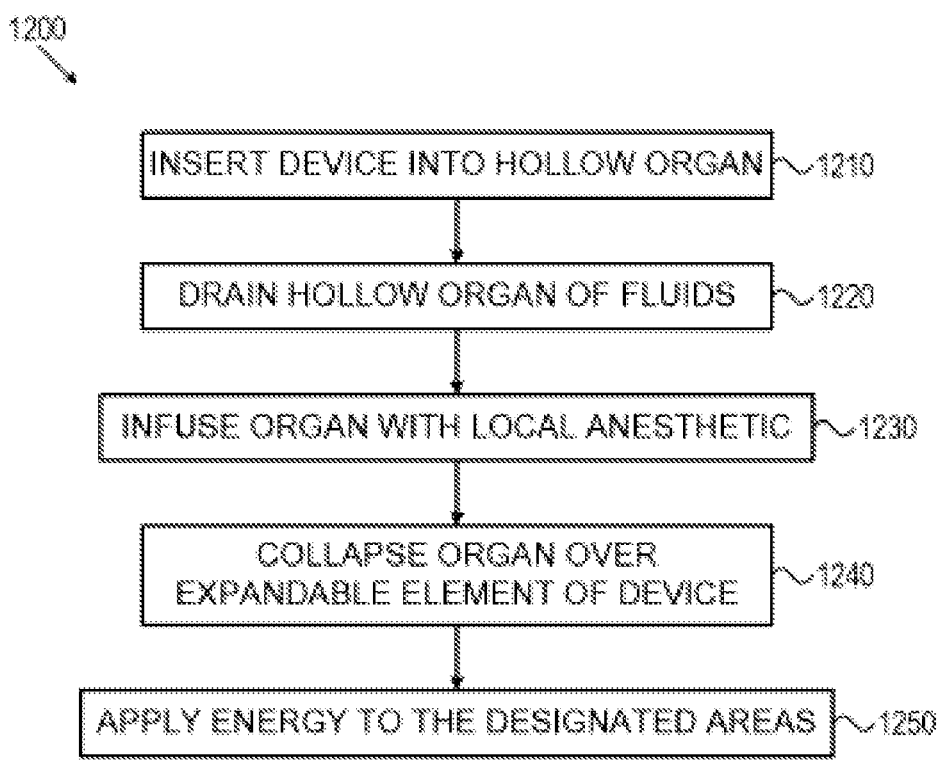
FIG. 12 shows a flow chart of a method to treat a hollow organ, according to many embodiments.

FIG. 12 shows a flow chart of an exemplary method 1200. In a step 1210, a device such as device 100 or similar is inserted into a hollow organ. In a step 1220, the hollow organ is drained of fluids, e.g., the hollow organ is emptied from liquids or other materials occupying the organ such as urine from a bladder. In a step 1230, the organ is infused with a local anesthetic such as lidocaine. In a step 1240, the organ is collapsed over an expandable element, such as balloon 110, of the device to ensure good contact. The step 1240 may further involve expanding or otherwise changing the shape of the expandable element to conform to the inner wall of the organ. This can be done by draining the fluid in the organ or by applying suction. In a step 1250, energy is applied to the designated areas to create the tissue lines. Prior to the step 1250, the device may also electrically map the bladder to determine an appropriate ablation pattern. The present invention may provide a system for performing the method 1200. The system can comprise a processor configured to run code to operate an ablation device 100 or similar devices as well as other accompanying devices to implement the method 1200 or the line in a hollow target organ of a patient.

In some embodiments, the step of expanding the expandable member is preceded by a step of pharmaceutically expanding the organ. For example, bronchodilators for bronchial application, muscle relaxants for bladder applications, etc. In some embodiments, the step of expanding the member is followed by a step of pharmacologically or otherwise contracting the hollow organ to be treated. For example, urinary bladder contraction can be induced once the device is in place.

In some embodiments, ablation is applied to the urinary bladder wall when the bladder volume is minimized, e.g., by draining, and thus the bladder wall thickness is maximal and the chance for bladder perforation is reduced. In other embodiments, ablation is applied to the urinary bladder wall when the bladder is expanded after so that the bladder wall is thinned and a transmural lesion can be readily achieved.

In some embodiments, the performance of the tissue lines having reduced electrical propagation is tested by stimulation and recording the electrical activity from different sides of the line. The time for signal propagation over the line is measured and success can be defined as a time lag that is at least three times the time lag expected by the distance between the point of stimulation to the reading point divided by the velocity of signal propagation in the specific tissue concerned.

In some embodiments, the creation of the reduced electrical propagation tissue lines is preceded by measuring the intrinsic electrical activity of the organ.

In some embodiments, the reduced electrical propagation tissue lines are zig-zag lines, to increase the length of actual ablated tissue without increase the width of the ablation line.

Figure 13:
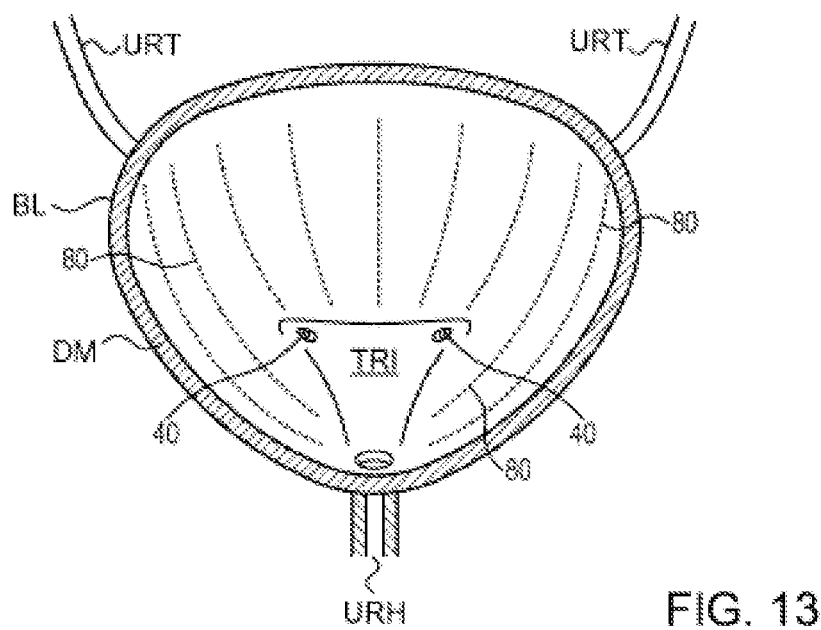
FIG. 13 is a cut-away view of a bladder having parallel ablation lines created thereon, according to many embodiments.

In some embodiments, the ablation lines 80 are parallel lines arranged to avoid one or more anatomical areas such as the trigone area TRI as shown in FIG. 13. FIG. 13 shows a cut-away view of a bladder BL with such ablation lines 80. Also shown are the detrusor muscle DM, the urethra URH, ureters URT, and ureteral openings UO.

Figure 14:
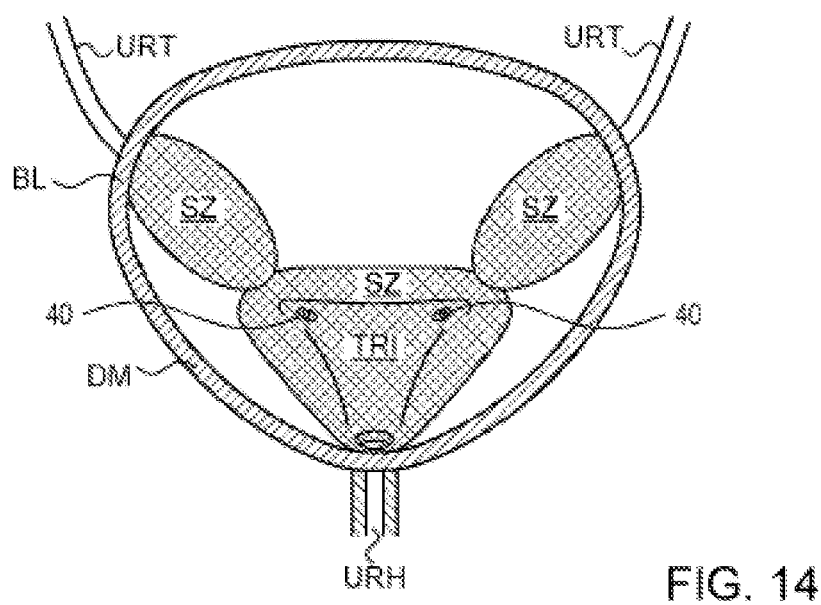
FIG. 14 is a cut-away view of a bladder showing safe zones to avoid ablation, according to many embodiments.

In some embodiments, the device includes a "safe zone" or a "safety zone," where no energy is applied to, in order to protect sensitive areas, such as the ureterovescical orifices in the urinary bladder. This "safe zone" or "safety zone" actively acts as a spacer, planned to displace the energy source from the sensitive areas. FIG. 14 shows a cut-away view of a bladder BL showing exemplary safe zones SZ on the inner wall of the bladder BL where no energy is applied.

Many parameters can be measured while the reduced electrical propagation tissue lines are created. The temperature of the device may be monitored. The temperature of the contact points may be monitored. The pressure of the contact points over the tissue may be monitored. The impedance between the device and the tissue may be monitored.

Figure 15:
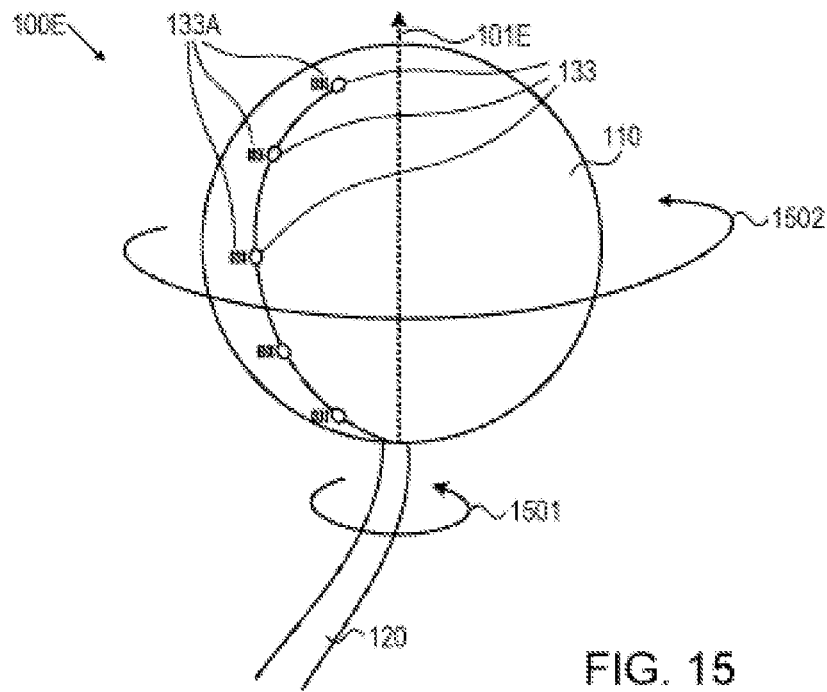
FIG. 15 is a perspective view of a rotatable ablation device, according to many embodiments.

As discussed above, the reduced electrical propagation tissue lines 80 can be created by applying energy through the electrodes 132 disposed on an expanded balloon 110 held stationary within the bladder or, in some embodiments, can be created by rotating the balloon 110 to move tissue modification contacts disposed over the balloon. As shown in FIG. 15, an ablation device 100E similar to the ablation device 100 comprises a plurality of electrode contact points 133 disposed over the balloon 110 along a longitudinal line. The balloon 110 can be rotated in a direction 1502 by rotation of the flexible shaft 120 in a direction 1501 to create multiple ablation lines transverse to the longitudinal axis 101e which is aligned with the longitudinal axis of the hollow organ or bladder. The flexible shaft 120 will typically be torquable so that rotation of the shaft 120 can rotate the balloon 110. FIG. 15 further shows parts of the paths 133A the electrode contact points 133 travel as the balloon 110 is rotated.

Figure 16:
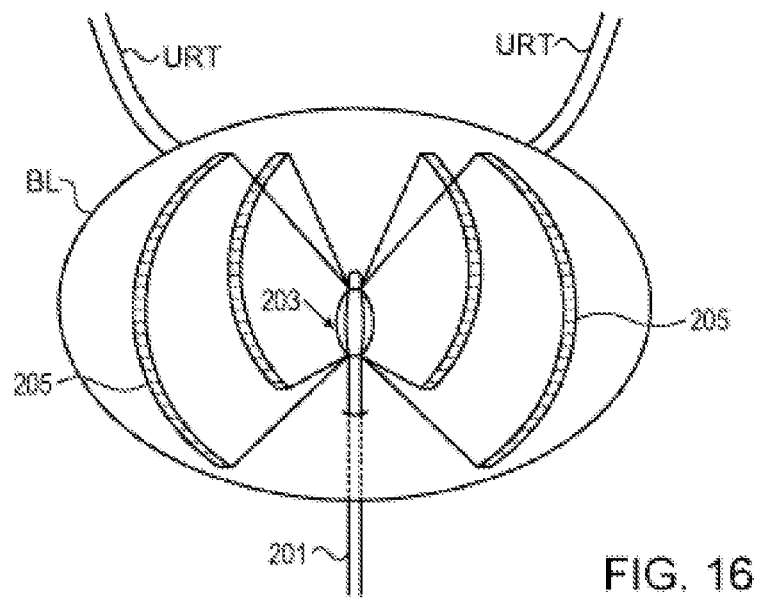
FIG. 16 is a cut-away view of a bladder having a catheter with a light source placed therein, according to many embodiments.

In many embodiments, it is appreciated that direct visualization of the ablation while creating ablation lines is pivotal for procedure safety and flexibility. The hollow organ such as the bladder can be illuminated or otherwise visualized while the lines or regions of reduced electrical propagation are being created. In some embodiments, the lines of modified tissue may be created under visualization using ultrasound, for example, from an ultrasound source advanced into the hollow organ. In some embodiments, light is applied. FIG. 16 shows a catheter 201 having a light source 203 disposed on its distal end. The catheter 201 has been advanced through the urethra to position the light source 203 within the bladder BL. The light source 203 illuminates the inner wall of the bladder BL along lines 205 which may correspond to the ablated or otherwise modified tissue lines to be created by the device 100 or others.

In some embodiments, the light source 203 may even be used to create the lines of modified tissue such as by delivering laser light along the desired lines. The wavelength applied may be between 800 to 1,300 nm, for example 900 nm. Applying such light can be done by optic fibers delivering the energy directly to the bladder wall, or by a prism placed near the light source 203 at the end of the catheter 201 in the center of the bladder BL, which creates the laser light pattern on all the bladder surfaces at once along lines 205.

Figure 17:
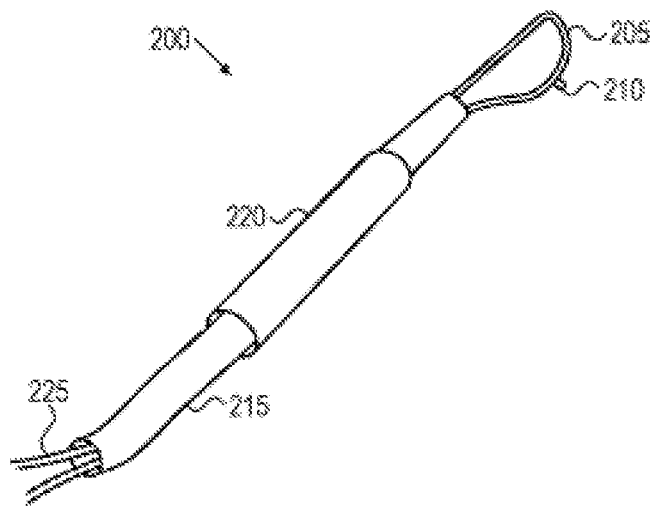
FIG. 17 is a perspective view of a tool for drawing ablated or otherwise modified tissue lines within a hollow organ, according to many embodiments.

The lines of modified tissue may also be drawn on the inner wall of the bladder BL using a tool 200 shown by FIG. 17. The tool 200 comprises a curved distal wire portion 205 having an active tissue modification element 210. The curved distal wire portion 205 is curved to protrude in one direction. The tool 200 further comprises an elongate inner shaft 215 and an elongate outer shaft 220 slidably disposed over the elongate inner shaft 215. The elongate outer shaft 220 can be advanced to collapse and cover the curved distal end 205 to reduce the profile of the tool 200 as it is advanced into a hollow organ. The elongate outer shaft 220 can be retracted over the elongate inner shaft 215 to allow the curved distal wire portion 205 to assume its curved shape as shown in FIG. 17. If applicable, energy can be transferred to the active element 210 through leads 225 disposed within the elongate inner shaft 215. In some embodiments, the active element 210 comprises an electrode for delivering RF, microwave, heat, or other energy. The lines of ablated or otherwise modified tissue can be created by rotating or translating the tool 200 within the hollow organ. In some embodiments, the inner shaft 215 can be rotated while holding the outer shaft 220 stationary within the urethra to minimize any damage that may be caused to the urethra by such rotation.

In some embodiments, the active element 210 comprises a blade to modify the tissue by cutting or incision. The depth of the incision can be controlled by the choice of the appropriate blade wire out of a selection including several different depths, ranging from 2 mm to 8 mm, for example, 4 mm. The depth of the incision is determined by the protrusion of the blade from the surface of the expandable member such as the distal end 205 biased to expand to its curved configuration. Scar tissue formed after the cut can modify the electrical propagation of the surrounding tissue.

In some embodiments, the active element 210 comprises a port for delivering a heated or cooled fluid to ablate tissue.

In some embodiments, the active element 210 comprises a dedicated cup-shaped member that contacts the inner wall of the organ to facilitate the creation of modified tissue lines.

In some embodiments, the elongate tool 200 can be guided by the channels 140 disposed on the expanded balloon 110 of the device 100c shown by FIG. 10, for example, to cut or ablate tissue along the direction of the channels 140. The channel 140 holding and guiding the blade can be covered or roofed along certain areas of the channel 140. The channel 140 may be roofed from the insertion point and up to 3 mm above the bladder outlet. The roofing may be longer on the dorsal aspect of the expandable member than on the ventral side, for example, to prevent dissection in the area of the trigone. The roofing can resume toward the dome of the expandable member, leaving 4 mm or more protected. The curved distal wire portion 205 may be bladed only segmentally. The roofed segments of the guiding channels 140 adapted to face the body of the bladder may be significantly shorter from the exposed segments in these areas, i.e., only one tenth of each channel is roofed in this zone. In other embodiment, the channel supporting the wire 205 is intermittently roofed, to support the wire blade 205 and to create non-continuous lines. In some embodiments, roofed segments along one blade line are in close proximity to the non-roofed segments of a different line so that there is some overlap between lines and the cuts are continuous or near continuous.

The blades can be configured in many other ways. Short blades may be connected, for example by a string, so that several blades can be pulled together as one, while allowing the expandable member to easily deform and adapt to the shape of the bladder. The blades may be positioned to be tangent to the circumference of the device and may be moved to a radial cutting position only when pulled or pushed into the desired position of the line. The necessary blades may be pre-positioned on the device. The blades may be inserted into the device once the device is in position. In some embodiments, the blades protrude from a surface that has a width of at least 3 mm, e.g., 6 mm. This extra width of the surface supporting the blade prevents the blade from "sinking" into the tissue it is cutting. In some embodiments, cutting, scarring, and/or coagulation are facilitated by passing an electrical current through the blades.

In some embodiments, the lines of ablated or reduced electrical propagation tissue are especially crowded in the trigone area which is densely innervated.

In some embodiments, the step of creating the lines is preceded by a step of infusing the bladder with lidocaine or other local anesthetic and/or muscle relaxant and/or anticholinergic agent so that the bladder wall is relaxed and able to stretch.

In some embodiments, in order to facilitate the creation of the lines, the bladder is inflated with an inert gas such as $CO_2$.

Coverage of the ureteral openings for preventing backflow of the pressurized gas is performed by dedicated parts of the device. These can be shaped as plugs entering the orifices or as flat wide covers that are pressed against the bladder wall over the orifices.

In some embodiments, the expandable member such as balloon 110, an introduced gas, and/or an introduced fluid applies pressure on the bladder wall to attenuate the occurrence of edema. In some embodiments, such pressure will be in the range of 10 to 30 cm of water such as 14 cm of water.

In some embodiments, special care is taken to minimize the damage to the urothelium when creating the lines. In some embodiments, the member coming in direct contact with the urothelium and adapted to create the lines will be cooled as described above.

While typically reduced compliance of the bladder is associated with overactive bladder symptoms, a method provided by the current invention treats overactive bladder symptoms by preferentially reducing the compliance of the bladder at certain areas, while allowing other areas to stretch without interruption. In some embodiments, the lines and the resulting scarring and fibrosis are induced in the urinary bladder to change the bladder wall properties so that the compliance of certain areas in the bladder wall is reduced. In some embodiments, lines within the trigone area limit the stretching of the trigone upon bladder filling. In some embodiments, the stretching and contraction of the dome of the bladder is reduced.

Figure 18:
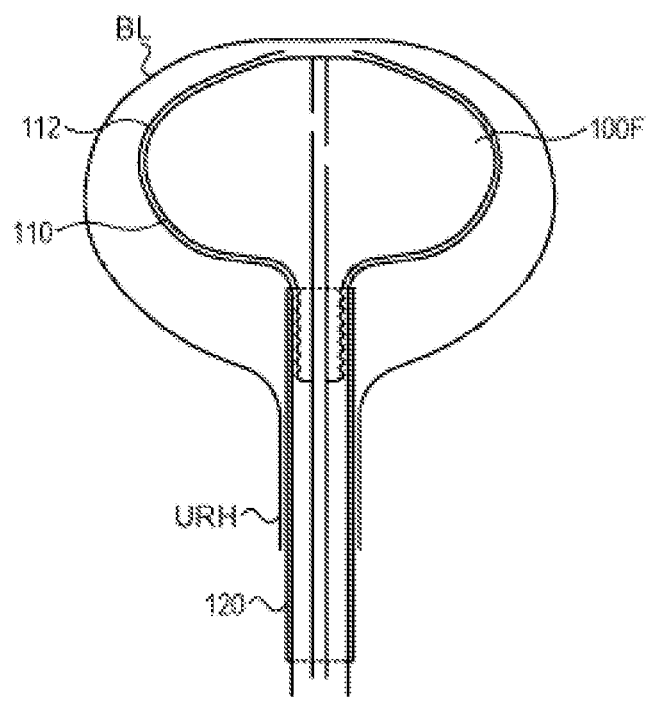
FIG. 18 is a cut-away view a bladder having an ablation device with a cage-like structure advanced therein, according to many embodiments.

In some embodiments, for example as shown in FIG. 18, a cage-like structure 112 of a device 100F is used to deliver energy to the bladder wall. An advantage of using such a structure is that it can allow for better and easier visualization of the device and bladder from within the bladder, with a cytoscope, a miniature video camera, or any other optical device. Another advantage is that the cage-like structure can avoid possible damage to the balloon due to warming of the electrodes or tissue. FIG. 18 shows the cage-like structure 112 disposed over a deflated balloon 110. The cage-like structure 112 is made of a malleable or superelastic metal and is located at the distal end of the catheter shaft 120.

In use, the catheter shaft 120 is inserted into the bladder and positioned at its center. As the balloon 110 is inflated, it expands the cage-like structure 112 until its struts oppose the bladder wall. Since the balloon 110 and cage 112 are longer in the non-expanded than in the expanded state, part of these structures will be out of the bladder, i.e., could be within the urethra at the time inflation begins. An external sheath, such as the distal part of the shaft 120, prevents expansion of the parts of the balloon 110 and cage 112 that are outside the bladder, until they are gradually pulled into the bladder, as the balloon 110 inflates. After full expansion of the cage 112, the balloon 110 can be deflated.

An advantage of this device 100F is that the device 100F may adapt to the precise anatomical shape of the bladder. Removal of such cage 112 can be done by forcefully pulling it into the rigid shaft 120 at the bladder outlet, such that the cage 112 is compressed and assumes a diameter which allows it to exit.

Figure 19:
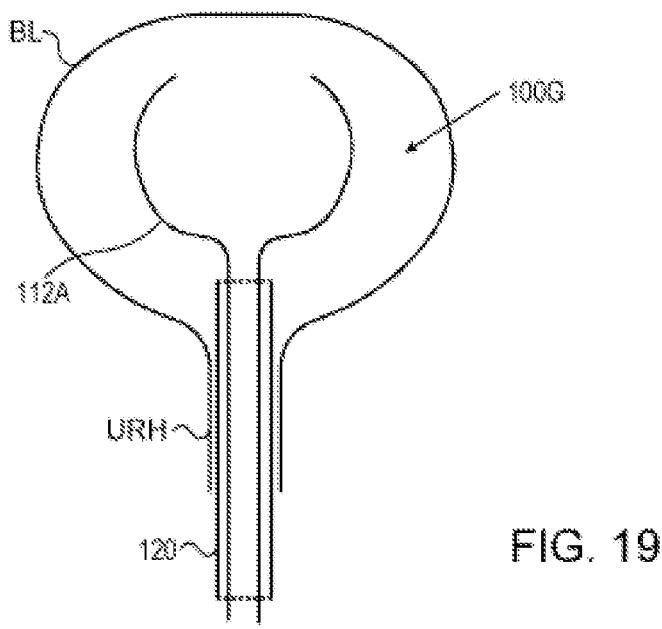
FIG. 19 is a cut-away view of a bladder having another ablation device with a cage-like structure advanced therein, according to many embodiments.

In other embodiments, the ablation or tissue modification device 100G does not utilize as balloon as shown in FIG. 19. In these embodiments, the cage-like structure 112A is self-expandable. The cage-like structure 112A can be made of a shape memory metal such as Nitinol and can be pre-shaped to assume the typical anatomy of the bladder. The cage-like structure 112A can be advanced from the lumen of the shaft 112A to expand and retracted into the lumen to collapse it.

Alternatively, the cage-like structure 112A could be made of a plastic polymer and electrodes could be attached to it.

Figure 20:
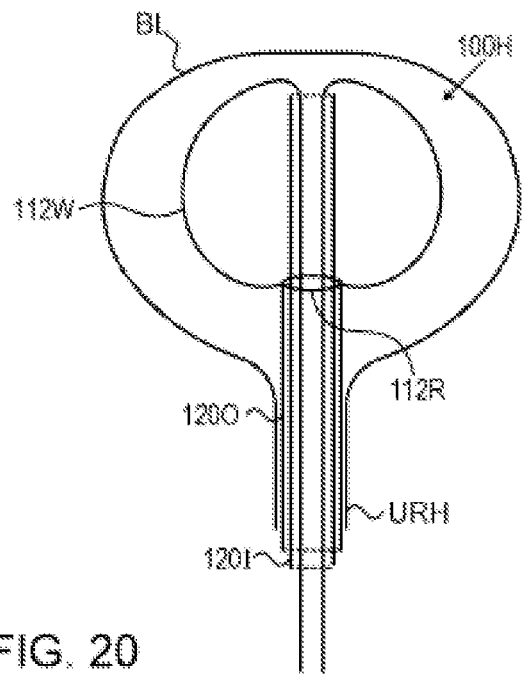
FIG. 20 is a cut-away view of a bladder having yet another ablation device with a cage-like structure advanced therein, according to many embodiments.

Another embodiment of a device 100H similar to the device 100G is shown in FIG. 20. The device 100G comprises multiple flexible wires 112W connected to a ring 112R. The wires 112W project forward from the perimeter of the ring 112R, coil back and pass through an inner tube 1201. The ring 112R is connected to the distal tip of an outer catheter tube 1200. The outer catheter tube 1200 can be advanced over the inner catheter tube 1201 which encircles all the wires 112W.

In use, the catheter tube 1201 is placed within the bladder BL with its tip at the bladder outlet. The wires 112W are pushed forward so they arch toward the bladder wall. The inner tube 1201 is pushed toward the dome of the bladder. The inner tube 1201 holds the wires 112W together at the distal side of the formed structure such that its shape can be adapted to that of the bladder BL and the wires 112W come in contact with the bladder wall.

The cage-like structures 112, 112A, 112W described above are preferably continuous with or connected to a cable exiting the bladder through the catheter 120. This connection serves as an anchor for the cage-like device, which also aids in its removal. In addition, the connection allows for transfer of energy such as electromagnetic energy or mechanical energy for example in the form of vibration.

Figure 21:
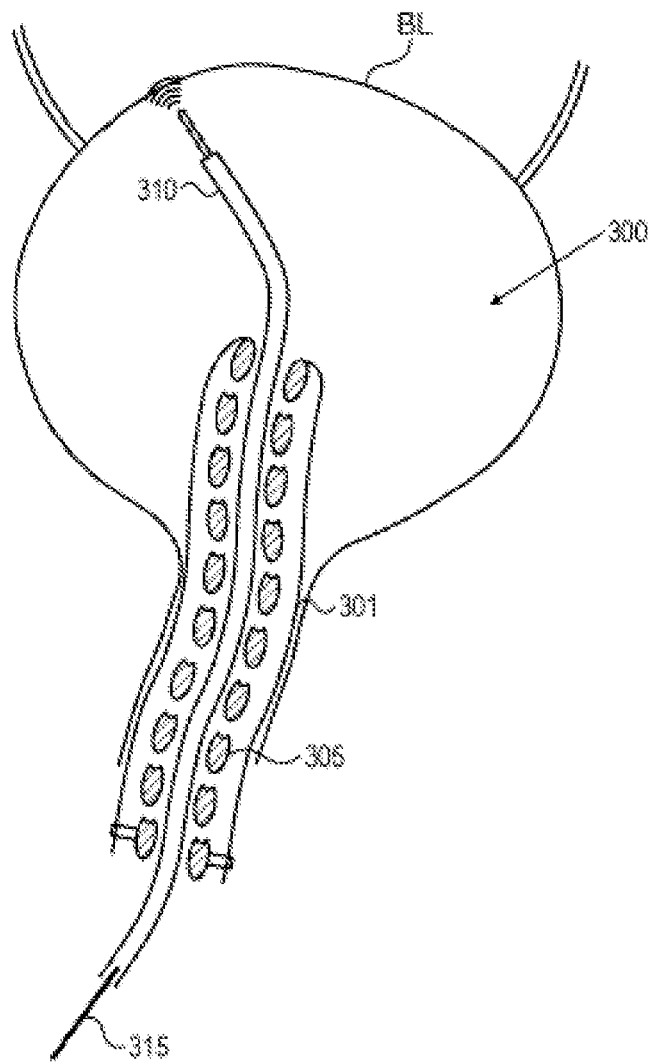
FIG. 21 is a cut-away view a bladder having an ablation system advanced therein, according to many embodiments.

Another embodiment is shown in FIG. 21 which shows a system 300 for ablating or otherwise modifying tissue in a hollow bodily organ. The system 300 can provide the surgeon with a stable base within the bladder BL from which he can work, while allowing him to control the precise location of the ablation catheter 315. The system 300 comprises a shaft 301 comprised of multiple links 305 that may be pulled together to prevent their relative movement and maintain the shape of the shaft 301. This can be done by a wire going through the links 305 or by an external sheath connected to the last link. A flexible cystoscope 310 of the system 300 can be inserted through the shaft 301. An ablation catheter 315 of the system 300 can be inserted through the cystoscope 310 and directed at any point on the bladder wall.

With the above balloon-less devices, inflation of the bladder may be necessary both for stretching the bladder and for minimizing edema in the wall. As described above, temporary closure of the ureteral orifices may be performed with dedicated parts of the device to prevent backflow during high pressure inflation.

An issue that can be relevant to the embodiments wherein electrodes 132 are embedded in an inflatable balloon 110 is that the length of the electrodes 132 can be greater when the balloon 110 is inflated than when it is deflated. Often, the electrodes 132 accommodate this difference in several ways. The electrodes 132 may be made of an extensible material, for example a thin metal strip of stainless steel, so that when the balloon 110 inflates, they elongate as needed, and remain so. Alternatively, the electrodes 132 could be made of a flexible conductor, such as various graphene based conductors. Still alternatively, the parts or all of the electrodes 132 may be shaped in a delicate zig-zag pattern such that the electrode 132 can straighten out and allow elongation. Lastly, the electrodes 132 may consist of multiple slideable sections that allow elongation while maintaining electrical continuity.

Areas of the cage-like structure 112, 112A and cable or electrodes 132 that do not ablate may be shielded to prevent unintentional ablation or undue transfer of energy to tissues or parts of the device.

In some embodiments, the devices and methods described herein are used to induce bladder auto-augmentation. Thin incisions of the detrusor muscle can allow the creation of bladder diverticuli, where the mucosa and submucosa protrude into the abdominal cavity and the bladder capacity is increased. In some embodiments, the autoaugmentation is achieved using the abdominal approach and in some embodiments, the autoaugmentation is achieved through the urinary bladder. In some of the latter embodiments, the cutting or ablation of tissue is achieved by creating a skip lesion to ablate the underlying detrusor while minimally harming the mucosa. Such skip lesions may be created by various methods known in the art, such as focused ultrasound, cooled RF probes, microwave probes, etc. In other embodiments, the lesions are transmural, and become epithelialized only later, by way of natural epithelial regeneration.

In some embodiments, the lines created are then coagulated to prevent bleeding. In some embodiments, the same element used for ablation is used for coagulation. In some embodiments, when the lines are created surgically, coagulation cautery is applied to the blades to prevent bleeding and facilitate scarring.

Figure 22:
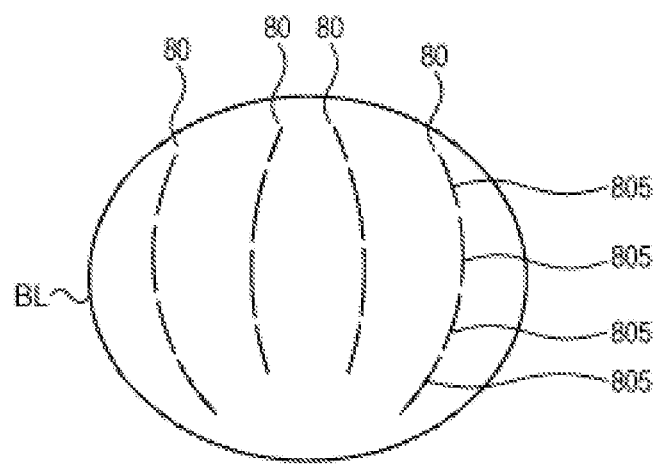
FIG. 22 is a cut-away view of the bladder showing a pattern of ablation lines created therein, according to many embodiments.

In some embodiments, the ablation or reduced propagation lines 80 are created in short segments 80s at a time in bladder BL as shown in FIG. 22. Typically, the length of each section is between 2 cm to 10 cm, preferably 3-4 cm.

Figure 23:
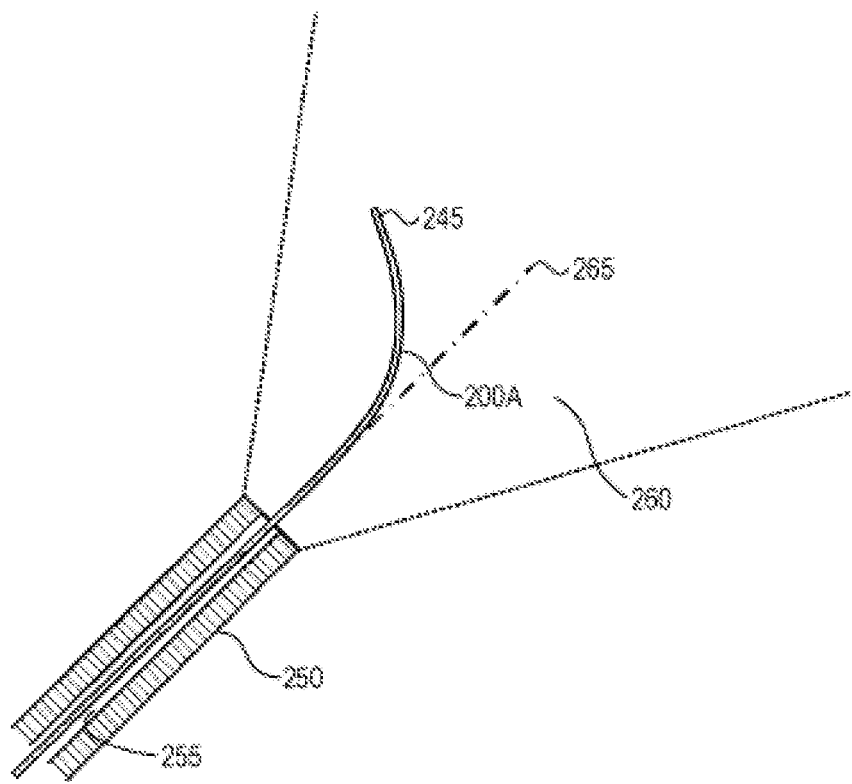
FIG. 23 is a cross-sectional view of an ablation tool having a pre-curved distal portion, according to many embodiments.

FIG. 23 shows such an ablation tool 200A similar to ablation tool 200 described above. In some embodiments, the ablation tool 200A is fitted through the working channel 255 of a standard scope 250 as shown in FIG. 23. The ablation tool 200A may have an external diameter of less than 3 mm. The ablation tool 200A can extend beyond the length of the scope 250 for a distance of 2 cm to 10 cm. The ablation tool 200A or part of it is flexible and pre-shaped, so that when extended beyond the working channel of the scope the tool will bend away from the centerline 265 of the scope's field of vision 260. The distal portion 245 of the tool 200A can be pre-shaped as an arc as shown in FIG. 23 in some embodiments. In these embodiments, the surface of the tool that comes in direct contact with the bladder, i.e., the electrode, can be pressed against the bladder under direct visualization through the scope 250.

Figure 24A:
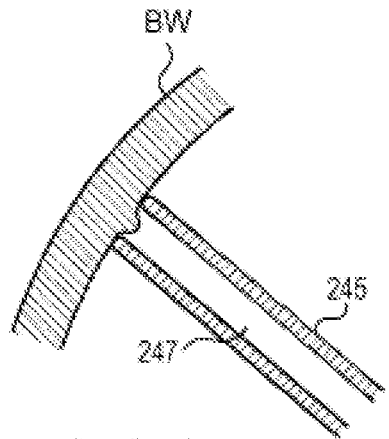
FIG. 24A, FIG. 24B, FIG. 24C, and FIG. 24D are cross-sectional views of various distal tips of the ablation tool of FIG. 23, according to many embodiments.
Figure 24B:
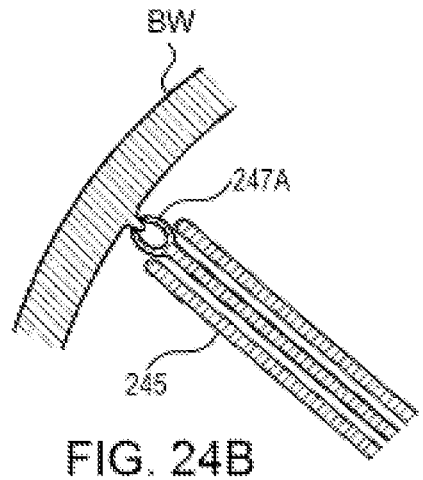
Figure 24C:
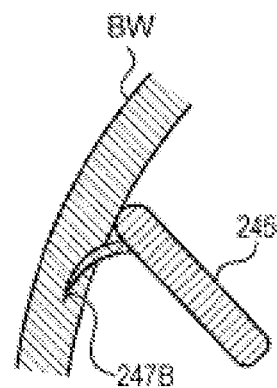
Figure 24D:
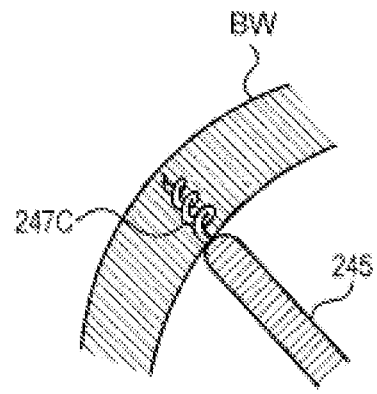

In some embodiments, part of the tool 200A can be designed to gain fraction against the bladder wall BW so that the tool 200a can be maintained at a certain position even if the scope is moved so that continuity of ablation lines can be achieved. Such traction may be created, for example, by none-smooth surfaces in part of the device, applying suction to the bladder wall BW through a channel 247 in the distal portion 245 of the tool 200A as shown in FIG. 24A, by "pinching" of the bladder wall BW tissue applied by a miniature pair of tweezers 247A as shown in FIG. 24B, by a straight or curved needle 247b extending outward from the distal portion 245 of the tool 200A as shown in FIG. 24C, by a spiral needle 247C extending outward from the distal portion 245 of the tool 200A as shown in FIG. 24D, or the like.

Figure 25A:
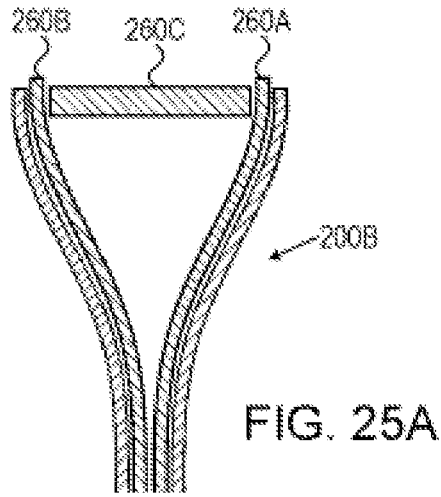
FIG. 25A is a cut-away view of a tip of an ablation tool, according to many embodiments.
Figure 25B:
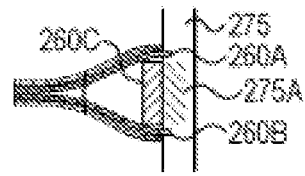
FIG. 25B, FIG. 25C, FIG. 25D, FIG. 25E, and FIG. 25F are schematics of a method of using the ablation tool of FIG. 25A to create an ablation pattern, according to many embodiments.
Figure 25C:
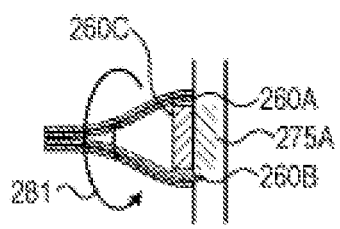
Figure 25D:
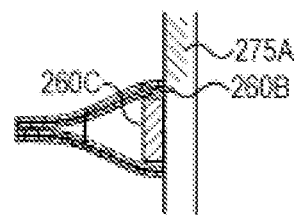
Figure 25E:
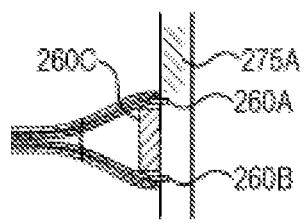
Figure 25F:
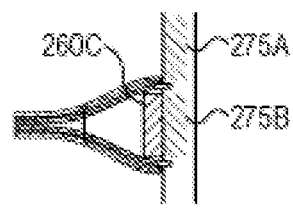

In some embodiments, line continuity is achieved by rotational movement of the ablation tool, with the so called "anchor" of the electrode being the pivot of rotation. A second "anchor" structure can be positioned on the other side of the electrode segment that creates the segment of ablation. The progression of the tool along the intended ablation line can be achieved by rotational movement of the tool 180 degrees while one "anchor" acts as a pivot, followed at the next step by a 180 degree rotation to the other side, with the other anchor acting as a pivot. This may be achieved by a device 200B as shown in FIG. 25A. The device 200B can be collapsed into a low-profile configuration and advanced into the bladder through the scope 250. The device 200B comprises a first extendable and retractable electrode tip 260A and a second extendable and retractable electrode tip 260B, both of which can act as "anchors." The electrode tips 260A and 260B are connected by a wire electrode 260C. The whole device 200B can be rotated about the axis of the first electrode tip 260A or second electrode tip 260B. During ablation, both tips 260A, 260B are extended, serving to anchor the electrodes 260A, 260B and wire 260C in place as shown in FIG. 25B. After a first tissue segment 275A is ablated by the electrodes 260A, 260B, the distal tips 260A is retracted and the device 200b is rotated 180 degrees in a direction 281 around the tip 260B which serves as an "anchor" as shown in FIG. 25C and FIG. 25D FIGS. 25C and 25D. The retracted tip 260A is then extended as shown in FIG. 25E and ablation is performed to ablate a second tissue segment 275B as shown in FIG. 25F. The distal tip 260A becomes the new anchor. The process can be repeated again as needed. The rotation and anchoring steps can be performed by the user with a trigger mechanism that mechanically transmits movement to cause the desired circular movement such that each pull of the trigger will move the device one complete "step," without the user needing to attend to the stages described above. The resulting tool handle held by the performing physician will look and feel like many other endoscopic surgical tools the physician may be used to.

Figure 25G:
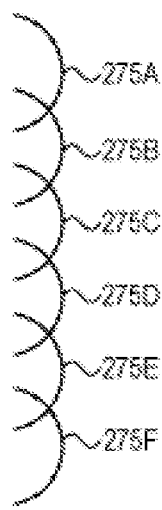
FIG. 25G is a top view of an ablation pattern that uses short curved lines to create a continuous isolation front that can be created using the ablation tool of FIG. 25A and other ablation tools including those of FIGS. 17, 21, and 23, according to many embodiments.

In some embodiments, the area of the tip 260A, 260B has a larger surface area or special coating so that the ablation around this area is less than the ablation along the electrode wire 260C. This area can be ablated at reduced intensity; however, since this zone is actually ablated twice while the ablation line is being drawn, the result is an even ablation along the entire ablation line. Alternatively, no ablation is applied at the "anchoring" zones, and the continuity of the ablation line is achieved by overlapping of a curved foot print as shown in FIG. 25G showing overlapping, semi-circular ablation zones 275A, 275B, 275C, 275D, 275E, and 275F. In some embodiments, the electrode 132 coming in contact with the bladder wall can be pre-shaped to have a curved foot print on the bladder wall. For these embodiments, a continuous ablation line can be achieved even if ablations are not carefully continuous, for example, by creating an overlap between adjacent ablation segments.

In some embodiments, the first part of the electrode, i.e., the part extending from the distal exit of the scope 250 to the first anchor, is built to have a specifically predetermined flexibility so that when force is applied to it by pressing the tool 200b against the bladder wall BW, the tool 200b will bend in an expected manner. In other embodiments, other elastic members have the same property—change of length or protrusion of the tool 200B from the scope 250, as a result of the force applied by the tool to the bladder wall BW. This can be achieved by a coiled spring. In some embodiments, the elastic member or coiled spring is sheathed within the scope 250.

Figure 26A:
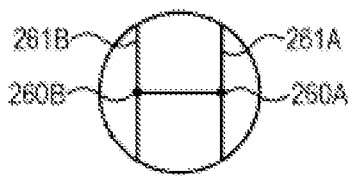
FIG. 26A, FIG. 26B, and FIG. 26C show a view of tip of an ablation tool through a scope, according to many embodiments.
Figure 26B:
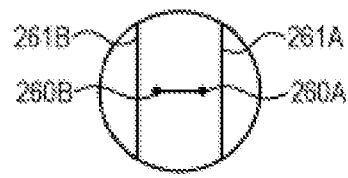
Figure 26C:
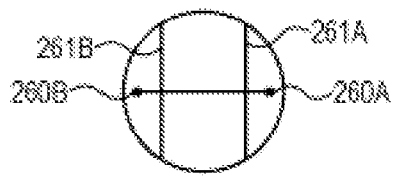

In these and other embodiments, when the tool 200b is not pushed against the bladder wall, the tool extends out of the scope 250 to a fixed distance. Thus, the actual distance of the scope 250 from the bladder wall BW depends on deformation of the elastic member and is proportional to the force applied against the bladder wall BW. In some embodiments, the distance of the scope 250 from the bladder wall when the tool 200B is extended and no pressure is applied is set so that a user will immediately visually recognize when enough pressure is applied by visual cues. Such cues may be based on the correct distance of the scope 250 from the wall BW, which is a surrogate of the correct applied pressure. In some embodiments, the optical clue used is the perceived distance between electrode tips 260A, 260B. The desired perceived distance can be set so that the tips 260A, 260B will extend between two markings 261A, 261B within the visual field seen through the scope 250. If correct pressure is applied, the user will see the tips 260A, 260B extend exactly between the markings 261A, 261B as shown in FIG. 26A. If insufficient pressure is applied, the user will recognize that the tips 260A, 260B do not span the gap between the markings 261A, 261B as shown in FIG. 26B. When too much pressure is applied, the scope will move closer to the bladder wall BW and the distance between the tips 260A, 260B will appear wider than the gap between the markings 261A, 261B as shown in FIG. 26C. In some embodiments, the visual field borders are used instead of markings.

Thus, the tool 200B extends out of the scope 250 to a known distance, as long as the tool is not pressed against the bladder wall BW. Once pressed, this length is changed so that when the scope is too near to the bladder wall BW, the user can conclude that the arch or other elastic member is excessively deformed, meaning the force applied is too high to be safe. When the pressure of the electrode tips 260A, 260B against the bladder wall BW exceeds a certain value, ablation may be hazardous, risking bladder wall perforation. If, on the other hand, the user recognizes that the distance between the scope and the bladder wall is too large, the user can conclude that the arch or other elastic member is insufficiently deformed, meaning the electrode is not pressed hard enough against the bladder wall BW, risking ineffective ablation or the formation of coagulum.

In some embodiments, the electrodes of electrode tips 260A, 260B are somewhat arched so that the known elasticity of the arch and two opposing arms of the tool which form "forceps" can be used to maintain the electrode contact with the tissue at a relatively constant value. If the tool 200B is pressed against the bladder with force, the arched electrodes will become flat while forcing the tool "forceps" to open apart. The ablation may be performed only when the distance between the forceps arms is around a certain value, and ablation is aborted when this value is exceeded. In some embodiments, the ablation is not performed unless the distance between the arms of the device 200B exceeds a certain threshold, to avoid ablation when contact with the tissue is poor.

In some embodiments, the desired value of force of the electrode against the bladder tissue is set to be such that the contact pressure will be between 100 grams per $cm^2$ to 500 grams per $cm^2$, such as 200 grams per $cm^2$.

In some embodiments, the bladder is filled by air or fluid at high pressure during or immediately after the ablations are performed, to avoid contraction of the bladder and actually facilitate augmentation of the bladder volume by stretching the bladder wall, especially at the recently ablated segments or during ablation. Exemplary values will be to inflate the bladder to a pressure of approximately 80 centimeters H2O and keep it full for one to five minutes before letting the fluid out.

In some embodiments, the gauging of pressure applied by the electrode is achieved by a pressure sensor. In some embodiments, the extension of the tool out of the scope is determined by the pressure against the bladder wall. In some embodiments, the device is set to automatically limit ablation only to times when the pressure is within a pre-set range around the desired pressure.

In some embodiments, the part of the tool 200b that is used to deliver the RF current or other current or energy to the bladder wall is somewhat curved to fit the curvature of the bladder wall. In some embodiments, this curvature is fitted for a sphere with a radius of between 10 cm to 40 cm.

Overactive bladders, especially those which are overactive due to neurogenic causes or severe obstruction, may be characterized by significant trabeculations caused by detrusor muscle hypertrophy. Hypertrophied muscle bundles create bulges and indentations in the bladder wall, making the inner surface of the bladder extremely irregular. Ablating lines in such a situation may in some cases be difficult as the irregular surface tends to distort the lines and the variable thickness of the bladder wall can require different degrees of energy at different areas.

Figure 27A:
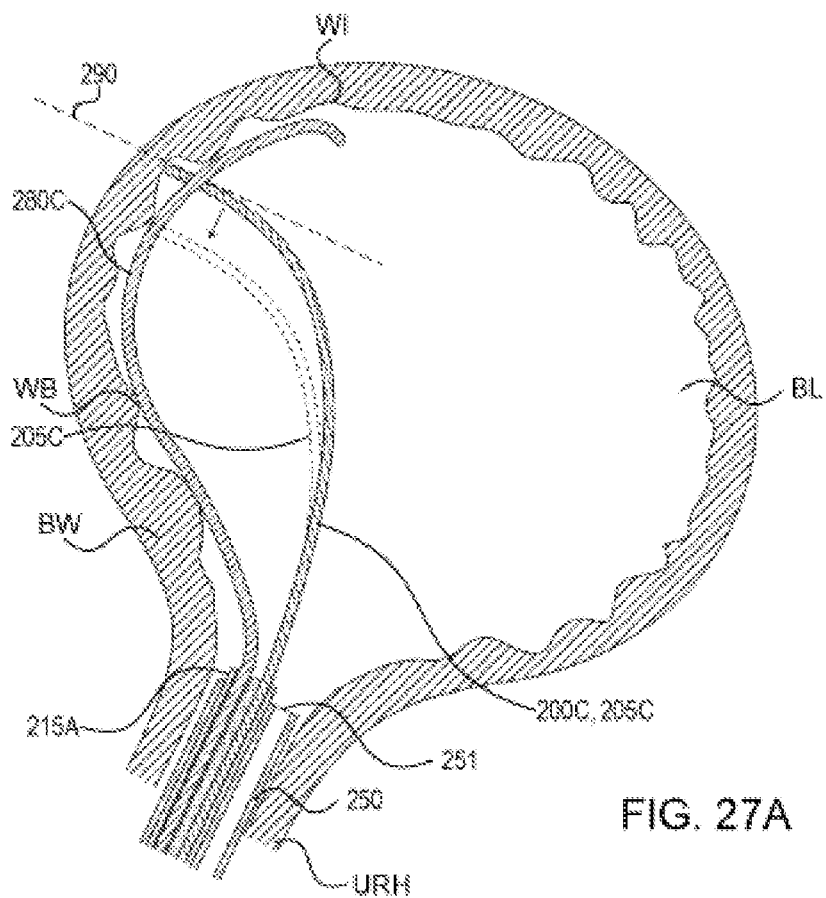
FIG. 27A is a cross-sectional view of an ablation tool having a guide element and placed in the bladder, according to many embodiments.
Figure 27B:
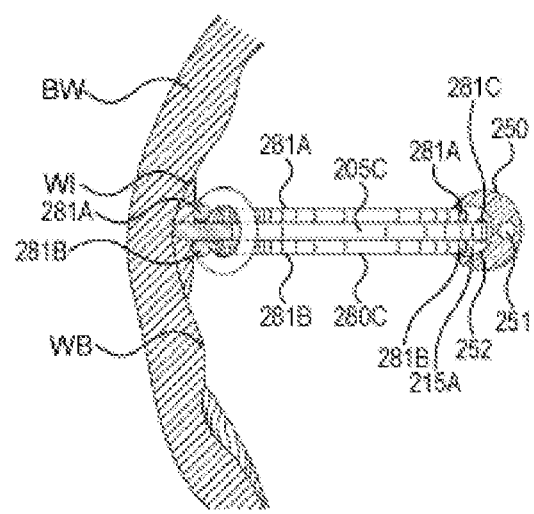
FIG. 27B is a cut-away view of the ablation tool of FIG. 27A positioned near the bladder wall, according to many embodiments.

Embodiments of the invention therefore also provide methods and devices which address the aforementioned issues. FIG. 27A shows an ablation tool 200C similar to tool 200 described above. The ablation tool 200C has arced elongate working tip 205C that is extendable out of the shaft 215A into the bladder BL which has bulges WB and indentations WI along its inner surface. The ablation tool 200C further comprises an arced guide 280C preshaped with an arc with a direction opposite that of the working end of the ablation tool 200C. FIG. 27B shows a closer top view of the ablation tool 200C. As shown in FIG. 27B, the guide 280C has two arms 281A and 281B which are either insulated or made of a non-conductive material.

FIG. 27A is a cross-sectional view of the ablation tool 200C in the bladder BL in the coronal plane. FIG. 27B is a top view of the ablation tool 200c through the line 290 in FIG. 27A. A cystoscope 250 is shown entering the bladder BL through the urethra URH. The cystoscope 250 has optics and a working channel 252 through which the ablation tool 200C, including the shaft 215A, is advanced through. The shaft 215A of the ablation tool 200C includes two rounded lumens 282A, 282B for the two guide arms 281A, 281B and an oblong lumen 281C for the working tip 205C of the ablation tool 200C. The oblong shape of the oblong lumen 281C keeps the working tip 205C and the guide arms 281A, 281B in the same orientation relative to each other. The working tip 205C is held between the two guide arms 281A, 281B. The working tip 205C may further be wider near its distal ends to prevent slipping from between the guide arms 281A, 281B. The ablation tool 200C is shown in two positions in FIG. 27A, the first over an indentation WI in the bladder wall as shown with the tip 205C in dotted line and the other over a bulge WB in the bladder wall.

In use, the tool 200C with the guide 280C and the elongate tip 205C retracted in the shaft 215A is inserted through the working channel 252 of the scope 250. Then, the guide 280C and the elongate tip 205C are deployed. The guide 280C then extends from the scope 250 until it touches the bladder wall. The elongate tip 205C is initially at the distal end of the guide 280C and is then gradually drawn towards the scope 250 while ablating. As the elongate tip 205C moves along the inner wall of the bladder, the guide arms 281A, 281B prevent the tool from "skewing" sideways with the ridges the hypertrophied muscles bundles creating the irregular surface.

Figure 28A:
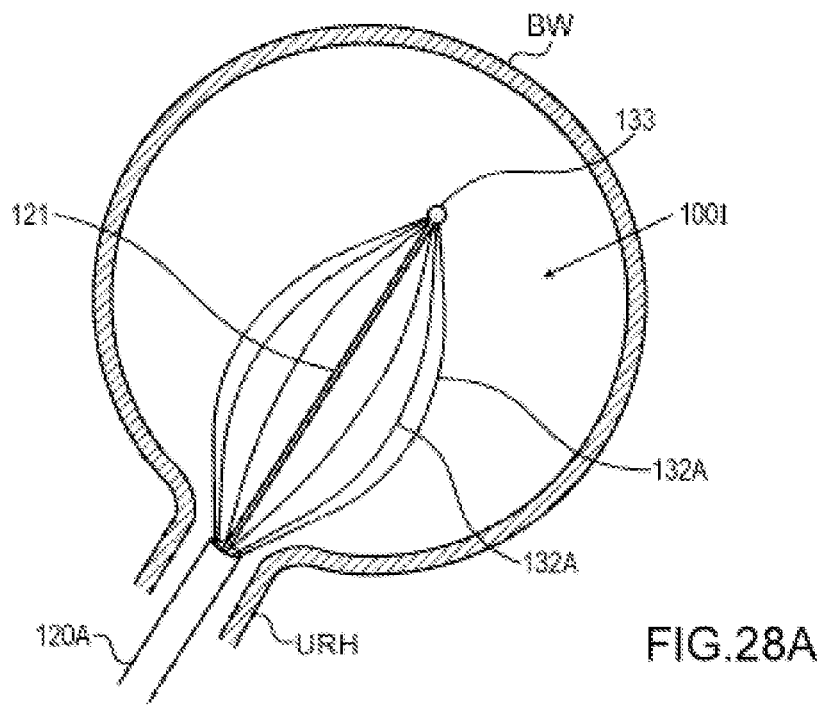
FIG. 28A is a cut-away view of an ablation tool having a distal balloon placed within the bladder, according to many embodiments.
Figure 28B:
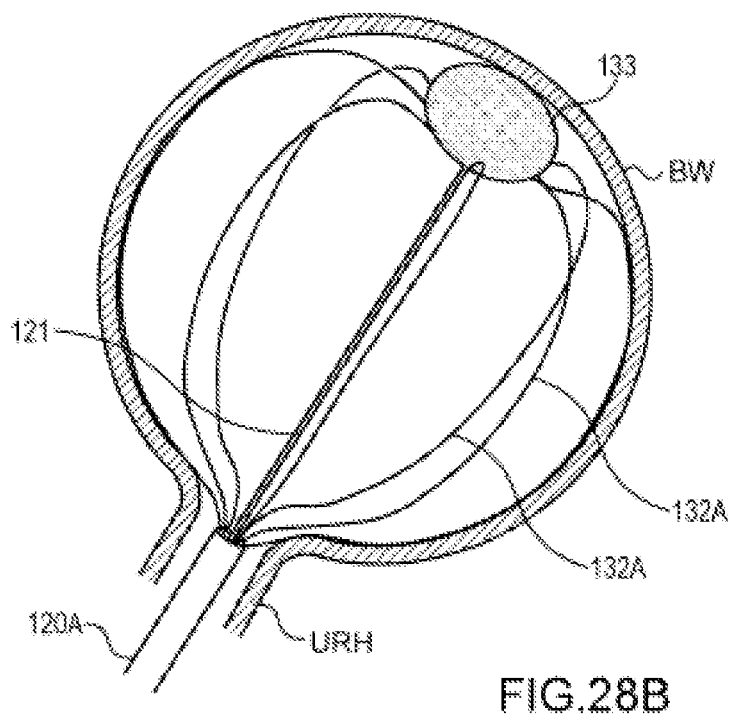
FIG. 28B is a cut-away view of the ablation tool of FIG. 28A expanded against the inner wall of the bladder, according to many embodiments.

FIGS. 28A and 28B show another embodiment in which an ablation tool 1001 comprises a cage-like arrangement of struts or electrodes 132A positioned over an inner shaft 121 and has an inflatable balloon 133 at the distal tip of the inner shaft 121. The inner shaft 121 is advancable and retractable within the outer shaft 120A. As the ablation tool 100I is advanced through the urethra URH, the inflatable balloon 133 can prevent the distal tips of the cage-like arrangement of struts or electrodes 132A from causing injury or perforation of the bladder. The ablation tool 1001 can also be advanced so that the inflatable balloon 133 contacts the bladder dome. The contact between the inflatable balloon 133 and the bladder dome can facilitate finding the right depth of insertion of the device. Also, the balloon 133 can act as an anchor. Further, the balloon can provide a counter force to the struts 132A while they are being pushed into the bladder and can help them better orient in the appropriate curve aligned with the bladder curvature.

FIG. 28A is a side view of the bladder and the ablation tool 1001 before the inflatable balloon 1331 is inflated. The ablation tool 100i is shown in FIG. 28A as partially inserted into the bladder. In FIG. 28B, the bladder has been inflated, the ablation tool 100I is advanced until it reaches the dome of the bladder, and the struts 132 are pushed into the bladder so that they make contact with the inner wall of the bladder. The balloon 133 can be inflated through the inner lumen of the inner shaft 121 positioned in the center of the cage-like arrangement of struts 132a. Once positioned against the inner wall of the bladder, the electrodes or struts 132 can be energized to create a pattern of longitudinal ablation lines as shown, for example, in FIG. 13.

Figure 29A:
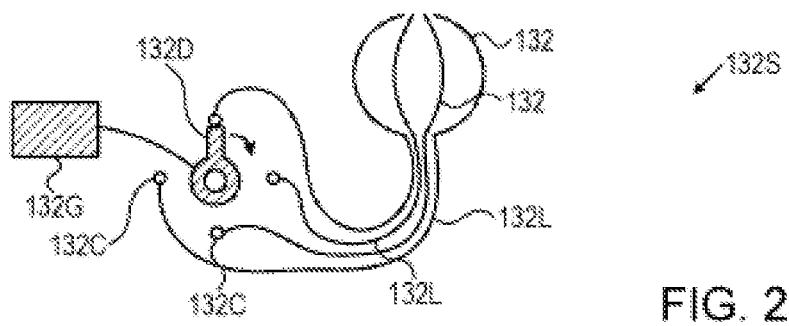
FIG. 29A is a schematic drawing of an electrical system of an ablation tool, according to many embodiments.

In many embodiments, an ablation tool having multiple electrodes may alternate ablation between different electrode segments. FIG. 29A is a schematic drawing of an electrical system 132S which can be used with many of the ablation tools described herein such as ablation tool 100. The system 132S comprises a plurality of electrodes 132 powered through a plurality of electrode leads 132L ending at contact points 132C. The system 132S comprises a mechanical distributor 132 that is used to alternate the ablation energy between the electrodes 132. A power generator 132G is connected to a mechanical distributor arm 132D which rotates and touches different electrode contact points 132C, delivering energy to individual electrodes 132 at different moments. The speed of rotation and the width of the arm or contacts of the distributor 132D can be altered to control the timing of energy delivery. The mechanical distributor arm 132D can be rotated by an electric motor. In other embodiments, a non-mechanical electrical system using electronic switches may be used to alternate energy delivery amongst individual electrodes 132.

Figure 29B:
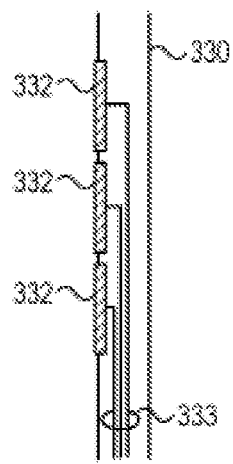
FIG. 29B is a schematic drawing of a set of electrodes positioned on a non-conductive struts, according to many embodiments.

FIG. 29B is a schematic representation of a strut 330 which can be used with many of the ablation tools described herein such as ablation tool 100. For example, one or more of the struts 330 can be disposed over the balloon 110 of the ablation tool 100 to contact the inner wall of the hollow organ. The strut 330 is attached to separate conductive areas 332 acting as ablation electrodes. Each such electrode 332 is connected via an insulated wire 333 to an electrical distributor such as the mechanical distributor arm 132D discussed above. Thus, ablation energy can be alternated between conductive areas 332.

Figure 29C:
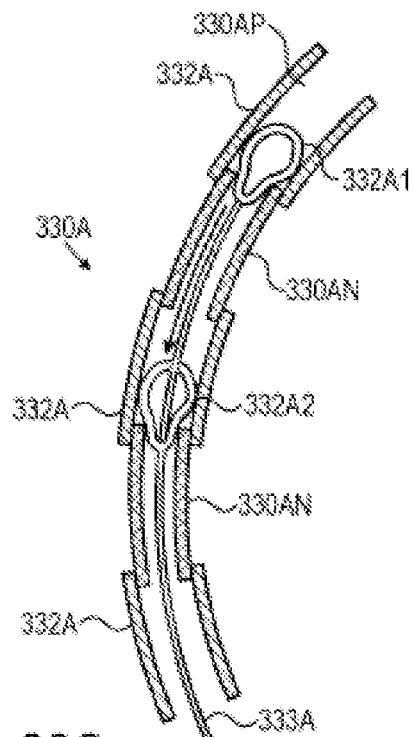
FIG. 29C is a schematic drawing of a strut having a set of alternately electrically conductive and non-conductive segments, according to many embodiments.

FIG. 29C is a schematic representation of another strut 330A which can be used with many of the ablation tools described herein such as ablation tool 100. For example, one or more of the struts 330 can be disposed over the balloon 110 of the ablation tool 100 to contact the inner wall of the hollow organ. The strut 330A can comprise a wire 333A running through a passageway 330AP inside of the strut 330A. The wire 333A comprises insulated segments and non-insulated contact points having a flexible widening at its distal end. The strut 330A comprises conductive segments 332A and non-conductive segments 330AN. The non-conductive segments 330AN are slightly narrower than the conductive segments 332A. The wire 333A may be pulled through the passageway 330AP of the strut 330A and due to the shape and width of the passageway 330AP will get temporarily stuck at the distal end of each non-conductive segment 330AN, while remaining in contact with the conductive segment 332A. If pulled more forcefully, the contact will "give" and pass through the narrow segment, until the wire 333A becomes "stuck" again at the next narrowing.

In use, the strut 330A may be provided with the wire 333A contacting at the most distal position in the passageway 330AP. After deployment of a device in the bladder having one or more struts 330A disposed thereon, ablation is performed at the first conductive segment 332A1. The user then pulls the wire outwards until the stop at the next segment 332A2 to conduct ablation. The process is repeated for all segments 332A.

Aspects of the present disclosure also provide devices to assess or treat urinary disorders in a bladder or other hollow bodily organ. Such a urinary disorder assessment or treatment device will typically comprise an expandable member such as a balloon, multiple electrodes, and struts that hold the electrodes. The length of struts pulled into the bladder may be independently determined by the shape of the bladder. Alternatively or in combination, the balloon may be longitudinally displaced from the struts so as to reduce the pressure the balloon applies to the struts at their point of entry into the bladder. Alternatively or in combination, the balloon may be separated from the struts at their point of entry into the bladder by a rigid shaft. Alternatively or in combination, the wiring along the struts may originate partially from the distal end of the struts and partially from the proximal end of the device. Alternatively or in combination, the struts may originate at the distal end of the device, and may be embedded in a non-elastic fabric at their origin. Alternatively or in combination, the distal part of the balloon may inflate before the proximal part. Alternatively or in combination, the balloon may have variable compliance, with the distal part of the balloon having higher compliance than the lower part of the balloon. Alternatively or in combination, the struts may be divided into segments separated by lines of increased bending flexibility. Alternatively or in combination, the struts may be divided into segments connected by hinges. Alternatively or in combination, the device may further comprise a pressure controller that maintains a stable bladder pressure and/or stable bladder volume while the expandable member is being expanded. Alternatively or in combination, the device may further comprise a pressure controller that maintains a stable bladder pressure and/or stable bladder volume while the expandable member is being retracted. Alternatively or in combination, the balloon of the device may be made of non-compliant material. Alternatively or in combination, the device may further comprise a temperature controlled fluid circulation apparatus to fill the expandable member with cold fluid. Alternatively or in combination, the struts may further comprise inflatable channels on the side of the strut that is opposite to the bladder wall. Alternatively or in combination, the struts of the device may further comprise a channel on the side of the strut that is opposite to the bladder wall, and the channel may be filled with air or cold fluid for thermal isolation of the strut from the balloon.

Aspects of the present disclosure also provide methods to treat urinary disorders in a bladder. Such a method may comprise the steps of deploying an expandable member such as a balloon to appose multiple electrodes to the bladder wall, stimulating the bladder to contract (such as by applying cold water, rapidly increasing bladder pressure, or applying a pharmacological agent), and applying ablative energy to preferentially ablate areas that were responsive to the contractive stimuli. Alternatively or in combination, areas that were responsive to the above stimuli may be localized. Alternatively or in combination, ablative energy may be applied to preferentially electrically isolate areas that were responsive to the contractive stimuli.

Aspects of the present disclosure also provide devices to assess or treat urinary disorders. The devices may comprise an expandable member or balloon. The internal side of the balloon may further comprise a pattern, such as dots or a grid adapted to identify zones of increased and/or early bladder contraction. The pattern may be visible and may be observed by an endoscopic camera. The pattern may be radiopaque and may be visualized by fluoroscopy. Fluoroscopy may be timed with bladder pressure change.

Aspects of the present disclosure also provide devices to assess or treat urinary disorders. Such urinary disorder assessment or treatment devices may comprise a laser range finder to detect bladder activity.

Aspects of the present disclosure also provide methods to assess or treat urinary disorders. Such methods may comprise steps of creating at least one magnetic field near the patient and deploying at least one coil element in the bladder. The electromagnetic signals and/or currents in the coil element may be used for the localization of bladder activity.

Aspects of the present disclosure also provide devices to assess or treat urinary disorders where at least one magnetic field is created near the patient and at least one coil element is deployed in the bladder. The electromagnetic signals and/or currents in the coil element may be used for the localization of bladder activity. The coils may be deployed on a non-elastic balloon. Alternatively or in combination, the coils may be deployed on struts that hold the coils. The length of struts pulled into the bladder may be independently determined by the shape of the bladder. Alternatively or in combination, the coils may be placed on a flexible longitudinal element that is introduced into the bladder. The element may have a length that is at least 3 times longer than bladder diameter. Alternatively or in combination, some of the coil elements used for localization can be preferentially disconnected from electrical circuitry to minimize interference between adjacent coils.

Aspects of the present disclosure also provide devices comprising a plurality of electrodes and an apparatus to measure impedance. The impedance measured with the electrodes may be used to assess bladder activity. Alternatively or in combination, the impedance measured with the electrodes may be used to locate areas for optimal radiofrequency ablation to treat overactive bladder. Alternatively or in combination, the apparatus to measure impedance may measure the impedance of the electrode and the devices may further comprise an apparatus to measure intravesical pressure, and the changes in impedance that occur concurrently to significant changes in bladder pressure may be used to assess bladder activity. Alternatively or in combination, the adjacent bladder activity may be interpreted according to the concurrent impedance changes in other electrodes of the device. Alternatively or in combination, the adjacent bladder activity may be interpreted according to the initial impedance value of the electrode.

Aspects of the present disclosure also provide apparatuses for creating an ablation pattern in a urinary bladder. Such an apparatuses will typically comprise a shaft and a balloon, where the balloon surrounds a distal part of the shaft and the shaft is telescopic in this part. The telescopic shaft may vary from 2 cm to 5 cm when collapsed to 4 cm to 15 cm when fully extended. The force needed to change the length of the telescopic may vary according to the pressure in the balloon.

Aspects of the present disclosure also provide apparatuses for creating an ablation pattern in a urinary bladder. Such an apparatus will typically comprise an expandable balloon and ablative wires, where the outer surface of the wires is conductive in at least parts of the wire. Ablation may be performed during expansion of the balloon. The balloon may be partially deflated between ablations. The volume of the balloon may be periodically changed by 5% to 50% over the course of 10 to 50 seconds.

In many embodiments, the wires are parallel to the long axis of the device. The apparatus may further comprise transverse wires that connect between adjacent longitudinal wires. The transverse wires may be connected to a longitudinal wire at their distal end and only partially connected to an adjacent wire proximally, allowing sliding of the wire through the latter connection. The transverse wires may run along the equator of the balloon. The transverse wires may run at the circumference of the balloon at latitude that is approximately halfway between the equator and the pole of the balloon. The wires may comprise bundles of wires, each having it surface conductive at a different part. Inflation of the balloon may cause deployment of the wires over the balloon surface. The wires may be pulled back by spring loaded rings located over the proximal part of the shaft. The device may further comprise a slidable radially expandable collar enabling safe and easy retraction of the expandable member and electrode structure. The collar may be located proximal to the balloon during insertion and distal to the balloon after retraction.

Aspects of the present disclosure also provide apparatuses for creating an ablation pattern in a urinary bladder comprising of a cage like apparatus. The volume of the cage may be set, and the bladder may then be drained to a volume that is 5% to 50% less than that volume. In some embodiments, the apparatus may comprise two cage-like devices, one inside the other. The limbs of one cage may be parallel to the long axis of the device and the limbs of the other cage may be distorted to intersect with the limbs of the first cage.

Methods and apparatuses to apply the transurethral bladder partitioning therapy are now described in more detail. It is understood that individual therapeutic elements may address at least one aspect of a therapy. An individual therapeutic element may be attributed to an individual aspect of the therapy for convenience only and might relate also to other aspects of therapy.

Ensuring Effective Contact of the Electrodes with the Bladder Wall.

In some embodiments, structural elements of the device 100 are provided to ensure good contact of the electrodes 132 with the bladder wall BLW, while anticipating various bladder shapes that are not substantially spherical.

In some embodiments, the apparatus 100 is comprised of the following parts: the shaft 120, the expandable member 110, an array of electrodes 132, and stripes of material or struts 330 to house the electrodes 132. The shaft 120 may comprise a tubular member which may have an outer diameter between 1 mm to 8 mm. The expandable member 110 may comprise, for example, a balloon, elastic cage, shape memory alloy, fluid absorbing material, etc. In some embodiments, the struts 330 act as the expandable member 110 or vice versa (the expandable member 110 houses the electrodes 132).

In some embodiments, the strut 330 further comprises a channel 350 which may be filled by gas or fluid to improve strut structural stability and/or create thermal isolation. In some embodiments, the device 100 further comprises a small balloon (which may be Foley catheter like, with a volume of 3 cc to 20 cc), which may be used to seal the bladder outlet, to help localize the position of the device 100, and/or to keep an ablation catheter at a distance from the bladder neck. In some embodiments, the small balloon is located 3 cm to 10 cm from the distal tip of the catheter. In some embodiments, after the device 100 is inserted into the bladder BL, the device 100 is pulled back until this balloon is lodged in the bladder neck.

In some embodiments, the shaft 120 houses other parts, facilitating introduction into the bladder BL, and is later at least partially retracted to expose the other components. In some embodiments, the device 100 is built without a main shaft 120, with the various other components providing the necessary longitudinal rigidity to introduce the device into the bladder BL through the urethra URH.

Figure 30A:
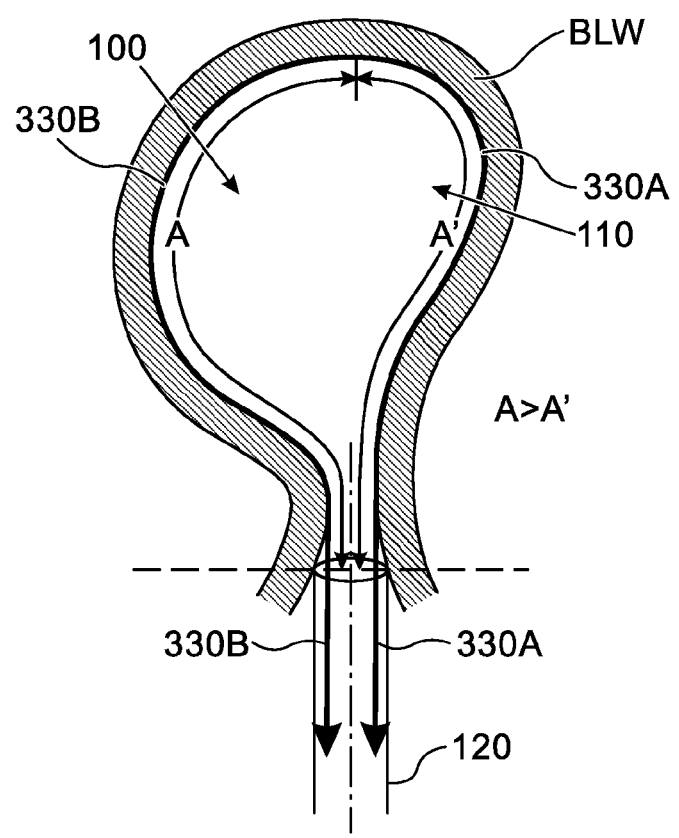
FIG. 30A is a cross-sectional side view of an ablation device with variable length struts advanced into a bladder, according to many embodiments.
Figure 30B:
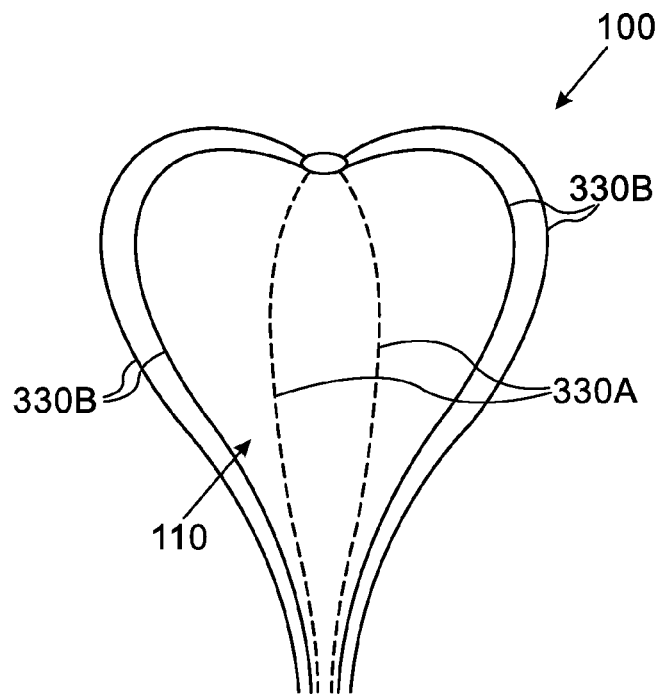
FIG. 30B is a cross-sectional side view of an ablation device with struts arranged in a heart shape, according to many embodiments.
Figure 30C:
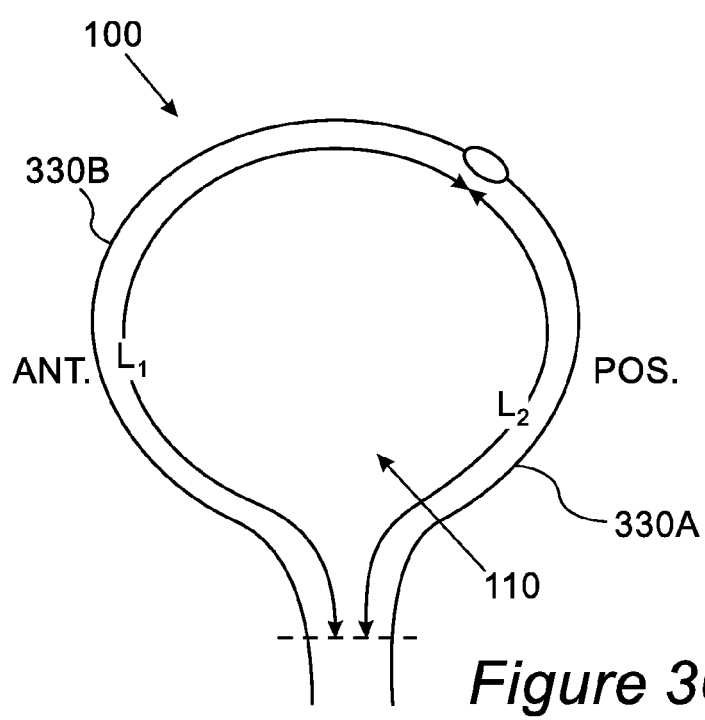
FIG. 30C is a cross-sectional side view of an ablation device with longer and shorter struts, according to many embodiments.

In some embodiments, the length of the strut 330 inside the bladder BL is variable. In some embodiments, the struts 330 are free to be inserted into the bladder BL to various degrees. In some embodiments, shown in FIGS. 30A to 30C, for example, shorter struts 330A and longer struts 330B are used, as needed. For example, if the shape of the bladder BL is asymmetrical so that the posterior (POS) meridians are shorter than the anterior (ANT) meridians: longer struts 330B (or more of the strut 330B) will be placed anteriorly and shorter struts 330A (or less of the strut 330A) posteriorly, as shown in FIG. 30C. In some embodiments, the length of each strut 330 is determined by the operator, effectively allowing the operator to control the final shape of the struts 330 and the expandable member 110, as shown in FIG. 30A. For example; if the posterior struts 330A are set by the operator to be shorter than the anterior struts 330B, the final shape of the expandable member 110, dictated by the struts 330A, 330B, will be asymmetrical with the anterior meridians being longer than the posterior meridians.

In some embodiments, the operator determines the length of each strut 330 that is introduced into the bladder BL by first imaging the bladder (by US, fluoroscopy, CT, or the like), and then choosing the lengths needed to shape the device 100 to conform with the specific bladder anatomy. For example, if imaging of the bladder BL shows that the bladder of the particular person to be treated is "heart shaped", two opposing struts 330A will be set to be somewhat shorter, while the rest of the struts 330B will be set to be longer, causing the expandable member 110 to assume a "heart" shape, to better conform with the anatomy of the bladder as shown in FIG. 30B.

In some embodiments, the length of some of the struts 330 that is introduced into the bladder BL is pre-fixed, while other are allowed to be pulled into the bladder BL freely. FIG. 30A shows a cross section of the device 100 according to such embodiments, where the strut 330A with a length marked as A' is set to a certain length (at a pre-set length it is stopped from being further pulled into the bladder BL), and the opposing strut 330B with a length marked A is allowed to be pulled into the bladder BL freely. As a result, the length of strut 330B that is inside the bladder BL is longer than the length of strut 330A inside the bladder BL. As a result the balloon 110 is forced by the struts 330A, 330B to the shape shown.

Figure 31:
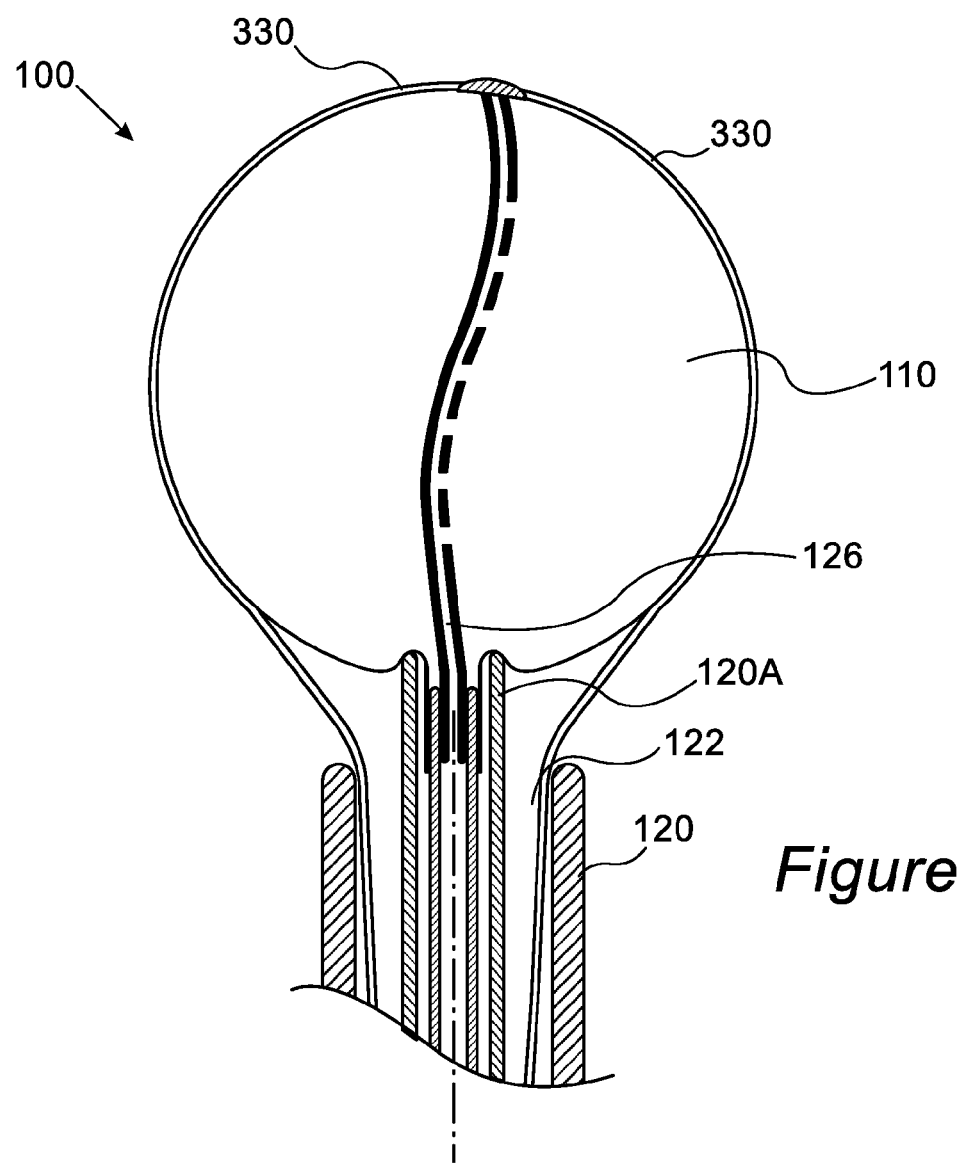
FIG. 31 is a side view of an ablation device having an inner shaft to separate an expandable member and struts, according to many embodiments.

To facilitate the free pulling of the struts 330 into the bladder BL, the device 100 may be configured to minimize the friction between the struts 330 and the device shaft 120 and/or the body, such as shown in FIG. 31. In some embodiments, the balloon member 110 and the electrode structure 132 are separated within the shaft 120 of the device 100, such as with an internal shaft 120A disposed within the lumen 122 of the shaft 120 as shown in FIG. 31, so that inflation of the balloon 110 does not press the struts 330 against the shaft 120 of the device 100, reducing friction between the struts 330 and the shaft 120. In some embodiments, as shown in FIG. 31, the point where the struts 330 exit the shaft 120 of the device 100 is proximal to the point the balloon 110 is connected to the shaft 120 of the device 100. In some embodiments, as shown in FIG. 31, the expandable member 110 is pushed out of the device shaft 120 prior to expansion, so that the most proximal part of the expandable member 110 is still distal to the point where the struts 330 leave the shaft 120.

Figure 32:
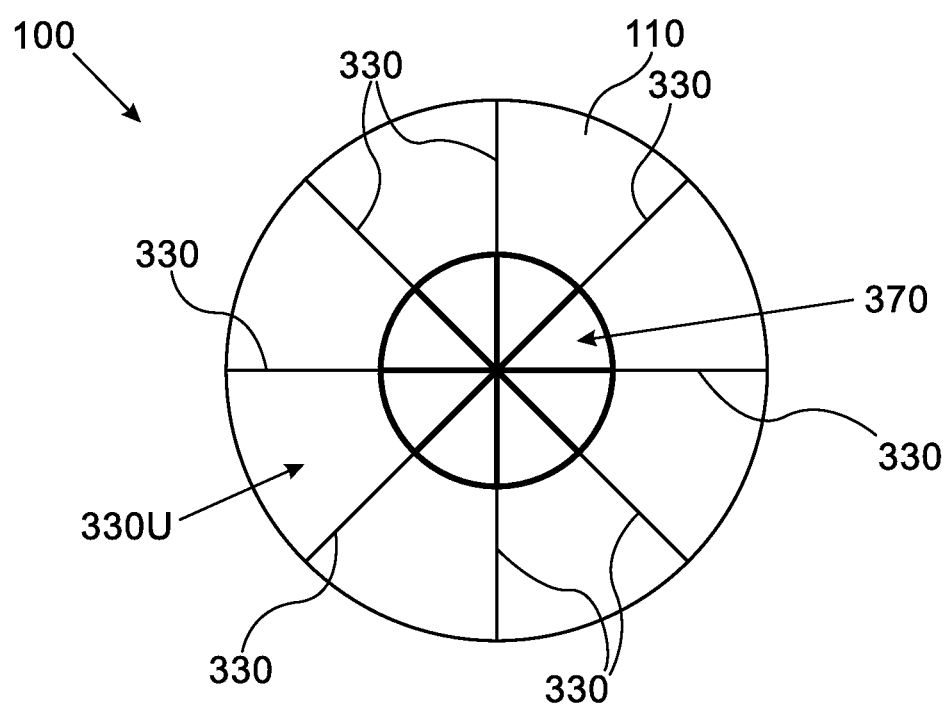
FIG. 32 is a top view of an ablation device with struts arranged in the manner of an umbrella, according to many embodiments.

FIG. 32 shows the device 100 from a top view according to many embodiments. In some embodiments, as shown by FIG. 32, the struts 330 are guided on the balloon or other expandable member 110 to maintain a relatively fixed distance between each other. In some embodiments, as shown by FIG. 32, the origin of the struts 330, at the distal part of the device 100, is embedded in an umbrella like structure 330U, providing stable and relatively rigid contact with the dome of the bladder BL, (allowing the device 100 to be safely pushed into the bladder BL while minimizing risk of perforation) and keeping the struts 330 at fixed angles to each other. In some embodiments, as shown by FIG. 32, this umbrella like structure of the struts 330U is achieved by the inflation of a balloon 110 (inflation of the balloon 110 provides the force needed to open the umbrella 330U). In some embodiments, as shown by FIG. 32, the origin of the struts 330 is embedded in a non-elastic fabric or material 370. In some embodiments, as shown by FIG. 32, there are between three to twenty four struts, fanned at angles of between 120 to 15 degrees.

FIGS. 33A to 33D show an exemplary balloon 110 of the device 100 being expanded from a fully deflated state (FIG. 33A), to a 30% inflated state (FIG. 33B), to a 60% inflated state (FIG. 33C), and to a 100% or fully inflated state (FIG. 33D). In some embodiments, the balloon 110 is designed with variable compliance, so that the top (distal) part of the balloon 110 inflates before the bottom (proximal) part, to facilitate the deployment of the variable length struts, as shown in FIGS. 33A to 33D. In some embodiments, this variable compliance will result in a final balloon shape that is not spherical, such as "pear" shaped as shown in FIG. 33. In other embodiments, the compliance of the various parts of the balloon 110 equals out at full deployment pressure, so that when fully deployed, the balloon assumes a spherical shape. In other embodiments, this pattern of inflation is achieved by pre-shaping of the balloon 110 rather than by a variable compliance along the balloon. Such a pre-shaped balloon 110 may include a large hole in the balloon (like the hole in a bagel), with the hole located more to the proximal part of the balloon. In other embodiments, this preferential inflation is achieved by partially leaving the balloon 110 within the shaft 120 during inflation, and gradually retracting or retrieving the shaft 120 allowing the distal part to inflate before the proximal part.

Figure 34C:
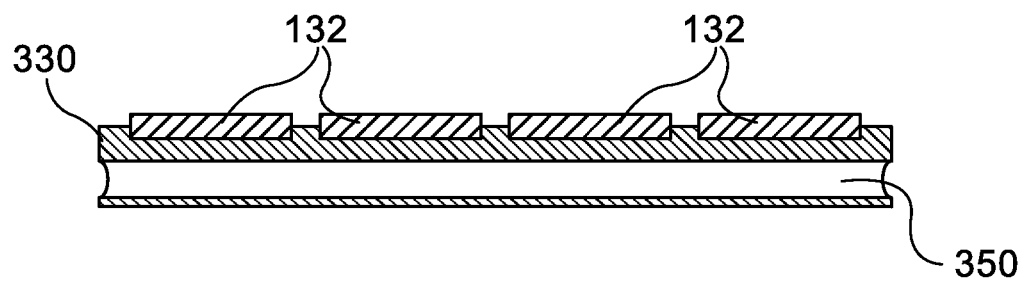
FIG. 34C shows a cross-section of a strut of an ablation device carrying multiple electrode segments, according to many embodiments.

As shown in FIGS. 34A and 34B, in some embodiments, the struts 330 carrying the electrodes 132 comprise multiple segments 330S connected by hinges 330H, practically creating a chain, or continuous track, to better accommodate to the surface of the bladder. FIG. 34A shows a series of strut segments 330S each connected to one another with a single pivoting element. FIG. 34B shows a series of strut segments 330S each connected to one another with multiple pivoting elements. Alternatively, a variety of single and multiple pivoting elements may be used. In other embodiments, lines of reduced resistance cross the struts at regular intervals, creating points of increased flexion, act as effective hinges. As shown in FIG. 34C, the strut 330 may carry multiple electrodes 132 and comprise a channel 350.

In some embodiments, to deploy the electrodes, the bladder BL is first filled to a predefined volume (e.g. 250 cc), and only then is the balloon 110 deploying the electrodes 132 inflated. This approach can help to ensure the deployment of the electrodes 132 is optimal by preventing changes to bladder wall or shape while deploying. In these embodiments, the volume within the bladder BL is kept stable while the expandable member 110 is being expanded. This volume stabilization can be achieved by filling the balloon 110 with fluid removed from the bladder BL or by removing from the bladder equivalent volumes to the volume being filled into the balloon 110.

In some embodiments, the balloon 110 used to deploy the struts 330 carrying the electrodes 132 are made of a material that is non-elastic, such as Nylon, Pebax (polyether block amide.), PET (Polyethylene terephthalate), EVA (Ethylene-vinyl acetate), cellophane, etc. The potential size of the balloon 110 may be larger than the volume of the bladder BL, thus when the balloon 110 is deployed, folds on the surface of the balloon are formed. This balloon 110 may be used in order to maintain the position of the electrode 132 relative to the bladder BL (once in contact with the bladder BL), even if the overall shape of the balloon changes (in inflation or deflation). In some embodiments, this type of balloon 110 is used to minimize undesirable tangent forces that might act between the balloon 110 and the struts 330, forces that might distort the balloon 110 or cause it to puncture. (For example, if an elastic balloon 110 is used, at a certain point the struts 330 might be compressed between the balloon 110 and the bladder wall BLW, but then the balloon 110 might continue to expand and stretch. In this case, undesirable tangential forces will result along the strut 330.)

In some embodiments, the temperature of the fluid in the balloon 110 is changed from body temperature to cold, only after the electrodes 132 were already deployed. This temperature change may be used to cause contractions of the bladder wall BLW against the array of electrodes 132, to improve contact with the array of electrodes 132 and preferentially augment the ablation of contracting areas. (Cold water is known to induce bladder contractions.) In other embodiments, other techniques are used to cause contraction of the bladder against the electrodes, including: rapid stretch of the bladder, electrical current at frequency between 1 to 100 HZ, infusion of a smooth muscle contracting agent such as carbachol and the like.

In some embodiments, induction of bladder contractions is further used to preferentially ablate the areas of the bladder that are fast to respond to the above stimuli. In some of these embodiments, the array of electrodes 132 may first be deployed to contact the bladder BL, and then retracted minimally, such that when the bladder BL contracts only the contracting areas come into effective contact with the electrodes 132.

In some embodiments, many short electrodes 132 (e.g., 0.5-2 mm long) are used per strut 330 wherein the device 100 activates only the struts determined to be in good contact with the tissue (as determined by impedance or other methods known in the art.) In some embodiments, the device 100 comprises a significant redundancy in electrodes 132, so that only those with the best contact are used, typically no more than 75% of the electrodes 132. In some embodiments, the electrodes 132 are arranged in parallel, so that every strut 330 actually comprises two or more electrode 132 lines, parallel and in close proximity. In this arrangement, even if many of the electrodes 132 cannot be used (due to compromised contact with the bladder wall BLW, or other reason), other, parallel electrodes 132 can be used to promise effective scar lines.

In some embodiments, the bladder BL is filled with fluid or gas to a volume that best fits the volume of the expandable member 110 when expanded. For example, if a person has a bladder BL that can be filled up to 600 cc and drained to a minimal volume of 50 cc, fluid is instilled into the bladder BL until reaching a volume of 400 cc, the volume of the device 100 when fully expanded.

In other embodiments, the bladder BL is filled until a substantially spherical shape is achieved, regardless of volume. This filling may be done since the urinary bladder BL at different volumes may have different shapes, but when filled enough, most of the bladders will reach a substantially spherical shape at one volume or another.

Safely Detaching the Device from the Bladder Wall BLW (after Ablation).

In some embodiments, to remove the electrodes 132 (remove the device 100 from the bladder BL once ablation is done), the bladder BL is maintained full (e.g. 250 cc), and only then is the expandable member 110 deploying the electrodes 132 collapsed, and the electrodes 132 detached from the bladder wall. This approach may help to ensure the detachment of the electrodes 132 is optimal by preventing changes to bladder wall BLW or shape while detaching. For example, in the situation where one or more of the electrodes 132 becomes "stuck" to the bladder tissue following the ablation, collapsing the expandable member 110 will pull on the bladder tissue at these adhesion points and might cause pinching of bladder tissue within the collapsing device. However, when the embodiments described above are applied, the bladder BL is kept from collapsing by maintaining bladder volume during the collapse of the expandable member 110. In these embodiments, the volume of the bladder BL is kept stable, by filling the bladder BL with fluid from the balloon 110, or by filling the bladder BL with volumes equivalent to the volume being removed from the balloon BL. The bladder BL is then emptied, only after electrodes 132 have been detached and retracted back into the device 110. In some embodiments, in order to remove the electrodes 132, the bladder pressure is first increased and the bladder volume increased to disconnect the electrodes 132 from the bladder wall BLW. In some embodiments, the increased bladder pressure causes decreased expandable member volume, facilitating detachment of the electrodes 132 from the bladder wall BLW. In some embodiments, the expandable member volume is kept stable, while only the bladder volume increases (again detaching the electrodes from the bladder wall).

In some embodiments, the retraction of the device 100 and/or the extraction of the device 100 from the bladder BL is performed only after the disconnection of the electrodes 132 is verified by impedance test and/or by capacity tests. In some embodiments, to remove the electrodes 132, the bladder BL is first inflated (filled) with an insulating fluid (such as glycerol), so that when an electrode is not in direct contact with the bladder wall, the impedance will rise greatly and thus disconnection can be easily verified.

In some embodiments, in order to facilitate detachment of the device 100, the expandable member 110 is further expanded, while the struts 330 are not allowed to further expand. This will cause the expandable member 110 to bulge between the struts 330, to push against the bladder wall BLW, and to effectively detach the struts from the bladder wall BLW.

It is often important to protect the balloon 110 from the ablation energy. In some embodiments, the balloon 110 is inflated with cold water, to protect the balloon 110 from heat generated by the electrodes 132. In some embodiments, the temperature of the fluid is set to be above the cold pain threshold, at approximately 15 degrees Celsius. In some embodiments, the fluid temperature is set to be lower, between 15 to zero degrees Celsius, such as 4 degrees Celsius.

Creating ablation lines that are latitudinal to the bladder axis (the longitudinal axis being from head to feet), or at least have a significant latitudinal vector.

Bladder transection surgeries, or in their previous name, bladder myotomies, were extensively performed in the 1960's and 1970's. In these surgeries, circumferential surgical incisions were created along the bladder periphery, to treat overactive bladder symptoms. (Parsons K F: A Further Assessment of Bladder Transection in the Management of Adult Enuresis and Allied Conditions. British Journal of Urology (1977), 49, 509-514). It is believed by the inventors, without being bound by theory, that latitudinal lines may better mimic these bladder transection surgeries and provide improved clinical results. Thus, in many embodiments, devices and methods are described to create such lines of ablation, even though these are more technically demanding than the creation of longitudinal ablation lines (along the long axis of the bladder and along the axis of the device).

In some embodiments, the electrodes 132 are free to rotate around the shaft 120 of the device 100. In some embodiments, this rotation is applied to accomplish spiral like lines. In some embodiments the rotation is applied while the expandable member 110 is being expanded. In some embodiments the electrode struts 330 are coiled over the expandable member 110 before the expandable member 110 is being expanded.

In some embodiments, each strut 330 is coiled around the circumference of the expandable member 110 more than once. In some embodiments, a strut 330 is coiled around and along the expandable member 110 or a shaft 120, creating a three dimensional spiral. FIGS. 35A1 and 35A2, for example, shows side views of a strut 330 wrapped around the shaft 120 in a spiral or helix at radially collapsed (FIG. 35A1) and radially expanded forms (FIG. 35A2). In order to create the desired ablation lines when the strut 330 is spiraled, the strut 330 is first expanded to form a spiral with a larger diameter (this is achieved by rotation of the strut 330 or the shaft 120, in essence "unwinding" the coiled strut 330), thus the struts 330 and hence the resulting ablation lines will have a latitudinal vector as desired. In some embodiments, the spiral is pressed against the bladder wall to cause the 3D structure (spiral) to create a circular 2D footprint on the bladder.

In some embodiments, the strut 330 is coiled upon itself. Thus, when expanded (achieved by rotation of the strut 330 or the shaft 120, in essence "unwinding" the coiled strut 330) the strut 330 may cover a larger circumference, thus achieving the desired latitudinal axis vector. FIGS. 35B1 and 35B2, for example, show top views of a shaft 120 having a strut 330 wrapped around the shaft 120 in a spiral or helix in radially collapsed (FIG. 35B1) and radially expanded forms (FIG. 35B2).

In some embodiments, a latitudinal strut 330 structure is used more than once, to create more than one latitudinal circle ablation on the bladder wall BLW. In some embodiments, a latitudinal circular strut 330 is used twice: it is used to ablate the circumference of the bladder BL near the dome, and then moved to again ablate the circumference of the bladder BL near the bladder neck.

Figure 36:
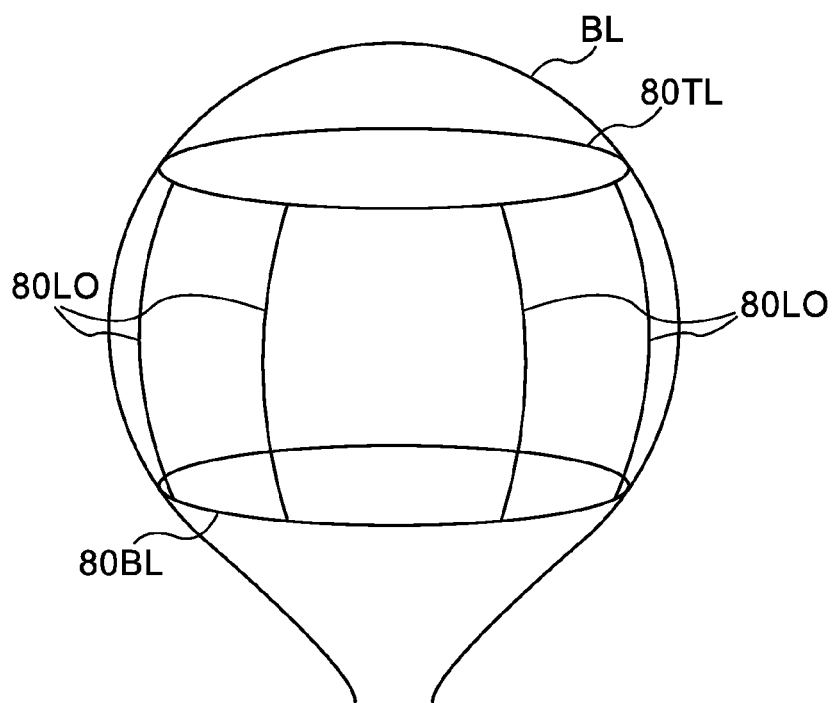
FIG. 36 shows a side, perspective view of a urinary bladder with an ablation pattern which comprises longitudinal and latitudinal ablation lines to create isolated bladder areas, according to many embodiments.

In some embodiments (shown in FIG. 36, for example), longitudinal ablation lines 80LO are then created to extend between latitudinal ablation lines 80TL, 80BL, creating isolated bladder zones between them. For example, if two latitudinal circular ablations 80TL, 80BL are performed, longitudinal ablation lines 80LO extending between these circles will create an isolated bladder area, limited by one circle on the top, the other on the bottom, and one ablation line from each side. FIG. 36, for example, shows the bladder BL with a top latitudinal ablation line 80TL, a bottom latitudinal ablation line 80BL, and a plurality of longitudinal ablation lines 80LO.

Device Design to Minimize the Device Cross Section.

Figure 37:
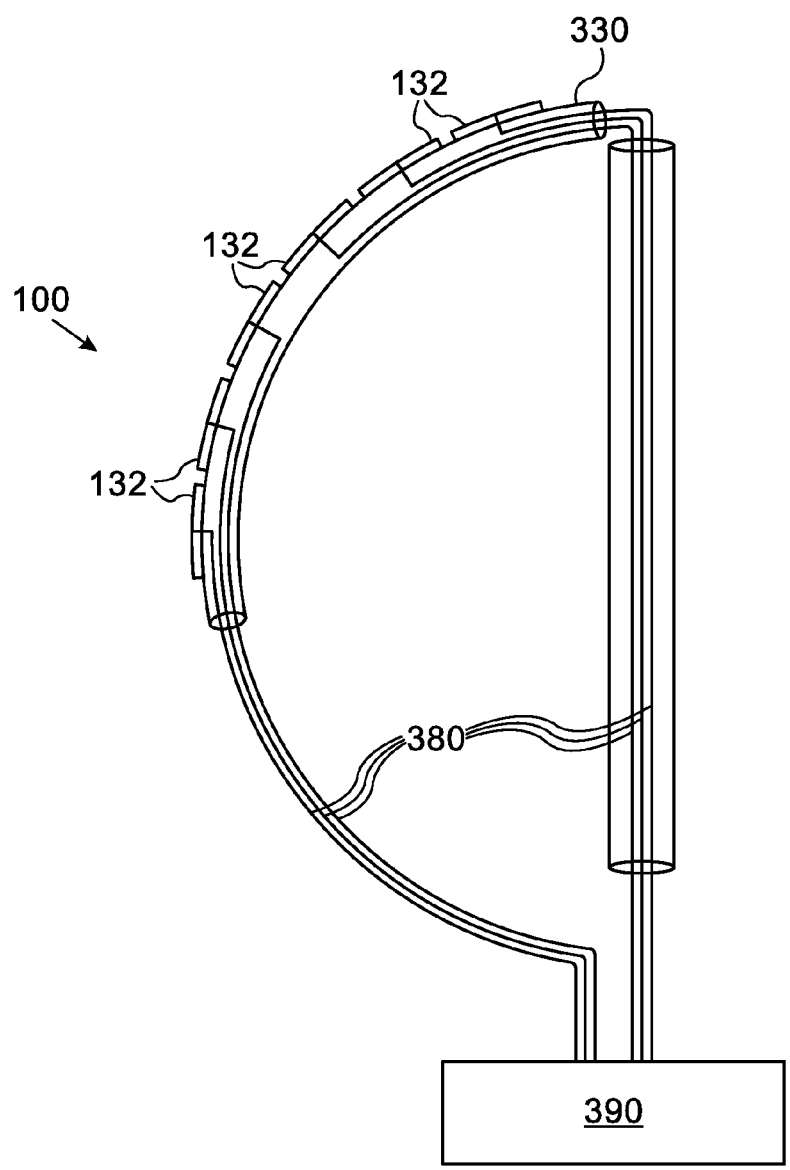
FIG. 37 shows a side view of an ablation device with wiring to power electrodes mounted on struts of the ablation device, according to many embodiments.

As shown in FIG. 37, in some embodiments, the origin of electrical wiring 380 to the electrodes 132 on the strut 330 is divided between the distal part and the proximal part of the strut 330. In this way, some of the electrodes 132 are electrically connected through wires 380 that come from the distal end of the device 100 and some are connected through wires that come from the proximal side of the device 100. Thus, the number of wires 380 passing in the strut 330 at each point is minimized, so to make the strut 330 more compliant and minimize the strut 330 cross section.

In some embodiments, the wiring 380 of most or all the electrodes 132 on the strut 330 is independent. In some embodiments, all or most electrodes 132 on the same strut 330 are connected electrically in parallel.

In some embodiments, two adjacent electrodes 132 are wired to opposite electrical poles, so that one electrode 132 will be an anode while the adjacent electrode 132 will be a cathode. This arrangement allows bi-polar ablation between adjacent electrodes. In some embodiments, the adjacent electrodes 132 are both on the same strut 330. In some embodiments, the adjacent electrodes 132 are each on a different strut 330.

In some embodiments, the strut 330 is made of a very thin material, as thin as possible, even if compromising the structural stability of the strut 330. In some embodiments, the strut 330 further comprises a potential channel on the back side of the strut 330. This channel can be inflated to avoid twisting of the struts 330 and to provide the strut 330 with some structural rigidity despite its thinness. This structural rigidity is often necessary to avoid strut twisting and to facilitate enough pressure of the strut 330 against the bladder wall BLW. In some embodiments, the inflation of the channels replaces the expandable member 110.

Alternatively or in combination, a wire 380 can be passed through the channel to provide structural rigidity. This wire 380 can be passed after the strut 330 is deployed. In some embodiments, the wire 380 above is pre-shaped. In some embodiments, the wire 380 is passed through the channel of struts 330 only if these struts are found to be twisted or dislocated or not in good contact with the bladder wall BLW.

In some embodiments, the channel is used to cool the struts 330 from their backside, effectively protecting the balloon 110 from heat produced by RF ablation at the electrodes 132.

In some embodiments, nitinol wires extend from the distal end of the struts 330, so that they need not be in parallel to the struts, to avoid increasing the diameter of the device when collapsed. Extending from the distal ends of the struts 330, these nitinol wires are used instead of the expandable member 110, to position the struts 330 and the electrodes 132.

In some embodiments, the struts 330 are not passed through the urethra URH in parallel to (or surrounding) the expandable member 110, but rather are passed separately, after (or before) the expandable member 110. In some embodiments, thin strings connect between the distal part of the expandable member 110 and the distal part of the strut 330. In some embodiments, these strings are later (after the expandable member is safely inserted into the bladder) pulled to approximate the distal ends of the expandable member 110 and the struts 330.

Again, in some embodiments, the struts 330 are made as thin as possible, giving up the needed structural rigidity needed to push such an element out of a shaft 120 or against the bladder wall BLW.

In some embodiments, the lack of this structural rigidity is compensated for by pulling the struts 330 behind (i.e., following) the expandable member 110 that does comprise an element of axial and/or radial rigidity.

In some embodiments, the lack of this structural rigidity is compensated for by the use of fluid or gas pressure that "blows" the struts 330 along the shaft 120 and out into the bladder BL.

In some embodiments, the expandable member 110 is not passed at once through the shaft 120; rather, several components are passed one after the other, together expanding into the desired volume. In some embodiments, the expandable member 110 is comprised of balloon elements. In some embodiments, these elements are a chain of balloons that are interconnected. Air or fluid pressure applied to inflate the balloon 110 pushes the most distal balloon 110 out of the shaft 120 and inflates it, while other balloon 110 in line remain deflated because they are still in the shaft 120. The interconnection between the balloons 110 comprises a flexible tube, allowing the balloon chain to become a 3D structure. In some embodiments, the balloon chain is composed entirely of a tube, which is somewhat inflatable. In some embodiments, a plurality of inflatable elements each supporting at least a single electrode are positioned adjacent and parallel to each other.

As shown in FIGS. 38A1 to 38B2, in some embodiments, the struts 330 are inserted into the bladder BL through the bladder neck BN one after the other, to minimize the diameter of the device 100, or namely, to minimize the diameter of the shaft 120 or other channel needed for endoscopic deployment the device 100. As shown in FIG. 38A1, each strut 330 is advanced over a "leading" wire or string 381 that has a significantly smaller diameter than the strut 330 itself. The struts 330 may then be inserted one by one and pushed over the lead wire 381 until the widest part of the strut 330 is within the bladder BL. Then, a second strut 330 can be advanced and so forth before the struts 330 are expanded as shown in FIG. 38A2. As shown in FIG. 38B2, in some embodiments, the shaft 120 has a groove or recess 124 that is adapted to accept the strut 330 and pass it through the urethra URH. As shown in FIG. 38B1, the shaft 120 can then be rotated (e.g., by 45 degrees) and the next strut 330 again advanced on the groove to a different location. As shown in FIG. 38B1, in some embodiments, the lower part of the shaft 120B of the device 100 can be rotated independently from the head of the shaft 120A of the device 100, where the leading wires 381 are connected to the shaft 120.

Figure 39A:
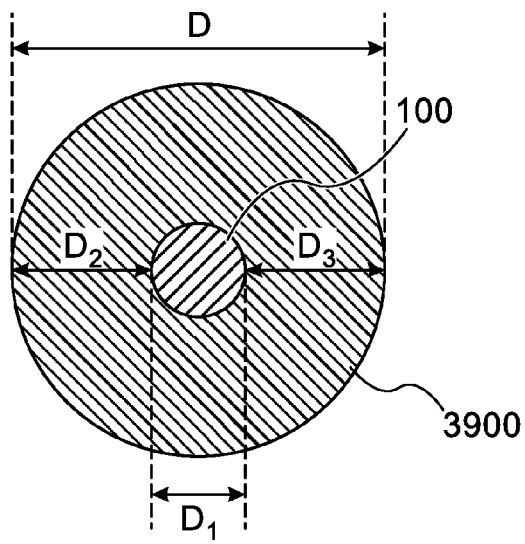
FIG. 39A and FIG. 39B show cross-sectional views of an ablation device configured to be advanced within a cystoscope and an ablation device configured to have a cystoscope advanced therethrough, respectively, according to many embodiments.
Figure 39B:
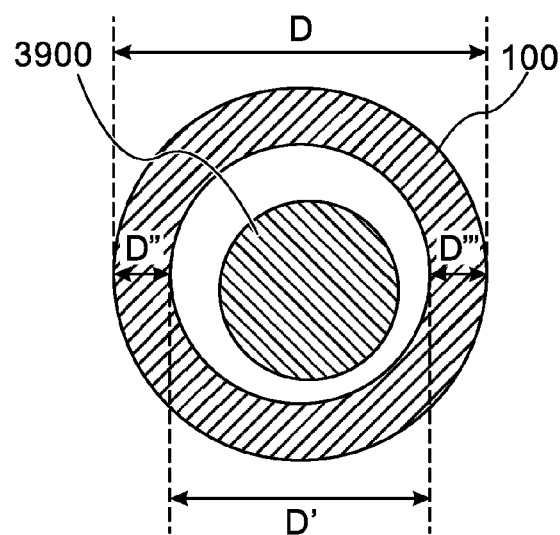

As shown in FIGS. 39A and 39B, embodiments of the present disclosure may also include devices 100 which minimize the overall diameter of the device 100 together with a cystoscope 3900. In these embodiments, instead of inserting the device 100 through the cystoscope 3900 as shown in FIG. 39A, the cystoscope 3900 is inserted through the device 100 (or, the device 100 can be "wrapped" around a cystoscope) as shown in FIG. 39B. Positioning of the device 100 around the cystoscope 3900 can provide the significant benefit of fitting more volume on the same overall device 100 cross section diameter. For example, FIGS. 39A and 39B show that the cystoscope 3900 and the device 100 can have an overall diameter of D. In FIG. 39A, the overall diameter D may comprise D1 (the diameter of the device 100) added to D2 and D3—the width of the cystoscope 3900 from the inner to outer walls. In FIG. 39B, the overall diameter D may comprise D' (the diameter of the lumen of the device 100 through which the cystoscope 3900 is disposed) added to D" and D'"—the width of the device 100 from its inner to outer walls. Even if D1 is equal to D" plus D'", the area or volume of the device 100 shown in FIG. 39A will be smaller than that shown in FIG. 39B. In other words, by positioning the device 100 around the cystoscope 3900 as in FIG. 39B, the volume of the device 100 can be greater than if the device 100 were instead configured to be passed through the inner lumen of the cystoscope 3900 as in FIG. 39A.

In some embodiments, the device 100 has an internal tube like space or lumen that is adapted to accept a cystoscope 3900. In these embodiments, the cystoscope 3900 will extend through the device 100 until the distal end of the cystoscope 3900 extends beyond the device 100. In some embodiments, the cystoscope 3900 extends ~1 cm beyond the device 100. In some embodiments, the tube-like structure or lumen has one or more elements that hold the cystoscope 3900 in place relative to the device 100. In some embodiments, these structures can be "deactivated" to allow changing the relative position of the cystoscope 3900, or removal of the cystoscope 3900. In some embodiments, the tube-like structure is collapsible. In the collapsed position, the tube is pressed against the cystoscope 3900 and so the cystoscope 3900 and the device 100 are mechanically coupled (their positions relative to each other are fixed). When the device 100 is expanded or deployed, the tube-like or lumen structure may be mechanically de-coupled to the cystoscope 3900 so as to allow change of relative position or removal.

In some embodiments, the cystoscope 3900 is mechanically coupled to the device 100 and extends beyond the device 100 for approximately 1 cm during insertion of the device 100 into the bladder BL. In some embodiments, the cystoscope 3900 is not mechanically coupled to the device 100 during deployment, to allow rotation of the cystoscope and for visualization of the device 100 placement within the bladder BL.

Achieving Controlled and Predictable Ablations.

As described above ensuring good contact is an important aspect of achieving good quality predictable ablation. However, good contact by itself is often not sufficient. Embodiments of the present disclosure further include devices configured for and methods to further facilitate creation of predictable ablations.

Embodiments of the present disclosure may include a method for creating predictable ablation lines within the bladder. An exemplary method may include a step of filling the bladder BL with a fluid or gas, while monitoring the bladder wall BLW thickness (e.g., by ultrasound). Fluid or gas may be added (or removed), until the bladder wall stretches to a desirable value best fitted for the ablation characteristics of the device 100. An example for such a value may be 4 mm, or a different width in the range of 1 mm to 5 mm. This method may allow adjusting the bladder BL to the ablation rather than adapting the ablation to the bladder, as usually done in other ablations (i.e., cardiac ablations). This method can have several benefits. One benefit is that the monitoring of the ablation may be less crucial (since the tissue thickness is adjusted to be exactly the width that the given ablation ablates best-or is adjusted to be slightly thicker, considering the desired safety margin). Minimizing the need for ablation monitoring can allow making the ablation device simpler, cheaper, and with a smaller diameter (e.g., less need for sensors and the wires needed for their function). Another benefit of this method may be that when the bladder wall BLW thickness desired value is low (e.g. 2.5 mm), the energy required to create the ablation can be reduced and the lesion created can be more uniform (RF ablation intensity and uniformity is known to decrease as the distance from the probe grows). Yet another benefit of this method may be to reduce the blood flow to the bladder wall BLW or adjust the blood flow to an anticipated value. (The blood flow to the bladder wall BLW may change in an expectable manner when the bladder BL volume is increased and decreased).

The urinary bladder BL is located beneath the peritoneum. When the bladder BL is full, the lower parts of the urinary bladder BL are in direct and intimate contact with pelvic organs while the upper parts of the bladder BL (those that are rostral to the peritoneal reflection) are separated from adjacent organs by at least two layers of peritoneum (such as the peritoneal folds PF shown in FIG. 40), and many times fluid film or a more significant volume of fluid. In some embodiments, the lower parts of the bladder are ablated with settings (energy/time/duration) different from those used for the upper parts of the bladder. In some embodiments, more energy is delivered to create ablations in the lower parts of the bladder and less energy is delivered to create ablations in the upper parts.

Figure 40:
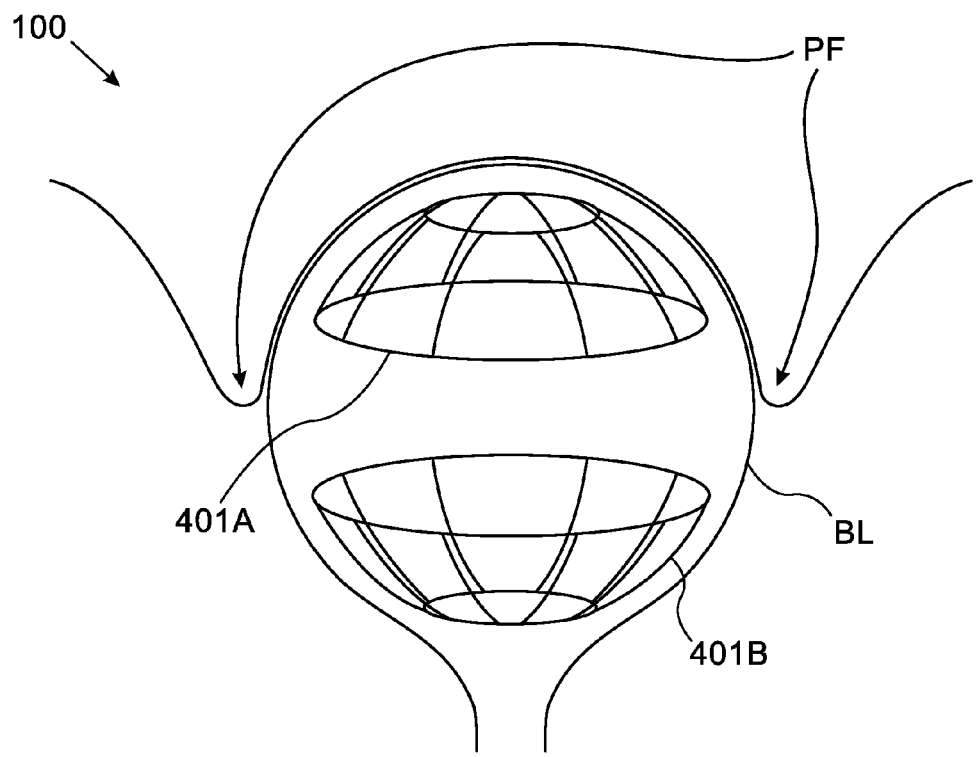
FIG. 40 shows an ablation device configured to generate distinct upper and lower ablation patterns in a urinary bladder, according to many embodiments.

In some embodiments, the device 100 creates two separate ablation patterns (one for each part of the bladder), each pattern comprising more than one isolated bladder area. In some embodiments, these patterns in the device 100 are mirror images of each other. In some embodiments, the same device 100 is used to create both patterns, initially creating the first pattern and then "flipped" to create the mirror image pattern. FIG. 40 shows the bladder BL with an upper ablation pattern 401A and a lower ablation pattern 401B.

Other Energy Sources.

Other methods of creating ablation lines 80 other than using RF energy are also contemplated.

In some embodiments, the ablation lines 80 are created by cryoablation. In some embodiments, the lines 80 of cryoablation are achieved by using an expandable member 110 that has areas that are relatively heat insulating and other elongated areas with higher heat conductance, so as to create cryogenic injuries in specified regions only.

In some embodiments, the expandable member 110 that comes in contact with the bladder wall BLW is carambula (star fruit) shaped, so that only thin areas come in contact with the bladder wall BLW while the rest of the expandable member 110 does not come in direct contact with the bladder wall BLW and is relatively heat insulated by the air space (or fluid space) between the expandable member 110 and the bladder BL.

In some embodiments, the cryoablation probe is located in an expandable member 110 filled with fluid having a freezing point that is below the minimal temperature for permanent tissue damage (i.e., freezing point lower than minus 70 degrees Celsius). In some embodiments, the fluid is circulated in the balloon 110 to facilitate heat exchange with the probe and the bladder wall BLW.

In some embodiments, the fluid in the balloon 110 is partially cooled outside the body and further cooled inside the body by cryoablation probes as known in the art.

The techniques described in the embodiments above are used so that designated areas in contact with the bladder BL can reach tissue-damaging temperatures, while other areas remain insulated and relatively warmer for the duration of the therapy.

Is some embodiments, a liquid with subzero boiling point temperature (e.g., liquid argon) is pressure pumped into an elongated member and is passed through tiny holes into the expandable structure 110. In some embodiments, this passage causes a significant drop in pressure, allowing the liquid to boil.

In some embodiments, the parts of the expandable member 110 as described above are tubes.

In some embodiments, the device 100 comprises two pumps: a high pressure pump compressing fluid into the device and another negative pressure pump to extract the gas from the device 100.

In some embodiments, the shaft 120 used to deliver the above device 100 is water or air cooled, to remove the excess heat caused by removing the gas from the device 100.

In some embodiments, the shaft 120 used to deliver the device 100 can be warmed electrically to protect the urethra from the cold temperature of the device 100.

In some embodiments, the energy applied to create the ablation is electromagnetic energy in the range of visible light or ultraviolet light. In some embodiments, the light is applied from within the bladder BL. In these embodiments, most of the surface of the expandable member 110 will absorb or reflect light, while only relatively thin strips of the expandable member surface will allow the light energy through, to reach the bladder wall BLW and cause the desired linear ablations. In other embodiments, the entire surface of the expandable member 110 is light absorbing or reflective, and the energy for ablation passes to the bladder wall only at areas that are not covered by the expandable member.

Sensing.

Let it be understood that the devices 100 described herein may be used not only to deliver energy to the bladder (e.g., RF energy delivered by the electrodes 132 for ablating the bladder wall BLW) but may alternatively or additionally be used to record bladder activity.

In some embodiments, the electrodes 132 are made of conductive material and adapted to record the electrical activity of the bladder wall BLW, to identify and locate foci of electrical activity and/or contraction.

In some embodiments, the electrodes 132 are made of conductive material and the potential of each electrode 132 is recorded against a common ground (on the body of the subject).

In some embodiments, the electrodes 132 are made of conductive material and the potential of each electrode 132 is recorded against the potential of an adjacent electrode of the same device 100.

In some embodiments, the electrodes 132 are made of conductive material and the potential of each electrode 132 is recorded against the average potential of several electrodes 132 of the same device 100.

In some embodiments, the electrodes 132 are made of conductive material and the ECG signal of the patient is subtracted from the potential recorded by the device 100.

In some embodiments, the potential at one or more of the electrodes 132 is recorded after an excitation (depolarization or cathodic stimulation) signal is passed through other electrodes 132 of the device 100. In some embodiments, after ablation has been applied by the electrodes 132 along a strut 330, a depolarization signal is delivered on one side of a strut 330 and a recording performed on the other side of the strut 330 to verify the tissue below the strut 330 is indeed functioning as an isolation line.

In some embodiments, the electrodes 132 are made of conductive material and the impedance is measured in the electrodes 132 to locate bladder activity. The impedance is measured as a proxy to contact with the bladder wall BLW and/or as a proxy to urothelium thickness. It is assumed there will be variability between the impedances of different electrodes 132 on the same device 100, these differences created by the different qualities of the contact between each electrode 132 and the bladder wall BLW, by the anatomical variations in urothelial anatomy and thickness at different locations and more. However, once baseline values are recorded for each electrode 132 changes in these values will signify bladder activity (changes from baseline).

In some embodiments, such changes in impedance, when occurring simultaneously with changes in bladder pressure are used to localize bladder activity.

In some embodiments, the impedance is expected to drop in an electrode 132 when the adjacent bladder area contracts, signifying improvement of contact with the bladder wall BLW due to pressure applied against the electrode 132. In some embodiments, impedance is expected to rise when remote bladder areas contract, due to distortion of the bladder shape and deterioration of the contact between the electrode and the bladder wall.

In some embodiments, the impedance is expected to rise in an electrode 132 when the adjacent bladder area contracts, signifying an increase in urothelium thickness when the bladder wall BLW contracts. In these embodiments, a decrease in impedance will signify stretching of the adjacent bladder wall BLW, the impedance falling due to thinning of the urothelium.

In some embodiments, an increase or decrease in impedance is interpreted as contraction of contraction of adjacent areas or contraction of remote areas, according to the initial impedance value before the change. If this value is low enough to signify near optimal contact to begin with, any further decrease in interpreted as local stretch of the bladder BL. If this value is high enough to signify suboptimal contact to begin with, any further decrease may be interpreted as improved contact and indicates a contraction of adjacent bladder activity.

In some embodiments, an increase or decrease in impedance is interpreted as contraction of adjacent areas or contraction of remote areas, according to the concurrent impedance changes in other electrodes 132 of the device 100.

In some embodiments, the impedance measurement is performed between one electrode 132 to an adjacent electrode 132 of the same device 100 (e.g., near bi-polar).

In some embodiments, the impedance measurement is performed between one electrode 132 to several electrodes 132 of the same device 100.

In some embodiments, the impedance measurement is performed between one electrode 132 to a remote electrode 132 of the same device 100 (i.e., far bi-polar).

In some embodiments, the impedance measurement is performed between the electrodes 132 and a common electrode acting as ground (i.e., mono-polar measurement).

In some embodiments, the electrodes 132 described above are replaced by pressure sensors sensing local contraction of the bladder BL.

In some embodiments, the recordings mentioned above are performed for more than 5 minutes.

In some embodiments, identification of foci of contraction and or electrical activity found by the recordings above is used to treat over active bladder. In some embodiments, treatment comprises electrical isolation of the foci from the surrounding tissue by creating scar lines that isolate the focus. In some embodiments, such foci are ablated to treat over active bladder.

Figure 41:
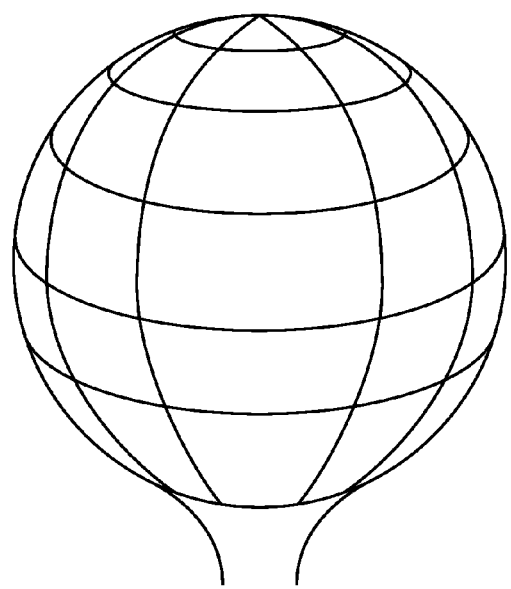
FIG. 41 shows an ablation device configured to have a distinct pattern enabling identification of bladder activity, according to many embodiments.

In some embodiments, the internal side of the balloon 110 further comprises a visible pattern, such as dots or a grid. In some embodiments, such patterns are observed by an endoscopic camera, to identify zones of increased and/or early contraction. As shown in FIG. 41, such contraction may cause visible distortion of the patterns 110P on the balloon, and thus may be identifiable by the user by image processing software.

In some embodiments, the device 100 when deployed exhibits a pattern, such as dots or a grid. In some embodiments, such patterns are created by radio opaque material and observed under fluoroscopy. In some embodiments, the fluoroscopy is timed to contraction of the bladder BL, as identified by increase in bladder pressure.

In some embodiments, electromagnetic fields are created in parts of the device 100, and these fields are monitored to track their movement to exhibit bladder activity.

In some embodiments, the device 100 when deployed exhibits a pattern created by hypoechogenic or hyperechogenic material or zones and observed under ultrasound to locate bladder activity. In some embodiments, the channels 350 on the back of the struts 330 are filled with air, readily visualized by ultrasound.

In some embodiments, at least one magnetic field is created near the patient and creates electromagnetic signals and/or currents in coil components of the device 100, to allow localization of such components and localization of bladder contractions. Such systems may use the technology known in the art of cardiac 3D mapping. In some embodiments, the magnetic field is a changing magnetic field.

In some embodiments, the coil components of the device 100 are deployed by an expandable member, which may be separate from expandable member 110. In some embodiments, the coil components or other components used for localization are coupled to stripes (struts) 330.

In some embodiments, the coil elements used for localization can be preferentially disconnected from electrical circuitry, conductivity or conductance, to minimize the current created within the coil in response to the magnetic fields around the patient. Since each coil emits an electromagnetic field once current flows through it, this feature of the device 100 is used in order to minimize interference between the various coils and to allow recording from a coil or group of coils, while adjacent coils are disabled, to avoid interference.

The present disclosure further describes additional devices and methods for transurethral bladder partitioning therapy. The following devices and methods described were developed in the course of intensive experimentation with the prototype NewUro Uzap device, which includes many of the device features described above, in ex-vivo and in-vivo animal models.

Balloon with Sliding Wire Electrodes.

Aspects of the present disclosure also provide devices for treating a disorder in a hollow bodily organ. Such a device may comprise a shaft, an expandable member, and at least one longitudinal wire which may comprise a wire electrode. Since, as will be described below, as a result of expansion and contraction of said expandable member, said wire electrode may slide out of said shaft during expansion of expandable member, and slide back into said shaft during contraction of expandable member, resulting with a relative sliding motion between said wire electrode and said expandable member, said wire electrode will herein be termed "sliding wire electrode." The shaft may be advancable through a bodily channel of a patient to reach a cavity of the organ. The expandable member may be coupled to a distal end of the shaft. The expandable member may have a collapsed configuration advancable through the bodily passage to reach the cavity of the organ and an expanded configuration configured to contact an inner wall of the organ when the expandable member is advanced therein. The longitudinal wire(s) may be disposed over an outer surface of the expandable member and fixedly coupled to a distal end of the expandable member (i.e., a distal pole of the expandable member). The longitudinal wire(s) may be configured to slide across the outer surface of the expandable member as the expandable member transitions between the collapsed and expanded configurations. The longitudinal wire(s) may be parallel to the longitudinal axis of the device and/or device shaft. The hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

In some embodiments, the device further comprises at least one latitudinal wire disposed over the outer surface of the expandable member and transverse to the at least one longitudinal wire. One or more of the latitudinal or longitudinal wire(s) may comprise an ablation electrode configured to create a tissue region having reduced electrical propagation in the inner wall of the organ to modify one or more of a mechanical or electrical property of the organ. The longitudinal wire(s) may be configured to slide across the latitudinal wire(s) as the expandable member transitions between the collapsed and expanded configurations. The latitudinal wire(s) may be parallel to an equator of the expandable member. The latitudinal wire(s) may run at the circumference of the balloon at latitude that is approximately halfway between the equator and the pole(s) of the expandable member. One or more of the longitudinal or latitudinal wire(s) may comprise a bundle of wires, each having a surface conductive at different parts. The treatment device may further comprise at least one loop through which the longitudinal wire(s) crosses through as it slides.

The expandable member is typically disposed over the distal end of the shaft. In some embodiments, the distal end of the shaft is telescopic to extend in length as the expandable member transitions from the collapsed to the expanded configuration. The telescopic distal end of the shaft may vary in length from 2 cm to 5 cm when collapsed to 4 cm to 15 cm when fully extended.

Aspects of the present disclosure also provide methods of treating a disorder in a hollow bodily organ. Such a method may comprise the following steps. A tissue modification device may be advanced through a bodily passage to reach the cavity of the organ. An expandable member disposed at the distal end of the tissue modification device may be expanded within the cavity such that an outer surface of the expanded expandable member contacts an inner wall of the organ. A predetermined pattern of tissue regions having reduced electrical propagation may be created in the inner wall of the hollow bodily organ to modify at least one of a mechanical or an electrical property of the organ. The tissue modification device may comprise at least one longitudinal wire disposed over an outer surface of the expandable member and fixedly coupled to a distal top of the tissue modification device (i.e., a distal pole of the expandable member). The longitudinal wire(s) slides over the outer surface of the expandable member as the expandable member is expanded or collapsed. The hollow bodily organ may be selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

In some embodiments, the expandable member is expanded by inflating the expandable member. In some embodiments, the expandable member is expanded by lengthening a telescopic shaft coupled to and disposed within the expandable member.

In some embodiments, the tissue modification device further comprises at least one latitudinal wire disposed over the outer surface of the expandable member and transverse to the at least one longitudinal wire. The predetermined pattern of tissue regions having reduced electrical pattern may be based on an arrangement of the at least one longitudinal or latitudinal wires.

In some embodiments, the predetermined pattern of tissue regions is created as the expandable member is expanded. In some embodiments, the predetermined pattern of tissue regions having reduced electrical propagation is created by creating an ablation pattern on the inner wall of the organ.

Figure 42C:
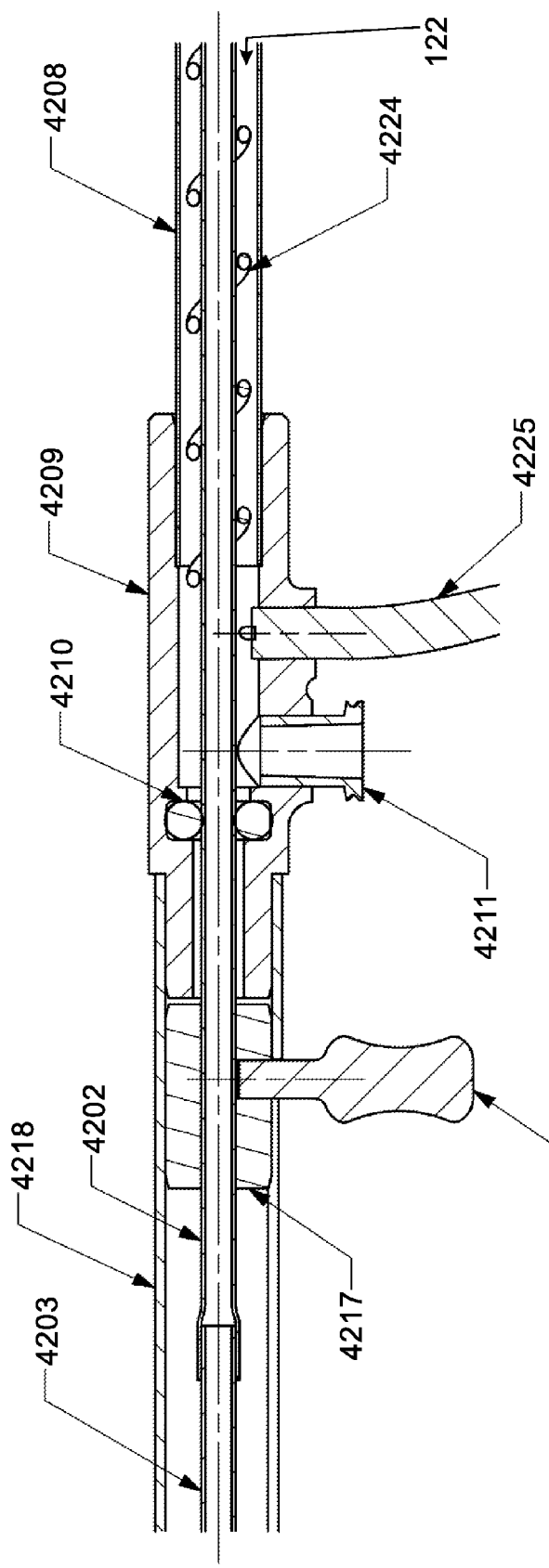
Figure 42D:
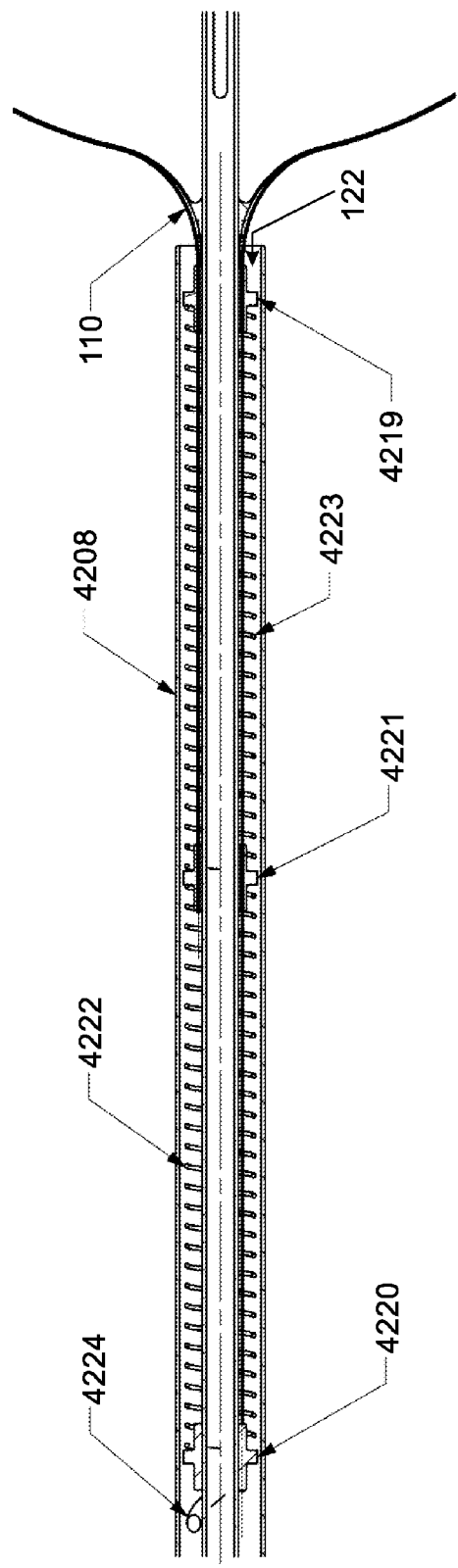
Figure 42E:
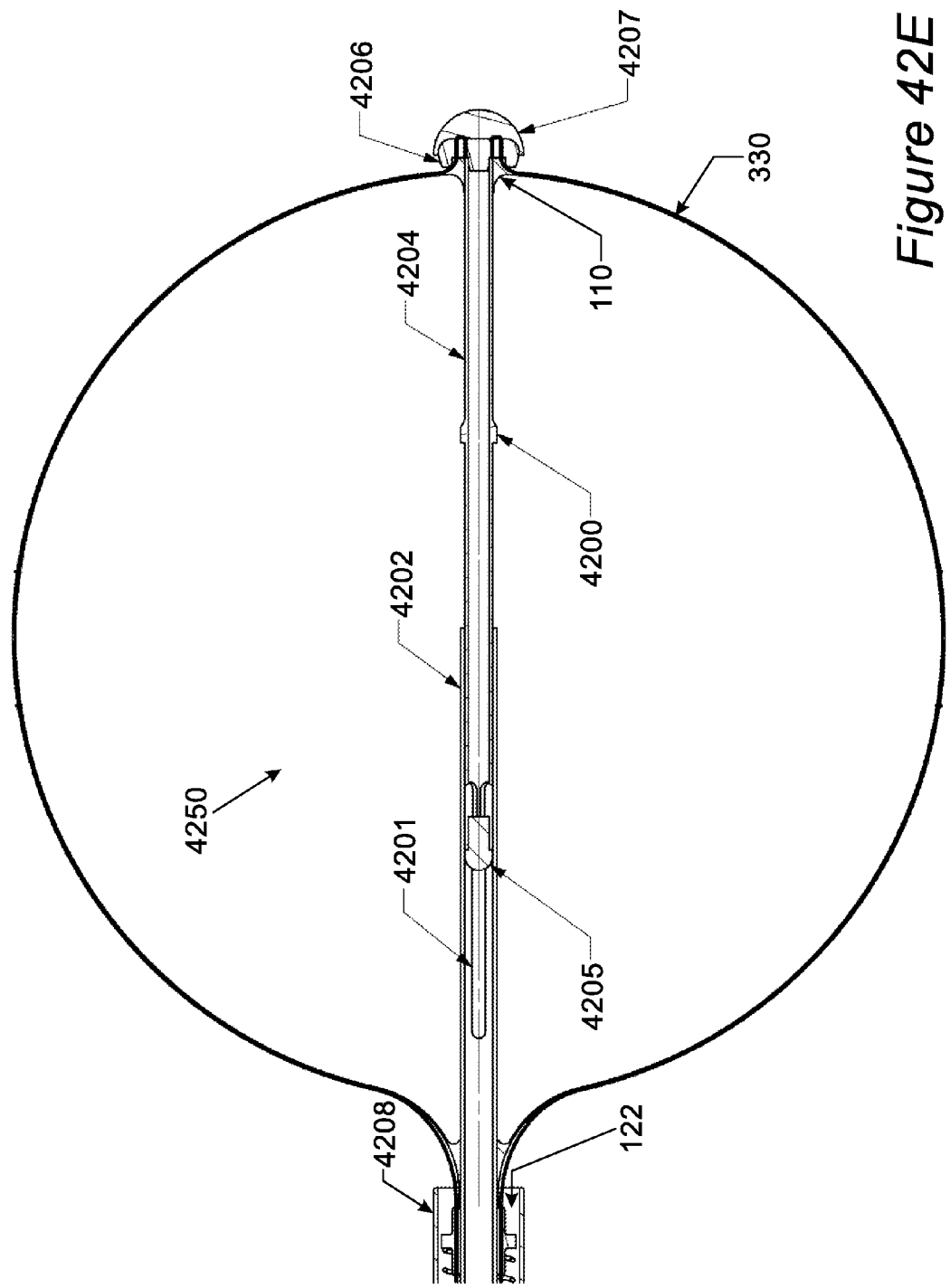
Figure 42F:
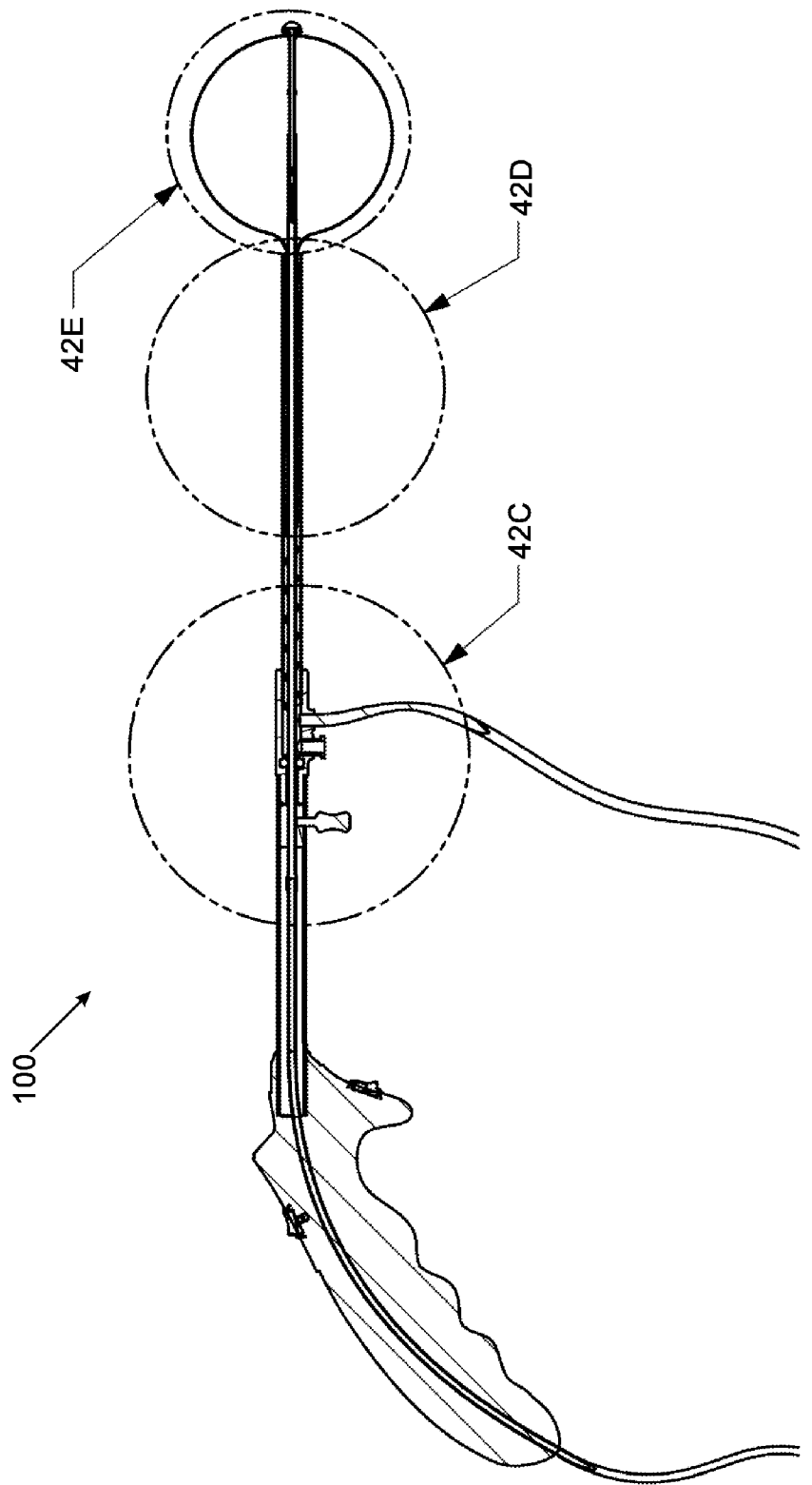
Figure 42G:
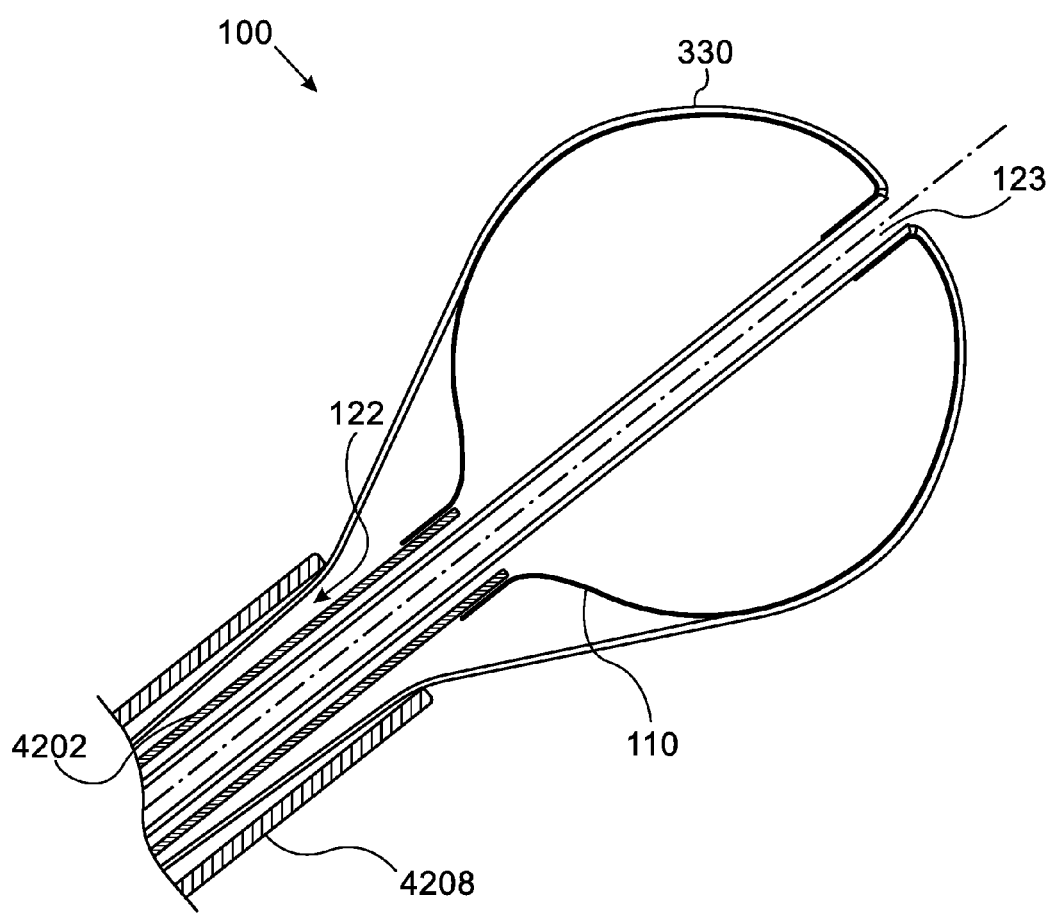
FIG. 42G shows a schematic of a longitudinal section of a sliding wire based ablation device in which a coaxial balloon structure is used to provide a distal urine lumen through the balloon structure, according to many embodiments

As shown by FIGS. 42 to 42G, the device 100 may be based on a balloon 110 which deploys sliding wire electrodes. In some embodiments, the apparatus 100 is balloon based. Advantages of using a balloon 110 to bring the electrodes 132 in contact with the bladder wall BLW may include (i) the ability to create high radial force, (ii) the ability to conform to different bladder diameters and shapes, (iii) a homogenous distribution of forces around the bladder wall, preventing areas of stress concentration, and (iv) the ability to be crimped into a very low outer diameter (OD). The ability to create high radial force may be important both for good electrode contact with the wall and for withstanding significant transient intra-abdominal pressure increases as might occur during cough, laughter, postural changes, etc.

An advantage of using sliding wire electrodes may be to enable creating complex patterns of ablation lines, while at the same time maintaining a low outer diameter of the device 100. Since in the currently described embodiments, the wires can function as both the struts 330 and electrodes 132, it should be made clear that the wire electrodes will be referred to as 330, and their exposed areas serve the same purpose as electrodes 132.

Such a (disposable) apparatus 100 may include an external tube 4208 typically having an OD of 16 French to 26 French, a port 4209 allowing fluid to flow through the tube, a handle 4215 to hold the device, and a lever 4216 that allows moving the catheter in and out of the tube. In some embodiments, the catheter includes an inflation tube 4202 or 4203 that allows flow of fluid as shown in FIG. 42C, a balloon 110 as shown by FIG. 42 inflated by this fluid (typically to a volume of 150 cc to 400 cc), a cap 4207 as shown by FIG. 42 configured to safely contact the bladder wall BLW and wires that are at least in part conductive and acting as electrodes.

In some embodiments, the expandable member shaft 4250 that is surrounded by the balloon 110 is a telescopic shaft 4250 as shown by FIG. 42E, allowing elongation and shortening of this part of the shaft 4250. In some embodiments, the elongation and shortening are limited by stopper components 4205 which protrude into a cut "window" in the tube, limiting the minimal and maximal length of this part to between 2 cm and 10 cm.

A purpose of such a telescopic shaft 4250 may be to allow the balloon 110 to significantly expand in length and volume without being limited by the length of the shaft. This less limited expansion can prevent inversion of the balloon ends which occurs when a balloon 110 without a telescopic shaft is inflated to a length greater than that of the shaft. Another advantage may be that a telescopic balloon 110 can be easily inserted into a small bladder, and inflated to a large size, whereas a non-telescopic balloon would be distorted when inserted into a bladder shorter than the shaft length. The stopper components 4205 may serve multiple purposes: upon expansion of the balloon 110, and in case of balloon rupture, the upper limit of length limits the distal part of the telescopic shaft from accidentally exiting the proximal part, and thus loosing continuity. In addition, the minimal length limitation can maintain tension of the balloon 110 and wires 330 while being pushed through the shaft and into the bladder BL. When retracting the device 100, the minimal length limit of the telescopic part 4250 is useful to limit balloon 110 and wire folding that might interfere with retraction into the shaft (folds and entanglements will increase the volume and diameter of the catheter), and the maximal length limit ensures the distal part is pulled out together with the proximal part. In addition, the stopper components 4205 transfer torque between the telescoping tubes, allowing control of balloon orientation by the handle 4215.

In some embodiments, the force needed to retract and extend the telescopic shaft 4250 is preset to be within a predetermined range, to allow the shaft 4250 to support pulling of the wires, to maintain tension of the wires to support orderly retraction into the shaft 4250.

In some embodiments, the telescopic shaft 4250 can be "locked" or released by the operator.

In some embodiments, the telescopic shaft 4250 retraction and extension are dependent on the pressure in the balloon 110. When the pressure is high enough, the force required for relative movement of the telescopic parts can increase, and when the pressure decreases, the force required for relative movement can decrease. This difference can be achieved, for example, by at least part of the telescopic shaft 4250 being flexible, expanding to contact and press against the other part of the shaft 4250, when pressure is applied to the balloon 110.

A device 100 having the telescopic balloon shaft 4250 may be useful to orchestrate the retraction of the catheter, maintaining tension on the wires 330 while avoiding premature shortening of the telescopic shaft 4250 (that might lead to kinks and folds in the balloon). This property may also be useful when inflating the balloon 110, to cause the balloon 110 to first increase in width, and only later in length, to avoid the wires 330 being pulled into the bladder BL without ensuring good contact against the lateral bladder wall BLW.

In some embodiments, the wires 330 as shown in FIG. 42 are connected distally to a cap component 4207 and then run parallel to the main shaft 4250, enter the device shaft 4208, and connect to a power generator.

In some embodiments, the length of the wires 330 is set with enough slack to allow both the elongation of the expandable member shaft 4250 as described above, and inflation of the balloon 110. The extra slack may be located outside the device shaft 4208 and is pulled into the bladder BL by the deployment of the expandable member 110. In some embodiments, the wires 330 are marked (by numbers, or change of pattern or color), so that the operator can readily visualize the advancement of the wire slack and visually see if the wires 330 were pulled into the bladder BL enough to signify device deployment, and balloon 110 inflation to the desired volume. In some embodiments, the wires 330 are connected to a lever or indicator that can slide along the device shaft 4208 or handle 4215 signifying the position of the wires 330, indicating when the device 100 has been deployed, and when the balloon 110 has been inflated.

Alternatively or in combination, the wire slack may be tightened by springs located along the sheath shaft 4208. These springs can ensure the wires 330 will remain taut before balloon inflation and when the balloon 110 is deflated just before retraction. FIG. 42D shows wires 330 entering sheath 4208, attaching and passing through spring loaded rings 4220 or 4221, and continuing to the handle and generator as cable 4224.

In some embodiments, in addition to the wires 330 running parallel to the catheter shaft 4208, other "transverse" or "circumferential" wires 4212 are provided as shown in FIG. 42. In some embodiments, the cumulative length of the transverse wires 4212 is set to be approximately the circumference of the balloon 110 between adjacent longitudinal wires 330 (i.e., where there are 8 longitudinal wires 330, the length of each of the transverse wires 4212 will be approximately one eighth of the circumference of the balloon 110). In some embodiments, the length of these wires 330 is set to be the circumference of the balloon 110 at a higher latitude than the equator of the balloon 110. For example, the length of the transverse wires 4212 can be set to have the circumference of the balloon 110 at a point that is mid-way between the equator of the balloon 110 and the pole of the balloon 110.

In some embodiments, the wires 330 parallel to the device shaft 4208 have a conductive surface distal to the meeting point 42A with the transverse wires as shown in FIG. 42A, and are fully insulated proximal to the point of this connection. In some embodiments, each of the wires 330 described is comprised of several wires, bundled together (e.g., four wires braided together into one cable). In some embodiments, the conductive surface (and the resulting ablation line) is composed of the conductive surface of one wire 330, followed by the conductive surface of the next wire 330 in the bundle, etc. In some embodiments, there is a small gap (0.1 cm to 1 cm) between the different conductive surfaces. In some embodiments, the wires 330 are bundled as a flat stripe, all the conductive surfaces facing the same direction. In some embodiments, the distance between adjacent wires 330 in the bundle is kept fixed (by the material embedding the wires). In some embodiments, two or more wires 330 are exposed (have their surface conductive) in parallel and the ablation is performed between two such parallel wires (bi-polar).

The circumferential wires may be connected at one point 4214 to at least one longitudinal wire 330 and/or the balloon 110. In some embodiments, these wires 330 are additionally connected to another point in an adjacent longitudinal wire 330. In some embodiments, the distal connection is fixed, while the proximal connection allows "sliding" of the wire 330, so that at least part of the transverse wire 330 is pulled into the shaft 4208 of the device 100 by the deployment and/or expansion of the expandable member 110. In this way, when the balloon 110*s* is deflated, all wires 330 may be parallel to the catheter's longitudinal axis, and when the balloon 110 is inflated, wires 110 create longitudinal and circumferential lines over the balloon surface. In some embodiments, the transverse wires 4212 are pre-folded in a "V" shape before insertion of the catheter into the shaft 4208, so that they are parallel to the long axis of the device. In some embodiments, these wires 4212 are folded so that the point of the "V" is placed proximal to the place the wire 4212 connects to the longitudinal wires 330 (to avoid folding and distortion of the wire 4212 when the catheter is pushed outside the shaft).

In some embodiments, a seal or valve 4210 as shown by FIG. 42C is placed in the device shaft 4208, allowing sealing the shaft 4208 to passage of fluids, while enabling advancement of the catheter through the shaft 4208. In some embodiments, the valve 4210 can be opened and closed at will. In some embodiments, the valve 4210 is placed over the catheter during production, even before the catheter (and valve 4210) are inserted into the device shaft 4208.

In some embodiments, the catheter element has a disconnection point for easy disconnection of the catheter from the rest of the device 100. In some embodiments, this disconnecting point is used to disconnect the catheter, to retrieve the shaft 4208 of the device 100 (and all other component except the catheter, such as the handle, lever, etc.), while leaving the catheter in place. This disconnect ability may be useful in the unlikely and undesirable event that the device 100 is stuck to the bladder BL or the device 100 did not retract to the desired diameter to allow retraction through the device shaft 4208, or it was clinically beneficial to leave the catheter in place after the ablation (for drainage, bleeding control, or repeated ablation at a later time). In some embodiments, a guidewire extends distally from the disconnection point, to facilitate "over the wire" delivery of a shaft around the catheter, to aid in catheter retrieval.

In some embodiments, the distal part of the catheter (i.e., the cap 4207) is slightly domed and smooth to facilitate passage through the urethra URH and offer safe contact with the bladder BL. In some embodiments, this cap 4207 is slightly larger than the distal opening in the shaft 4208, so that the catheter (and its cap) can be pushed out of the shaft, but not pushed in beyond the cap. In some embodiments, the cap is fenestrated, to allow passage of fluid through the shaft 4208, even when it is covered by the cap.

In some embodiments, thermocouples are applied to evaluate the ablation process by measuring the temperature around them. Since the ablation area may be large and extensive deployment of thermocouples to each and every square millimeter will be expensive and bulky, it may be beneficial to place the thermocouples at key points on the device 100. In some embodiments, thermocouples are located around the equator line of the balloon 110, this being the zone where the balloon is thinnest and most prone to rupture by heat. In some embodiments, the thermocouples are placed at several points on the device, the hottest place (i.e., at the beginning or end of an electrode, at 6 o'clock of the patient), the coldest place (an electrode at mid balloon height, at 12 o'clock of the patient) and average places. Thus, a good picture of the temperature ranges may be achieved with a minimal number of thermocouples.

Referring to FIGS. 42 to 42G, a disposable apparatus 100 may be inserted into the bladder BL with an outer diameter of less than 8.6 mm, and may be capable of apposing wire electrodes to the wall of a bladder at a diameter of 70 mm. The device 100 may be based on an inflatable balloon 110 with sliding wire electrodes.

More particularly, FIG. 42 is a side view of the device 110, in its deployed (inflated) state. The device 100 may be comprised of the following main parts from proximal to distal: handle 4215, slider housing 4218, sheath 4208, and balloon 110. Details of each of the last three components are shown in FIGS. 42C to 42E, as described in FIG. 42F.

The handle 4215 may further include flexible fluid tube 4203, which exits from its proximal part, as well as activation button 4228, and safety button 4227 located at its distal end. The distal end of handle 4215 may be connected to the proximal end of slider housing 4218.

The flexible inflation tube 4203 may be passed through handle 4215 and slider housing 4218, where it may become continuous with balloon inflation tube 4202 as shown in FIG. 42C.

FIG. 42C is a longitudinal section view of slider housing 4218 and adjacent parts. From proximal to distal, it shows slider housing 4218 which may be connected to sheath valve 4209, which in turn may be connected to sheath 4208, having urine lumen 122.

Flexible inflation tube 4203 may be passed through slider housing 4218, and may be continuous with balloon inflation tube 4202, which in turn may pass through slider 4217 and attach to it, and then may pass inside valve 4209 through valve seal 4210, and may continue through sheath 4208.

Slider housing 4218 may comprise a cylindrical tube with a longitudinal slot, through which protrudes deployment handle 4216, which may be connected to slider 4217, which may be slideably moveable inside slider housing 18 along its longitudinal axis.

Valve 4209 can have a proximal end, which may connect to the distal end of slider housing 4218, and a distal end which may connect to the proximal end of sheath 4208. Valve 4209 may further comprises a valve seal 4210, through which may pass balloon inflation tube 4202. Seal valve 4210 may maintain a fluid seal around balloon inflation tube 4202 while also allowing it to slide forward and backward. Thus, valve seal 4210 may divide the device 100 into two separate compartments, a proximal compartment, and a distal compartment, which following insertion into the bladder BL, may become continuous with the bladder lumen surrounding balloon 110.

Additional components of valve 4209 may be sheath drain luer 4211, which may be continuous with urine lumen 122 of sheath 4808, and may allow drainage or inflation of the device distal compartment and bladder lumen, and connecting cable 4225, which may be the proximal end of cable 4224. Cable 4225 may have connector 4226 at its proximal end.

Sheath 4208 may comprise a cylindrical tube, through which pass balloon inflation tube 4202. Its proximal end may be connected to valve 4209, and its distal end may be free. FIG. 42D is an exploded longitudinal section view of sheath 4208 with the balloon deployed, showing sheath 4208 having urine lumen 122, balloon inflation tube 4202, fairlead 4219, longitudinal wire tightening spring 4223, longitudinal wire tightening ring 4221, circumferential wire tightening spring 4222, circumferential wire tightening ring 4220, and wound 4216 conductors cable 4224.

More particularly, each of fairlead 4219 and rings 4221 and 4220 may be shaped as a short tube with a wider ring radially protruding from the tube's mid part, with 8 holes around the ring's circumference. Fairlead 4219 may be securely connected to a balloon inflation tube 4202 adjacent the balloon 110, while rings 4221 and 4220 may be slidable along the balloon inflation tube 4202. Electrode wires leaving the balloon 110 at its base, may enter sheath 4208 at its distal end, pass through the holes of fairlead 4219 (2 wires through each hole), and continue parallel to balloon inflation tube 4202, passing through holes of rings 4221 and 4220. Longitudinal electrode wires may attach to ring 4221, while circumferential electrode wires may attach to ring 4220. Longitudinal wire tightening spring 4223 may push ring 4221 proximally along balloon inflation tube 4202, while circumferential wire tightening spring 4222 may push ring 4220 proximally along balloon inflation tube 4202. Thus, wires may be kept untangled and taut. Proximal to ring 4220, the wires coalesce into wound conductors cable 4224, which may be wound around balloon inflation tube 4202 and may continue proximally to exit valve 4209 as connecting cable 4225.

FIG. 42E is an exploded longitudinal section view of the central balloon area showing from distal to proximal: balloon cap 4207, balloon cap base 4206, balloon 110, wire electrodes 330, telescopic balloon tube 4204, distal end of balloon inflation tube 4202, and wedge stoppers 4205.

More particularly, balloon cap 4207 may comprise a dome shaped part covering balloon cap base 4206, which is discoid shaped, and has two lines of holes around it. The wire electrodes may pass through these holes, making a "U turn" such that when balloon cap 4207 is placed of balloon cap base 4206, the wires may be anchored to the cap while remaining electrically separated from each other. The wires may continue over the outer surface of balloon 110 to reach its base on the proximal end of the balloon 110. The telescopic balloon tube 4204 may have several holes for balloon inflation. The proximal end of telescopic balloon tube 4204 may be slideably situated inside distal end of balloon inflation tube 4202, and may have an "end of travel stop" 4200 that stops it from entering all the way into balloon inflation tube 4202. Stoppers wedge 4205 may comprise an elongated element connected to proximal end of telescopic balloon 4204, with three radial protrusions. Balloon inflation tube 4202 may have at its end three longitudinal cutout slots 4201, into which protrude the three protrusions of stoppers wedge 4205.

Thus, telescopic balloon tube 4204 may be free to move in and out of balloon inflation tube 4202, within limits defined by "end of travel stop" 4200 and stoppers wedge 4205 together with the longitudinal cutout slots 4201.

Cap 4207 preferably has an outer diameter equal to the outer diameter of sheath 4208, so that it completely covers its edges during insertion, preventing damage to the urethra, as well as excessive retraction of the balloon.

Returning now to FIG. 42, the device 100 may have 8 longitudinal wire electrodes 330, and 8 circumferential wire electrodes 4212, but may have between 1 and 24 longitudinal and circumferential electrodes. All wire electrodes may be connected to cap 4207 and run along exterior surface of balloon 110 to its base and into sheath 4208. In expanded detail views of FIGS. 42A and 42B, insulated wire electrode areas are hatched, while exposed wire electrode areas are blank.

As shown in expanded detail FIG. 42A, each longitudinal electrode 330 is connected to a circumferential electrode 4212 at a point 42A proximal to the circumferential line created by the circumferential electrodes 4212. The connection is made by electrode loops 4214, which may for example be a miniature metal ring, or alternatively may be a polymeric loop or short tube. Loops 4214 may be attached to balloon 110, and or to one or more of the wire electrodes 330 or 4212. Typically, at point 42A, loops 4214 will connect both electrodes without allowing relative movement between them.

As shown in expanded detail FIG. 42B, each longitudinal wire electrode 330 is further connected to a circumferential electrode 4212 at a point 42B proximal to the circumferential line created by the circumferential electrodes 4212. The connection may be made by electrode loops 4214*a*, which may for example be a miniature metal ring, or alternatively may be a polymeric loop or short tube. Loops 4214A may be attached to balloon 110, and or to one or more of the electrodes 330 or 4212. Typically, at point 42B, loops 4214A will connect both electrodes 330 or 4212 while maintaining relative movement between them. For example, this connection can be achieved by loops 4214A being glued or soldered to one of wire electrodes 330 or 4212, while the other wire electrode passes freely through the loop 4214A. Alternatively or in combination, the loops 4214A may be connected to the balloon 110 while both wire electrodes 330 and 4212 pass freely through the loops 4214A.

In transitioning between inflated and deflated balloon states, as balloon 110 deflates, circumferential wire electrodes 4212 will typically retract more than longitudinal wire electrodes 330, and therefore at point 42B there may be significant relative movement between these wires 330, 4212, which may be enabled by wire loops 4214A. At point 42A, both wire electrodes 4212 and 330 will move relative to balloon 110, but not relative to each other. At a fully deflated state, all wire electrodes 330 may be completely parallel to the longitudinal axis of balloon 110. During inflation, the same events take place in a reverse sequence and opposite direction.

Of note, thermocouples may be included in the device 100 in a similar manner to longitudinal wire electrodes 330 or circumferential wire electrodes 4212.

A possible preferred material for the balloon is silicone, due to its high elongation, strength, temperature resistance, and biocompatibility. The wall thickness in the deflated state may preferably be 0.1-0.3 mm, typically 0.05-0.5 mm.

Alternatively, a noncompliant material such as Polyethylene terephthalate (PET) could be used for the balloon 110.

The advantages of a non-compliant balloon 110 may be that higher inflation pressures can be used with a resulting rigid structure, and better wall apposition of the electrodes 132.

Various modifications may also be possible. For example, as schematically depicted in FIG. 42G, a balloon 110 with a coaxial structure may be used, i.e., wherein an inner tube goes through the balloon 110, providing a distal urine lumen 123 for bladder drainage or filling, or for passage of a guidewire, and balloon inflation is achieved via an external tube surrounding the inner tube.

In some embodiments, the electrodes are printed on the balloon 110 or on the struts 330, much like in flexible printed circuitry. In these embodiments, conductive ink like material is used to "draw" conductive lines along the balloon 110, either directly on its surface or on thin polymeric struts replacing the wires 330 previously described. Such conductive printed elements can be partially coated with an isolating material, so that only the exposed areas (non-coated areas) act as effective electrodes.

In typical use, the patient is connected to a dispersive electrode, and the device 100 and dispersive electrode are connected to an RF generator. Before insertion into the urethra URH, deflated balloon 110 may be situated within sheath 4208. Balloon 110 may be flushed with fluid and emptied to remove air, and the device 100 may be lubricated externally with an appropriate lubricant. The device 100 may be inserted through the urethra URH and into the bladder BL to a predetermined distance, typically marked externally on sheath 4208. The user may inflate the bladder via port 4211 to expand the bladder BL before device deployment. The user may then move deployment handle 4216 distally. Slider 4217 may move distally within slider housing 4218, moving with it balloon inflation tube 4202 together with balloon 110, telescopic balloon tube 4204, and wire electrodes 330 and 4212, such that balloon 110 becomes deployed within the patient's bladder. Typically, the user may then inflate balloon 110 via flexible inflation tube 4203, to a predetermined volume, of approximately 180 cc. As balloon 110 inflates, it may pull wire electrodes 330 and 4212 into the bladder BL and radially towards the bladder wall BLW. Due to wire loops 4214 and 4214a, circumferential electrodes 4212 may assume a circumferential position and collectively create a circumferential line. The bladder BL may then be collapsed over balloon 110 with its wire electrodes 330 and 4212, by draining its lumen through port 4211.

Impedance can be measured at all electrodes, and RF energy can be delivered to create the specified lesions. Delivery of the energy from the RF generator may typically be initiated by simultaneously pressing activation button 4228 and safety button 4227. Often, pressing just one of these will not result in generator activation. Monitoring of at least impedance and temperature may be performed during ablation. Typical settings of RF energy delivery for ablation may, for example, be 5-50 Watts at a frequency of around 500 kHz, for a duration of 1-20 seconds.

Following ablation, the bladder may be filled again around the device through port 4211, to ensure separation of the electrodes from the tissue. Balloon 110 may be drained via flexible inflation tube 4203. As balloon 110 empties, electrode wires 4212 and 330 may be automatically pulled back by wire tightening rings 4220 and 4221 and springs 4222 and 4223, such that they end up taut and parallel to balloon 110 longitudinal axis. Once balloon 110 is empty and all electrodes have been pulled out, the user may pull deployment handle 4216 proximally, thus retracting balloon 110 with its electrodes into sheath 4208, which is then removed from the patient's urethra URH.

Device Contact.

It has been found by the inventors that long (3 cm and over) and homogenous ablation lines can be achieved in bladder tissue by a single monopolar electrode, when the contact force of the electrode and the bladder is sufficient and homogenous.

In some embodiments, ablations are performed while the device 100 is actively pressing against the bladder wall BLW, by active expansion of the expandable member 110 just prior to and/or during ablation. In some embodiments, ablations are followed by a period of detachment from the bladder wall BLW, by active deflation of the expandable member 110. In some embodiments, each ablation may be performed while the device 100 is expanding, followed by a retraction period between ablations. In some embodiments, this maneuver may be performed only when the measured impedance of the electrode is outside of a given range, for example not between 50 ohm and 300 ohm (depending on the electrode type used).

In some embodiments, the expandable member 110 of the device 100 (i.e., balloon or expandable cage) and/or an external unit controlling volume and flow, are configured to generate periodic changes in volume, accounting for between 5% to 50% change in the volume of the expandable member, in the course of 10 to 50 seconds. In some embodiments, these volume changes are periodic, with a sinus like wave form.

In some embodiments, the ablation is applied at times when the volume of the expandable member 110 is increasing.

In other embodiments, the volume of the bladder BL itself is manipulated to achieve the same effect of periodic change in the relative volumes of the bladder BL and the device 100. In some embodiments, the bladder BL is filled with additional volume after an ablation and is drained just before and/or during an ablation. In some embodiments, the expandable member 110 is expanded to surround a certain volume, and then the bladder BL is emptied to a volume that is less than that by 5% to 50%. This technique can also be used to cause the bladder BL to come in good contact with an expandable member which is not a balloon BL (e.g., a cage, or malecot-like structure such as those described herein), while controlling the force and pressure the bladder BL can apply against the device 100.

In some embodiments, the bladder BL is distended after an ablation to enlarge the scar the ablation will cause.

In some embodiments, the balloon 110 of the device 100 is inflated with fluid. This fluid inflation can allow for easy control of inflated volume, use of gravity for inflation, cooling of the balloon and electrodes, and importantly—improved electrode contact with tissue due to the fluid being non-compressible.

In some embodiments, the balloon 110 of the device 100 is inflated with air (or other gas), to minimize the weight of the balloon, to minimize variations in the contact pressure of the balloon and the bladder (in a fluid filled balloon, with the patient supine, the dorsal part of the balloon will press against the bladder wall stronger than the ventral part, due to balloon weight).

In some embodiments, air pressure is used to manipulate the volume of the bladder. Air pressure can be applied to allow faster changes in volume.

In some embodiments, the bladder BL is filled to a volume that exceeds the volume of the expandable member—and is maintained at such a level when the device is being retracted—to avoid "pinching" of bladder tissue between the collapsing elements of the expandable member.

Cage Configuration.

Figures 43A, 43B:
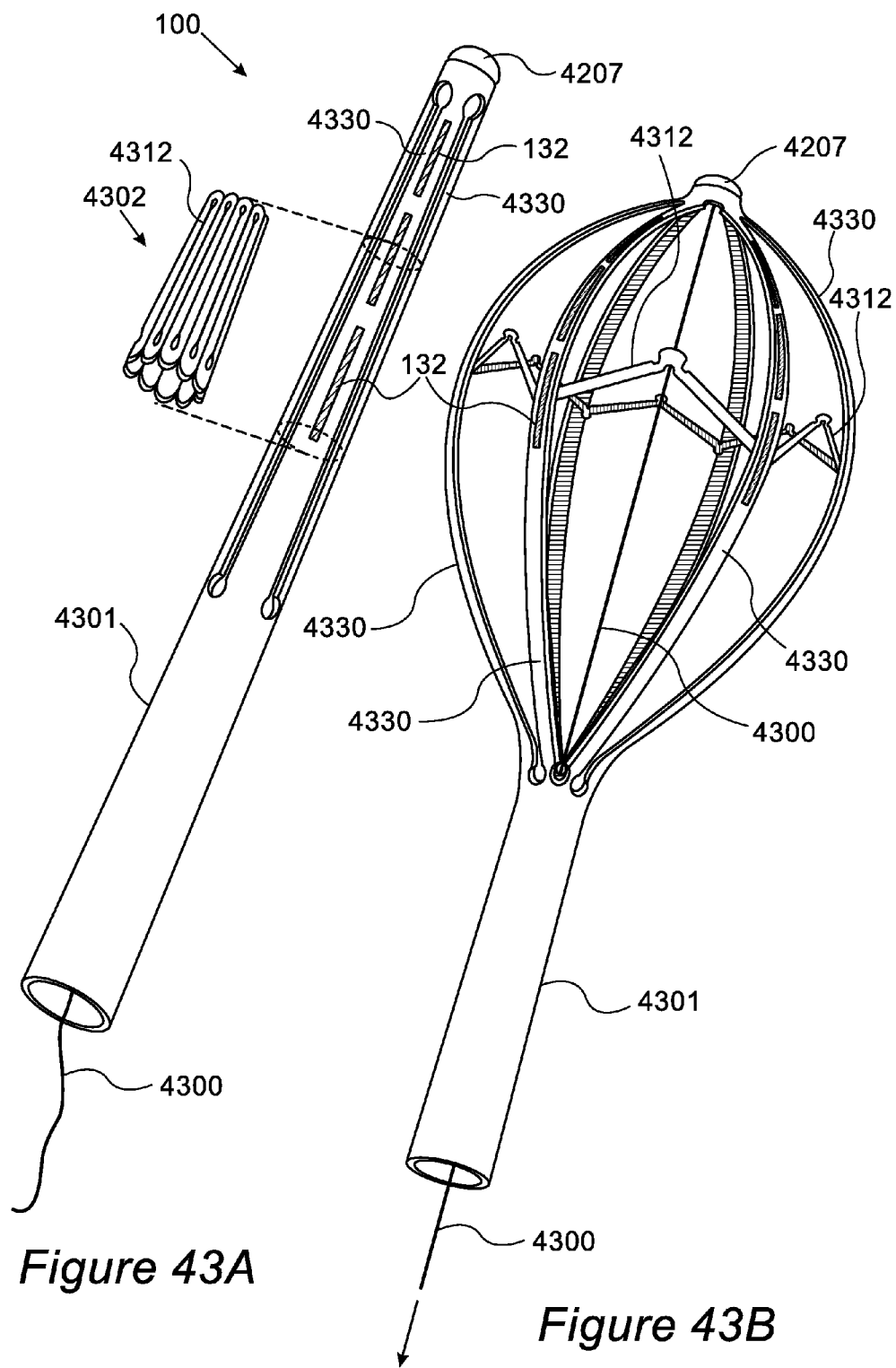
FIG. 43A and FIG. 43B show an ablation device with a malecot-like expandable member, according to many embodiments.

As shown by FIGS. 43A and 43B, in some embodiments, the catheter component is made of a flexible tube 4301 cut in such a way that when compressed along its longitudinal axis, it will collapse and assume a cage like structure, with struts 4330 arching from the proximal part of the tube 4301 to a distal part of the tube 4301. In some embodiments, to achieve the desired shape, the tube 4301 is cut with parallel longitudinal lines. In some embodiments, parts of the tube are removed in the process, leaving gaps in the tube shaft. In some embodiments, these gaps are wider at certain parts and narrower at other parts. In some embodiments, the width of the gaps (and thus the width of the remaining tube material) is used to determine the curvature of the tube stripes when the tube is pressed along its long axis. In some embodiments, wider gaps (narrower tube material stripes) are used in areas where a sharper curve is desired and made narrower (wider tube material stripes) in places where less curvature is desired. In some embodiments, the struts 4330 are designed to create a shape that is "tear-like," with the narrow part of the shape facing the bladder neck, and the wide part facing the bladder dome. In some embodiments, the gaps are wider at the distal part of the catheter, allowing the distal part of the tube 4301 to open into a wide dome, and narrower at the proximal parts of the tube, allowing less curvature and creating the desired "tear-like" shape.

In some embodiments, parts of the tube 4301 are removed proximally and distally to form "bridge sections" of the tube 4301 that are connected to the rest of the tube only in transverse, but not along the long axis. In some embodiments, these bridge sections 4312 are partially cut, to allow the section to be opened into a line (straight or "zig-zag") when compressive force is applied to the tube's longitudinal axis. In some embodiments, this line may extend between adjacent tube stripes that bulge from the tube as described above. In some embodiments, these "bridge sections" 4312 may be made narrow at the meeting point with adjacent tube stripes to allow flexion at these points, allowing the "bridge sections" 4312 to become substantially circumferential to the long axis of the tube. In some embodiments, bridging between adjacent tube stripes may be achieved by wires.

In some embodiments, bridge sections may be formed by a second tube 4302 attached to the first tube 4301, preferably placed inside tube 4301 as shown in FIG. 43A. In these embodiments, the tube 4302 may typically be made of a softer material that is more readily deformed and distorted. In some embodiments, pressure may be applied to both tubes along their longitudinal axis with the firmer tube 4301 creating the cage as described above, and the softer tube creating limbs that diverge from being parallel to the long axis of the tubes, thus "bridging" between adjacent limbs of the firmer tube as shown in FIG. 43B. In some embodiments, the outer firmer tube 4301 may become shortened by the applied force to a lesser extent than the shortening of the inner, more flexible tube 4302 (to allow longer tube stripes, becoming more deformed and more distorted, moving away from being parallel to the long axis. In some embodiments, both tubes are displaced to a similar extent along their long axis, but the strip elements of the inner tube 4302 may be shorter, and thus may become more deformed than the stripes of the outer tube. In some embodiments, at least one of the tubes may be rotated at its proximal end while the distal end may be kept fixed, to twist the tube stripes of one tube to intersect with the stripes of the second tube.

In some embodiments, a conductive material may be used to coat parts of the tube that are intended to work as electrodes. In some embodiments, this coating is non-continuous, to create distinct electrode sections. In some embodiments, the tube stripes are coated by conductive material at their distal parts, but not their proximal parts, to create an upper hemisphere of exposed electrodes (rather than a complete sphere of exposed electrodes).

In some embodiments, a wire 4300 extends from the cap 4207 inside the distal part of the tube 4301 to the proximal part of the tube 4301. When this wire 4300 is pulled proximally, while the proximal part of the tube 4301 is firmly held in place—the desired force along the longitudinal axis of the tube 4301 can be achieved as shown by FIG. 43.

In some embodiments, the tube 4301 may be made of an elastic material that may return to the tube shape once the pressure is released. In some embodiments, the tube 4301 may be made of metal. In some embodiments, the force required to create the shape changes described above may be beyond the reasonable force for manually operating a surgical tool. In some embodiments, a dedicated leverage device (wheel or lever) is connected to the tube shaft, to allow easy and controlled application of force by the operator.

Retraction Collar.

Figure 44:
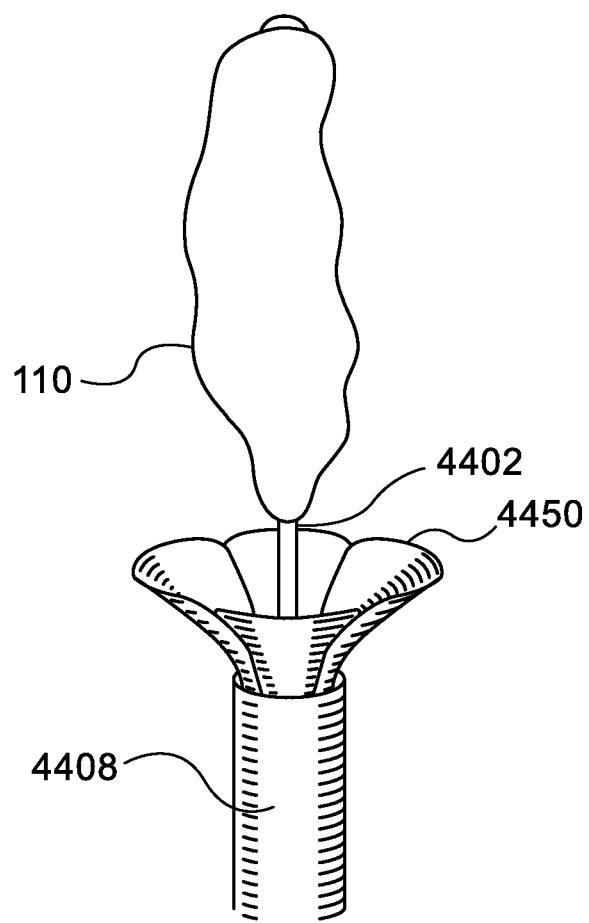
FIG. 44 shows an ablation device with an inner sheath having a conical distal end, according to many embodiments.

As shown in FIG. 44, in some embodiments, an inner sheath may be slideably positioned inside sheath 4408. The distal end of this second, inner sheath may be cone shaped and may have a tendency to radially expand when not limited by the external sheath 4408. When pushed forward out of the external sheath 4408, the distal end of the second, inner sheath may expand and create a conical "collar" 4450. This structure 4450 may provide a wide opening which may ensure that when the balloon 110 and electrodes are retracted back into the sheath 4408 with tube 4402, they will not get stuck on the edge of the external sheath 4408. Such an expanding cone shape 4450 may be made for example by a large conical sheath of a relatively rigid material cut into several "leaves" as shown in FIG. 44, by a sheath of an elastic material, by a braid embedded in polymer or other methods known in the art.

Since the collar 4450 of the inner sheath may be bulky due to overlap between its leaves, or folding of its wider conical part, it may not be possible to pull it back into sheath 4208 together with balloon 110. FIGS. 45A to 45D show a solution to this issue.

Figure 45A:
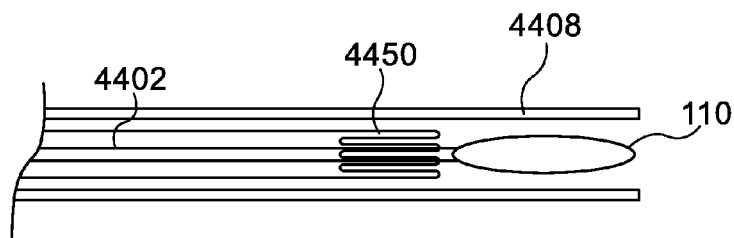
FIGS. 45A, 45B, 45C, and 45D show a method of retracting a deflated balloon using the ablation device of FIG. 44, according to many embodiments.

FIGS. 45A to 45D are schematic longitudinal sections of the device showing balloon 110 and balloon inflation tube 4402 going through sheath 4408. In FIG. 45A, balloon 110 is positioned proximal to distal tip of sheath 4408, prior to deployment in the bladder BL. Collar 4450 is proximal to balloon 110, and thus both have sufficient space within sheath 4408.

Figure 45B:
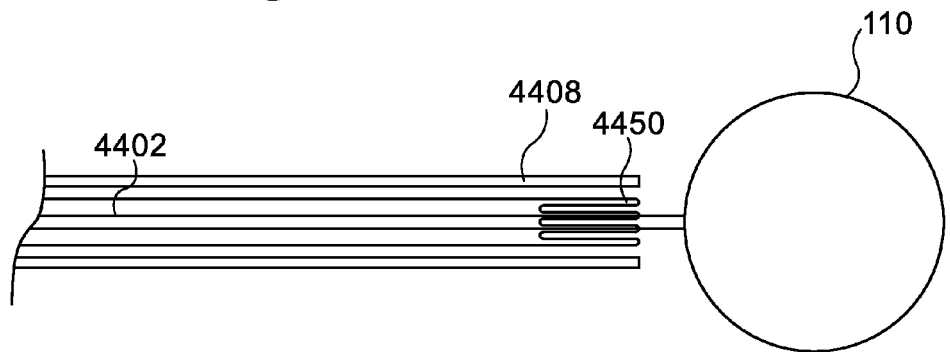

FIG. 45B shows balloon 110 deployed and inflated as in the bladder BL, while collar 4450 is still within sheath 4408.

Figure 45C:
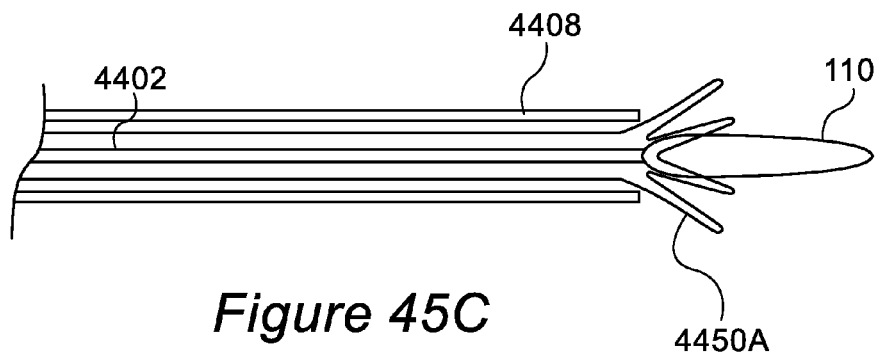

FIG. 45C shows deployed collar 4450a distal to sheath 4408 distal tip. Retraction of balloon 110 may be performed through deployed collar 4450a which eases entry of all part of balloon 110 including balloon folds, electrode wires, and electrode loops into sheath 4408.

Figure 45D:
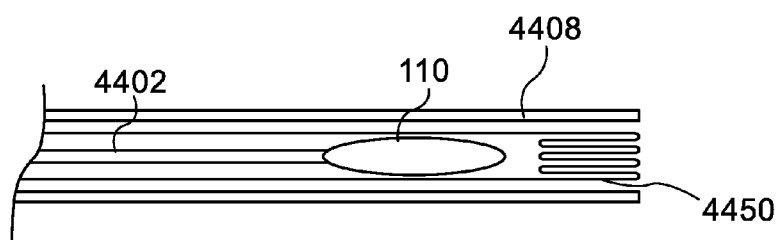

FIG. 45D shows balloon 110 retracted further proximally into sheath 4408, and collar 4450 retracted and crimped back into sheath 4408, this time positioned distal to balloon 110 within sheath 4408. In this manner, both balloon 110 and collar 4450 may have sufficient space in sheath 4408. Generally, any distal part of the catheter or expandable member 110, such as for example cap 4207, should have an outer diameter smaller than the inner diameter of sheath 4408, in order for such distal part to be retracted into sheath 4408.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for treating a disorder in a hollow bodily organ, the device comprising:
   a shaft advancable through a bodily channel of a patient to reach a cavity of the organ;
   an expandable member coupled to a distal end of the shaft, the expandable member having a collapsed configuration advancable through the bodily passage to reach the cavity of the organ and an expanded configuration configured to contact an inner wall of the organ when the expandable member is advanced therein;
   at least one longitudinal conductor disposed over an outer surface of the expandable member and fixedly coupled to a distal end of the expandable member; and
   at least one latitudinal conductor disposed over the outer surface of the expandable member and transverse to the at least one longitudinal conductor,
   wherein the at least one longitudinal conductor is configured to slide across the outer surface of the expandable member as the expandable member transitions between the collapsed and expanded configurations, and
   wherein the at least one longitudinal conductor is configured to slide in a direction substantially transverse to the at least one latitudinal conductor as the expandable member transitions between the collapsed and expanded configurations.

2. The device of claim 1, wherein the at least one longitudinal conductor comprises at least one ablation electrode configured to create a tissue region having reduced electrical propagation in the inner wall of the organ to modify one or more of a mechanical or electrical property of the organ.

3. The device of claim 1, wherein one or more of the at least one latitudinal or longitudinal conductors comprise an ablation electrode configured to create a tissue region having reduced electrical propagation in the inner wall of the organ to modify one or more of a mechanical or electrical property of the organ.

4. The device of claim 1, wherein at least a part of the at least one latitudinal conductor is configured to be parallel to the at least one longitudinal conductor when the expandable member is collapsed, and substantially parallel to an equator of the expandable member when the expandable member is expanded.

5. The device of claim 1, wherein one or more of the at least one longitudinal or latitudinal conductor comprises a bundle of wires, each wire having a surface conductive at different parts.

6. The device of claim 1, further comprising at least one loop through which the at least one longitudinal conductor crosses through as it slides.

7. The device of claim 1, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

8. The device of claim 1, wherein the expandable member is disposed over the distal end of the shaft, and the distal end of the shaft is telescopic to extend in length as the expandable member transitions from the collapsed to the expanded configuration.

9. The device of claim 8, wherein the telescopic distal end of the shaft varies in length from 2 cm to 5 cm when collapsed to 4 cm to 15 cm when fully extended.

10. The device of claim 1, wherein the at least one longitudinal conductor is parallel to a longitudinal axis of the shaft.

11. A method of treating a disorder in a hollow bodily organ, the method comprising:
   advancing a tissue modification device through a bodily passage to reach the cavity of the organ;
   expanding an expandable member disposed at the distal end of the tissue modification device within the cavity such that an outer surface of the expanded expandable member contacts an inner wall of the organ; and
   creating a predetermined pattern of tissue regions having reduced electrical propagation in the inner wall of the hollow bodily organ to modify at least one of a mechanical or an electrical property of the organ,
   wherein the tissue modification device comprises at least one longitudinal conductor disposed over an outer surface of the expandable member and fixedly coupled to a distal tip of the tissue modification device, and
   wherein the at least one longitudinal conductor slides over the outer surface of the expandable member as the expandable member is expanded or collapsed,
   wherein expanding the expandable member comprises lengthening a telescopic shaft coupled to and disposed within the expandable member.

12. The method of claim 11, wherein expanding the expandable member comprises inflating the expandable member.

13. The method of claim 11, wherein the tissue modification device further comprises at least one latitudinal conductor disposed over the outer surface of the expandable member and transverse to the at least one longitudinal conductor, and wherein the predetermined pattern of tissue regions having reduced electrical pattern is based on an arrangement of the at least one longitudinal or latitudinal conductors.

14. The method of claim 11, wherein the predetermined pattern of tissue regions is created as the expandable member is expanded.

15. The method of claim 11, wherein creating the predetermined pattern of tissue regions having reduced electrical propagation comprises creating an ablation pattern on the inner wall of the organ.

16. The method of claim 11, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

17. A method of treating a disorder in a hollow bodily organ, the method comprising:
   advancing a tissue modification device through a bodily passage to reach the cavity of the organ;
   expanding an expandable member disposed at the distal end of the tissue modification device within the cavity such that an outer surface of the expanded expandable member contacts an inner wall of the organ; and
   creating a predetermined pattern of tissue regions having reduced electrical propagation in the inner wall of the hollow bodily organ to modify at least one of a mechanical or an electrical property of the organ,
   wherein the tissue modification device comprises at least one longitudinal conductor disposed over an outer surface of the expandable member and fixedly coupled to a distal tip of the tissue modification device, and wherein the at least one longitudinal conductor slides over the outer surface of the expandable member as the expandable member is expanded or collapsed, wherein the tissue modification device further comprises at least one latitudinal conductor disposed over the outer surface of the expandable member and transverse to the at least one longitudinal conductor, and wherein the predetermined pattern of tissue regions having reduced electrical pattern is based on an arrangement of the at least one longitudinal or latitudinal conductors.

18. The method of claim 17, wherein expanding the expandable member comprises inflating the expandable member.

19. The method of claim 17, wherein the predetermined pattern of tissue regions is created as the expandable member is expanded.

20. The method of claim 17, wherein creating the predetermined pattern of tissue regions having reduced electrical propagation comprises creating an ablation pattern on the inner wall of the organ.

21. The method of claim 17, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

22. A device for treating a disorder in a hollow bodily organ, the device comprising:
   a shaft advancable through a bodily channel of a patient to reach a cavity of the organ;
   an expandable member coupled to a distal end of the shaft, the expandable member having a collapsed configuration advancable through the bodily passage to reach the cavity of the organ and an expanded configuration configured to contact an inner wall of the organ when the expandable member is advanced therein;
   at least one longitudinal conductor disposed over an outer surface of the expandable member and fixedly coupled to a distal end of the expandable member; and
   at least one latitudinal conductor disposed over the outer surface of the expandable member and transverse to the at least one longitudinal conductor,
   wherein the at least one longitudinal conductor is configured to slide across the outer surface of the expandable member as the expandable member transitions between the collapsed and expanded configurations, and
   wherein at least a part of the at least one latitudinal conductor is configured to be parallel to the at least one longitudinal conductor when the expandable member is collapsed, and substantially parallel to an equator of the expandable member when the expandable member is expanded.

23. The device of claim 22, wherein the at least one longitudinal conductor comprises at least one ablation electrode configured to create a tissue region having reduced electrical propagation in the inner wall of the organ to modify one or more of a mechanical or electrical property of the organ.

24. The device of claim 22, wherein one or more of the at least one latitudinal or longitudinal conductor s comprise an ablation electrode configured to create a tissue region having reduced electrical propagation in the inner wall of the organ to modify one or more of a mechanical or electrical property of the organ.

25. The device of claim 22, wherein one or more of the at least one longitudinal or latitudinal conductor comprises a bundle of wires, each wire having a surface conductive at different parts.

26. The device of claim 22, further comprising at least one loop through which the at least one longitudinal conductor crosses through as it slides.

27. The device of claim 22, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

28. The device of claim 22, wherein the expandable member is disposed over the distal end of the shaft, and the distal end of the shaft is telescopic to extend in length as the expandable member transitions from the collapsed to the expanded configuration.

29. The device of claim 28, wherein the telescopic distal end of the shaft varies in length from 2 cm to 5 cm when collapsed to 4 cm to 15 cm when fully extended.

30. The device of claim 22, wherein the at least one longitudinal conductor is parallel to a longitudinal axis of the shaft.

31. A device for treating a disorder in a hollow bodily organ, the device comprising:
   a shaft advancable through a bodily channel of a patient to reach a cavity of the organ;
   an expandable member coupled to a distal end of the shaft, the expandable member having a collapsed configuration advancable through the bodily passage to reach the cavity of the organ and an expanded configuration configured to contact an inner wall of the organ when the expandable member is advanced therein;
   at least one longitudinal conductor disposed over an outer surface of the expandable member and fixedly coupled to a distal end of the expandable member, wherein the at least one longitudinal conductor is configured to slide across the outer surface of the expandable member as the expandable member transitions between the collapsed and expanded configurations; and
   at least one loop through which the at least one longitudinal conductor crosses through as it slides.

32. The device of claim 31, wherein the at least one longitudinal conductor comprises at least one ablation electrode configured to create a tissue region having reduced electrical propagation in the inner wall of the organ to modify one or more of a mechanical or electrical property of the organ.

33. The device of claim 31, further comprising at least one latitudinal conductor disposed over the outer surface of the expandable member and transverse to the at least one longitudinal conductor.

34. The device of claim 33, wherein one or more of the at least one latitudinal or longitudinal conductors comprise an ablation electrode configured to create a tissue region having reduced electrical propagation in the inner wall of the organ to modify one or more of a mechanical or electrical property of the organ.

35. The device of claim 33, wherein one or more of the at least one longitudinal or latitudinal conductor comprises a bundle of wires, each having a surface conductive at different parts.

36. The device of claim 31, wherein the at least one longitudinal conductor comprises a bundle of wires, each wire having a surface conductive at different parts.

37. The device of claim 31, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

38. The device of claim 31, wherein the expandable member is disposed over the distal end of the shaft, and the distal end of the shaft is telescopic to extend in length as the expandable member transitions from the collapsed to the expanded configuration.

39. The device of claim 38, wherein the telescopic distal end of the shaft varies in length from 2 cm to 5 cm when collapsed to 4 cm to 15 cm when fully extended.

40. The device of claim 31, wherein the at least one longitudinal conductor is parallel to a longitudinal axis of the shaft.

41. A device for treating a disorder in a hollow bodily organ, the device comprising:
  a shaft advancable through a bodily channel of a patient to reach a cavity of the organ;
  an expandable member coupled to a distal end of the shaft, the expandable member having a collapsed configuration advancable through the bodily passage to reach the cavity of the organ and an expanded configuration configured to contact an inner wall of the organ when the expandable member is advanced therein; and
  at least one longitudinal conductor disposed over an outer surface of the expandable member and fixedly coupled to a distal end of the expandable member,
  wherein the at least one longitudinal conductor is configured to slide across the outer surface of the expandable member as the expandable member transitions between the collapsed and expanded configurations, and
  wherein the expandable member is disposed over the distal end of the shaft, and the distal end of the shaft is telescopic to extend in length as the expandable member transitions from the collapsed to the expanded configuration.

42. The device of claim 41, wherein the at least one longitudinal conductor comprises at least one ablation electrode configured to create a tissue region having reduced electrical propagation in the inner wall of the organ to modify one or more of a mechanical or electrical property of the organ.

43. The device of claim 41, further comprising at least one latitudinal conductor disposed over the outer surface of the expandable member and transverse to the at least one longitudinal conductor.

44. The device of claim 43, wherein one or more of the at least one latitudinal or longitudinal conductors comprise an ablation electrode configured to create a tissue region having reduced electrical propagation in the inner wall of the organ to modify one or more of a mechanical or electrical property of the organ.

45. The device of claim 43, wherein one or more of the at least one longitudinal or latitudinal conductor comprises a bundle of wires, each having a surface conductive at different parts.

46. The device of claim 41, wherein the at least one longitudinal conductor comprises a bundle of wires, each wire having a surface conductive at different parts.

47. The device of claim 41, wherein the hollow bodily organ is selected from the group comprising a urinary bladder, a kidney, a vagina, a uterus, a fallopian tube, a colon, a large intestine, a small intestine, a stomach, an esophagus, a gall bladder, a bronchus, and an alveolus of the lung.

48. The device of claim 41, wherein the telescopic distal end of the shaft varies in length from 2 cm to 5 cm when collapsed to 4 cm to 15 cm when fully extended.

49. The device of claim 41, wherein the at least one longitudinal conductor is parallel to a longitudinal axis of the shaft.

* * * * *